United States Patent
Raymond et al.

(10) Patent No.: US 9,556,122 B2
(45) Date of Patent: *Jan. 31, 2017

(54) LUMINESCENT 1-HYDROXY-2-PYRIDINONE CHELATES OF LANTHANIDES

(71) Applicant: THE REGENTS OF THE UNIVERSITY OF CALIFORNIA, Oakland, CA (US)

(72) Inventors: Kenneth N. Raymond, Berkeley, CA (US); Jide Xu, Berkeley, CA (US); Evan G. Moore, Berkeley, CA (US); Eric J. Werner, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 300 days.

This patent is subject to a terminal disclaimer.

(21) Appl. No.: 14/048,475

(22) Filed: Oct. 8, 2013

(65) Prior Publication Data

US 2014/0039169 A1 Feb. 6, 2014

Related U.S. Application Data

(63) Continuation of application No. 12/373,275, filed as application No. PCT/US2007/073185 on Jul. 10, 2007, now Pat. No. 8,557,601.

(60) Provisional application No. 60/819,904, filed on Jul. 10, 2006.

(51) Int. Cl.
| | |
|---|---|
| C07D 213/89 | (2006.01) |
| C07D 217/26 | (2006.01) |
| C09K 11/06 | (2006.01) |
| H05B 33/14 | (2006.01) |

(52) U.S. Cl.
CPC .......... *C07D 213/89* (2013.01); *C07D 217/26* (2013.01); *C09K 11/06* (2013.01); *H05B 33/14* (2013.01); *C09K 2211/1022* (2013.01); *C09K 2211/1029* (2013.01); *C09K 2211/1044* (2013.01); *C09K 2211/1088* (2013.01); *C09K 2211/185* (2013.01)

(58) Field of Classification Search
CPC .............................. C07D 213/89; C07D 217/26
See application file for complete search history.

(56) References Cited

U.S. PATENT DOCUMENTS

| | | |
|---|---|---|
| 2,977,332 A | 3/1961 | Zumstein |
| 4,181,654 A | 1/1980 | Weitl et al. |
| 4,309,305 A | 1/1982 | Weitl et al. |
| 4,442,305 A | 4/1984 | Weitl et al. |
| 4,543,213 A | 9/1985 | Weitl et al. |
| 4,666,927 A | 5/1987 | Hider et al. |
| 4,698,431 A | 10/1987 | Raymond et al. |
| 4,748,184 A | 5/1988 | Stout et al. |
| 4,855,225 A | 8/1989 | Fung et al. |
| 4,868,103 A | 9/1989 | Stavrianopoulos et al. |
| 4,939,254 A | 7/1990 | McMurry et al. |
| 4,978,614 A | 12/1990 | Bronstein |
| 5,010,191 A | 4/1991 | Engelstad et al. |
| 5,047,519 A | 9/1991 | Hobbs, Jr. et al. |
| 5,049,280 A | 9/1991 | Raymond et al. |
| 5,252,462 A | 10/1993 | Drevin et al. |
| 5,435,990 A | 7/1995 | Cheng et al. |
| 5,470,896 A | 11/1995 | Wegmann et al. |
| 5,478,741 A | 12/1995 | Maret et al. |
| 5,482,698 A | 1/1996 | Griffiths |
| 5,601,800 A | 2/1997 | Katti et al. |
| 5,624,901 A | 4/1997 | Raymond et al. |
| 5,820,849 A | 10/1998 | Schmitt-Willich et al. |
| 5,892,029 A | 4/1999 | Raymond et al. |
| 5,989,823 A | 11/1999 | Jayasena et al. |
| 5,998,146 A | 12/1999 | Latva et al. |
| 6,221,476 B1 | 4/2001 | Bruening et al. |
| 6,406,297 B1 | 6/2002 | Raymond et al. |
| 6,515,113 B2 | 2/2003 | Raymond et al. |
| 6,846,915 B2 | 1/2005 | Raymond et al. |
| 6,864,103 B2 | 3/2005 | Raymond et al. |
| 7,018,850 B2 | 3/2006 | Raymond et al. |
| 7,404,912 B2 | 7/2008 | Raymond et al. |
| 7,442,558 B2 | 10/2008 | Raymond et al. |
| 7,718,781 B2 | 5/2010 | Raymond et al. |
| 7,794,691 B2 | 9/2010 | Morgenstern et al. |
| 8,173,800 B2 | 5/2012 | Raymond et al. |

(Continued)

FOREIGN PATENT DOCUMENTS

| | | |
|---|---|---|
| CA | 2099542 A1 | 1/1994 |
| EP | 0578067 A1 | 1/1994 |

(Continued)

OTHER PUBLICATIONS

Aime, S. et al. "Determination of the Prototropic Exhange Rate at the Water Molecule Coordinated to an Anionic Paramagnetic $Gd^{III}$ Chelate", *European Journal of Inorganic Chemistry*, vol. 9, 1283-1289 (1998).

Bailly et al., "Nouvelle méthode de synthèse du 3,4,3 Li 1,2 HOPO (1,5,10,14-tétra(1-hydroxy-2-pyridone-6 oyl) 1,5,10,14 tétraazatétradécane)", *C. R. Acad. Sci. Paris 1*, Serie II: 241-245 (1998).

Bergeron, R.J. et al., "Catecholamide Chelators for Actinide Environmental and Human Decontamination," *Chemical Abstracts*, vol. 105, No. 25, Columbus, Ohio, U.S. Abstract No. 221872Z, p. 374 (Dec. 1986).

(Continued)

Primary Examiner — Joseph Kosack
(74) Attorney, Agent, or Firm — Morgan, Lewis & Bockius LLP; Jeffry S. Mann

(57) ABSTRACT

The present invention provides luminescent complexes between a lanthanide ion and an organic ligand which contains 1,2-hydroxypyridinone units. The complexes of the invention are stable in aqueous solutions and are useful as molecular probes, for example in medical diagnostics and bioanalytical assay systems. The invention also provides methods of using the complexes of the invention.

18 Claims, No Drawings

(56) References Cited

U.S. PATENT DOCUMENTS

| | | | |
|---|---|---|---|
| 8,507,199 B2 | 8/2013 | Butlin et al. | |
| 8,551,453 B2 | 10/2013 | Raymond et al. | |
| 8,557,601 B2* | 10/2013 | Raymond | C07D 213/89 436/172 |
| 8,729,258 B2 | 5/2014 | Raymond et al. | |
| 2002/0128451 A1 | 9/2002 | Raymond et al. | |
| 2002/0188111 A1 | 12/2002 | Raymond et al. | |
| 2003/0027189 A1 | 2/2003 | Raymond et al. | |
| 2003/0095922 A1 | 5/2003 | Raymond et al. | |
| 2003/0199688 A1 | 10/2003 | Kriesel et al. | |
| 2004/0028611 A1 | 2/2004 | Frangioni | |
| 2004/0249586 A1 | 12/2004 | Boge et al. | |
| 2005/0008570 A1 | 1/2005 | Raymond et al. | |
| 2005/0058604 A1 | 3/2005 | Raymond et al. | |
| 2006/0135842 A1 | 6/2006 | Larsen et al. | |
| 2006/0228297 A1 | 10/2006 | Larsen et al. | |
| 2006/0286567 A1 | 12/2006 | Raymond et al. | |
| 2007/0134160 A1 | 6/2007 | Leif et al. | |
| 2008/0213780 A1 | 9/2008 | Butlin et al. | |
| 2008/0213917 A1 | 9/2008 | Raymond et al. | |
| 2008/0293155 A1 | 11/2008 | Raymond et al. | |
| 2009/0023928 A1 | 1/2009 | Raymond et al. | |
| 2009/0036537 A1 | 2/2009 | Raymond et al. | |
| 2010/0015725 A1* | 1/2010 | Raymond | C07D 213/89 436/501 |
| 2010/0151591 A1 | 6/2010 | Butlin et al. | |
| 2010/0167289 A1 | 7/2010 | Butlin et al. | |
| 2011/0189088 A1 | 8/2011 | Xu et al. | |
| 2012/0190012 A1 | 7/2012 | Butlin et al. | |
| 2012/0214253 A1 | 8/2012 | Butlin et al. | |
| 2012/0214843 A1 | 8/2012 | Durbin-Heavey et al. | |
| 2012/0329174 A1 | 12/2012 | Raymond et al. | |
| 2014/0039169 A1 | 2/2014 | Raymond et al. | |

FOREIGN PATENT DOCUMENTS

| | | |
|---|---|---|
| EP | 2423201 A1 | 2/2012 |
| JP | 2003-535812 A | 12/2003 |
| WO | WO 89/11475 A1 | 11/1989 |
| WO | WO 91/12530 A1 | 8/1991 |
| WO | WO 92/11039 A1 | 7/1992 |
| WO | WO 97/00245 | 1/1997 |
| WO | WO 97/00245 A1 | 1/1997 |
| WO | WO 97/45539 A1 | 12/1997 |
| WO | WO 00/48990 A1 | 8/2000 |
| WO | WO 00/48991 A1 | 8/2000 |
| WO | WO 03/016923 | 2/2003 |
| WO | WO 03/016923 A2 | 2/2003 |
| WO | WO 2005/030711 A2 | 4/2005 |
| WO | WO 2005/030727 A1 | 4/2005 |
| WO | WO 2006/001835 A2 | 1/2006 |
| WO | WO 2007/121453 A2 | 10/2007 |
| WO | WO 2008/008797 A2 | 1/2008 |
| WO | WO 2008/063721 A2 | 5/2008 |
| WO | WO 2008/092120 A1 | 7/2008 |
| WO | WO 2010/034931 A1 | 4/2010 |
| WO | WO 2010/051544 A2 | 5/2010 |
| WO | WO 2011/025790 A1 | 3/2011 |
| WO | WO 2011/098611 A2 | 8/2011 |
| WO | WO 2013/167754 A1 | 11/2013 |
| WO | WO 2013/167755 A1 | 11/2013 |
| WO | WO 2013/167756 A1 | 11/2013 |

OTHER PUBLICATIONS

Bodansky, M. et al., "The Practice of Peptide Synthesis", 2nd Ed., Springer-Verlag Berlin Heidelberg, 96-125 (1984).
Bryant, L.H. et. al. "Synthesis and relaxometry of high-generation {G=5, 7, 9, and 10} PAMAM dendrimer-DOTA-gadolinium chelates," *J. Magnetic Resonance Imaging*, v. 9, n. 2, p. 348-352, (1999).
Budimir et al., "Study of metal complexes of a tripodal hydroxypyridinone ligand by electrospray tandem mass spectrometry", *Rapid Communications in Mass Spectrometry*, vol. 19, No. 13, pp. 1822-1828 (2005).
Bulman, R.A. et al., "An Examination of Some Complexing Agents for Ability to Remove Intracellularly Deposited Plutonium," *Chemical Abstracts*, vol. 92, No. 13, Columbus, Ohio, U.S. Abstracts No. 106582f, p. 286 (Mar. 1980).
Burgada et al., "Synthesis of 3, 4, 3, Li 1, 2, HOPO Labelled with $^{14}$C", *Journal of Labelled Compounds and Radiopharmaceuticals*, vol. 44, No. 1, pp. 13-19 (2001).
Choudhary, et al., "New compounds of tetradentate Schiff bases with vanadium (IV) and vanadium (V)", *Journal of the Chemical Society*, Dalton Transactions, No. 24, pp. 4437-4446 (1999).
Cohen, S. et al., "Syntheses and Relaxation Properties of Mixed Gadolinium Hydroxypyridinonate MRI Contrast Agents", *Inorg. Chem*. 39, 5747-5756 (2000).
Curtet, C. et al., "In Vivo diagnosis and therapy of human tumors with monoclonal antibodies," *Nuclear Medicine and Biology, Int. J. of Radiation Applications and Instrumentation Part B*, v. part b/16, n. 2, p. 180, (1989).
Dahlén, "Detection of Biotinylated DNA Probes by Using Eu-Labeled Streptavidin and Time-Resolved Fluorometry", *Anal. Biochem.*, 164:78-83 (1987).
Durbin, P. et al., "Specific Sequestering Agents for the Actinides: Enhancement of Putonium-238 Elimination from the Emice by Poly(catechoylanide) Ligands," *Chemical Abstracts*, vol. 101, No. 15, Columbus Ohio, U.S. Abstract No. 125980e, p. 328, (Oct. 1984).
Durbin, P. et al., "In vivo Chelation of Am(III), Pu(IV), Np(V) and U(VI) in Mice by TREN-(Me-3,2-HOPO)", *Chemical Abstracts*, vol. 122, No. 1, 2, p. 517 (Jan. 1995).
Frank, H. et al., "Detection of pulmonary emboli by using MR angiography with MPEG-PL-GdDTPA: an experimental study in rabbits," *American J. of Roentgenology*, v. 162, n. 5, p. 1041-1046, (1994).
Hajela, S. et al., "A tris-hydroxymethyl-substituted derivative of Gd-TREN-Me-3,2-HOPO: An MRI relaxation agent with imroved efficiency," *J. Am. Chem. Soc.*, 122, p. 11228-11229, (2000).
Hajela, S.P., et al., "Synthesis of homochiral tris(2-alkyl-2-aminoethyl) amine derivatives from chiral a-amino aldehydes and their application in the synthesis of water soluble chelators,"*Inorg. Chem.*, 40, p. 3208-3216, (May 16, 2001).
Johnson, A.R., et al., "Sunthesis of a ligand based upon a new entry into the 3-hydroxy-N-alkyl-2(1H0-pyridinone ring system and thermodynamic evaluation of its gadolinium complex," *Inorg. Chem.*, v. 39, p. 2652-2660, (2000).
Karpishin, et al., "Stereoselectivity in Chiral Fe$^{III}$ and Ga$^{III}$ Tris(catecholate) Complexes Effected by Nonbonded, Weakly Polar Interactions", *Jounral of the American Chemical Society*, vol. 115, No. 14, pp. 6115-6125 (1993).
Puerta, et al., "Tris(pyrone) Chelates of Gd(III) as High Solubility MRI-CA", *Journal of the American Chemical Society*, Vo. 128, p. 2222-2223 (2006).
Raymond, K. N. et al., "Next Generation, High Relativity Gadolinium MRI Agents", *Bioconjugate Chemistry, American Chem. Soc.*, pp. 3-8 (2005).
Scarrow, R. et al., "Ferric Ion Sequestering Agents. 14.[1] 1-Hydroxy-2(1H)-pyridinone Complexes: Properties and Structure of a Novel Fe-Fe Dimer," *J. Am. Chem. Soc.*, vol. 107, No. 23, 6450-6545 (1985).
Soulère et al., "Selective Inhibition of Fe-*versus* Cu/Zn-Superoxide Dismutases by 2,3-Dihydrosybenzoic Acid Derivavtives", *Chemical & Pharmaceutical Bulletin*, vol. 50, No. 5, pp. 578-582 (2002).
Southwood-Jones, R. et al., "Oxygen-17 NMR and EPR studies of water exchange from the first coordination sphere of gadolinium(III) aquoion and gadolinium(III) propylenediaminetetraacetate$^{a)b)}$", *Journal of Chemical Physics*, vol. 73, No. 12, 5909-5918 (1980).
Stack, et al., "Rational reduction of the conformational space of a siderophore analog through nonbonded interactions: the role of entropy in enterobactin", *Journal of the American Chemical Society*, vol. 115, No. 14, pp. 6466-6467 (1993).
Streater, M. et al., "Novel 3-Hydroxy-2(1-H)-pyridinones. Synthesis, Iron(III)-Chelating Properties, and Biological Activity," *J. Med. Chem.*, vol. 33, No. 6, 1749-1755 (1990).

(56) References Cited

OTHER PUBLICATIONS

Sunderland et al., "6-Carboxamido-5, 4-Hydroxypyrimidinones: A New Class of Heterocyclic Ligands and Their Evaluation as Gadolinium Chelating Agents", Inorganic Chemistry, vol. 40, pp. 6746-6756 (2001).
Syvänen et al., "Time-resolved fluorometry: a sensitive method to quantify DNA-hybrids", Nucleic Acids Research 14: 1017-1028 (1986).
Tedeschi et al., "A solid-state study of eight-coordinate lanthanide (III) complexes (Ln=Eu, Gd, Tb, Dy) with 1-hydroxy-2-pyridinone", Dalton Transactions, pp. 1738-1745 (2003).
Uhlir, L.C., "Mixed Functionality Actinide Sequestering Agents", Ph.D. Thesis, University of California, Berkeley (1992).
Uhlir, L. et al., "Specific Sequestering Agents for the Actinides. 21. Synthesis and Initial Biological Testing of Octadentate Mixed Catecholate-Hydroxypyridinonate Ligands," J. Med. Chem., vol. 36, No. 4, 504-509 (1993).
Unger, E.C. et al., "Gadolinium-containing copolymeric chelates—a new potential MR contrast agent," Magnetic Resonance Materials in Physics, Biology and Medicine, p. 154-162, (1998).
Vander Elst, L., et al., "Stereospecific binding of MRI contrast agents to human serum albumin: the case of Gd-(S)-EOB-DTPA (Eovist) and its (R) isomer," J. Biol. Inorg. Chem., 6, p. 196-200, (Jan. 17, 2001).
Villa, Alessandra et al. "Force Field Parametrization for Gadolinium Complexes Based on ab Initio Potential Energy Surface Calculations", J. Phys. Chem. A 104, 3421-3429 (2000).
Werner, E. J. et al., "Highly Soluble Tris-hydroxpyridonate Gd(III) Complexes with Increased Hydration Number, Fast Water Exchange, Slow Electronic Relaxation, and High Relaxivity", J. Am. Chem. Soc., vol. 129, pp. 1870-1871 (2007).
White et al., "Specific Sequestering Agents for the Actinides. 16. Synthesis and Initial Bioological Testing of Polydentate Oxohydroxypyridinecarboxylate Ligands" J. Med. Chem. 31: 11-18 (1988).
Xu, J. et al., "Gadolinium complex of tris[(3-hydroxy-1-methyl-2-oxo-1,2-didehydropyridine-4-carboxamido)ethyl]-amine: A new class of gadolinium magnetic resonance relaxation agents," J. Am. Chem. Soc., 117, p. 7245-7246, (1995).
Xu, J. et al., "Specific Sequestering Agents for the Actinides. 28. Synthesis and Initial Evaluation of Multidentate 4-Carbamoyl-3-hydroxy-1-methyl-2(1H)-pyridinone Ligands for in-Vivo Plutonium(IV) Chelation," J. Med. Chem., 38, 2606-2614 (1995).
Xu, J. et al., "Gadolinium (III) 1,2-hydroxypyridonate-based complexes: toward MRI contrast agents of high relaxivity", Inorganic Chemistry, pp. 5492-5494 (2004).
Aime et al., Determination of the Prototropic Exchange Rate at the Water Molecule Coordinated to an Anionic Paramagnetic GdIII Chelate. Eur. J. Inorg. Chem. 1998, 1998 (9): 1283-1289.
Aime et al., Paramagnetic GdIII FeIII heterobimetallic complexes of DTPA-bis-salicylamide. Spectrochim. Acta A 1993, 49 (9), 1315-1322.
Alaverdian et al., A family of novel DNA sequencing instruments based on single-photon detection. Electrophoresis 2002, 23 (16): 2804-2817.
Allicotti et al., A time-resolved fluorescence immunoassay (DELFIA) increases the sensitivity of antigen-driven cytokine detection. J. Immunoassay Immunochem. 2003, 24 (4), 345-358.
Alpha et al., Luminescence Probes: The Eu3⊕- and Tb3⊕-Cryptates of Polypyridine Macrobicyclic Ligands. Angew. Chem. Int. Ed. Engl. 1987, 26 (12), 1266-1267.
Anderson and Welch, Radiometal-Labeled Agents (Non-Technetium) for Diagnostic Imaging. Chem. Rev. 1999, 99 (9), 2219-2234.
Arnaud et al., Synthesis of macrocyclic polyhydroxy tetralactams derived from L-tartaric acid and β-hydroxyglutaric acid. Tetrahedron 1997, 53 (40), 13757-13768.
Bai et al., Photocleavage of a 2-nitrobenzyl linker bridging a fluorophore to the 5′ end of DNA. Proc. Natl. Acad. Sci. U.S.A. 2003, 100 (2), 409-413.

Bailly and Burgada, Nouvelle methode de synthese du 3,4,3 LI 1,2 HOPO (1,5,10,14-tetra(1-hydroxy-2-pyridone-6 oyl) 1,5,10,14 tetraazatetradecane). C. R. Acad. Sci., Ser. IIc: Chim. 1998, 1 (4), 241-245.
Batard et al., Use of Phycoerythrin and Allophycocyanin for Fluorescence Resonance Energy Transfer Analyzed by Flow Cytometry: Advantages and Limitations. Cytometry 2002, 48 (2), 97-105.
Beeby et al., Luminescence imaging microscopy and lifetime mapping using kinetically stable lanthanide(III) complexes. J. Photochem. Photobiol. B 2000, 57 (2-3), 83-89.
Bergeron and Navratil, Catecholamide Chelators for Actinide Environmental and Human Decontamination. Chem. Abstr. 1986, 105, 221872z.
Blomberg et al., Terbium and rhodamine as labels in a homogeneous time-resolved fluorometric energy transfer assay of the beta subunit of human chorionic gonadotropin in serum. Clin Chem 1999, 45 (6 Pt 1), 855-861.
Bodanszky and Bodanszky, Activation and Coupling [excerpt]. In the Practice of Peptide Synthesis, 2nd ed.; Springer-Verlag Berlin Heidelberg, 1984; pp. 96-125.
Boswell and Brechbiel, Development of radioimmunotherapeutic and diagnostic antibodies: an inside-out view. Nucl. Med. Biol. 2007, 34 (7), 757-778.
Brooker et al., Figure-of-eight Shaped Metal-free Amide-containing Schiff-base Macrocycles and Two Dicobalt(III) Amide Complexes. Chemical Abstracts 2002, HCAplus Accession No. 2002:593344.
Bruchez et al., Semiconductor Nanocrystals as Fluorescent Biological Labels. Science 1998, 281 (5385), 2013-2016.
Brumley and Smith, Rapid DNA sequencing by horizontal ultrathin gel electrophoresis. Nucleic Acids Res. 1991, 19 (15), 4121-4126.
Brunet et al., Lanthanide complexes of polycarboxylate-bearing dipyrazolylpyridine ligands with near-unity luminescence quantum yields: the effect of pyridine substitution. Photochem. Photobiol. Sci. 2002, 1 (8), 613-618.
Bryant et al., Synthesis and relaxometry of high-generation {G=5, 7, 9, and 10} PAMAM dendrimer-DOTA-gadolinium chelates. J. Magn. Reson. Imaging 1999, 9 (2), 348-352.
Budimir et al., Study of metal complexes of a tripodal hydroxypyridinone ligand by electrospray tandem mass spectrometry, Rapid Commun. Mass Spectrom. 2005, 19 (13), 1822-1828.
Bulman et al., An examination of some complexing agents for ability to remove intracellularly deposited plutonium. Chem. Abstr. 1980, 92, 106582f.
Bunzli et al., Towards materials with planned properties : dinuclear f-f helicates and d-f non-convalent podates based on benzimidazole-pyridine binding units. J. Alloys Compd. 1997, 249 (1-2), 14-24.
Burgada et al., Synthesis of 3,4,3 LI 1,2 HOPO labelled with 14C. J. Label. Compd. Radiopharm. 2001, 44 (1), 13-19.
Cardullo et al., Detection of nucleic acid hybridization by nonradiative fluorescence resonance energy transfer. Proc. Natl. Acad. Sci. USA 1988, 85 (23), 8790-8794.
Chan and Nie, Quantum Dot Bioconjugates for Ultrasensitive Nonisotopic Detection. Science 1998, 281 (5385), 2016-2018.
Chen and Selvin, Lifetime- and color-tailored fluorophores in the micro- to millisecond time regime. J. Am. Chem. Soc. 2000, 122 (4), 657-660.
Chen and Selvin, Thiol-reactive luminescent chelates of terbium and europium. Bioconjug. Chem. 1999, 10 (2), 311-315.
Choudhary et al., New compounds of tetradentate Schiff bases with vanadium (IV) and vanadium (V). J. Chem. Soc., Dalton Trans. 1999, 24, 4437-4446.
Clarke et al., Crystal structure of the tris 1,2-dimethyl-3-hydroxy-4-pyridinone (DMHP) complex with the Fe(III) ion. Inorg. Chim. Acta 1992, 196 (2), 177-183.
Cohen et al., A Novel Salicylate-Based Macrobicycle with a "Split Personality". Inorg. Chem. 1999, 38 (20), 4522-4529.
Cohen et al., Syntheses and relaxation properties of mixed gadolinium hydroxypyridinonate MRI contrast agents. Inorg. Chem. 2000, 39 (25), 5747-5756.
Collins et al., A vision for the future of genomics research. Nature 2003, 422 (6934), 835-847.

(56) References Cited

OTHER PUBLICATIONS

Comby et al., Stable 8-hydroxyquinolinate-based podates as efficient sensitizers of lanthanide near-infrared luminescence. Inorg. Chem. 2006, 45 (2), 732-743.

Curtet, C., In Vivo diagnosis and therapy of human tumors with monoclonal antibodies. Int. J. Radiat. Appl. Instrum., Part B, 1989, 16 (2), 180.

Dahlen, P., Detection of Biotinylated DNA Probes by Using Eu-Labeled Streptavidin and Time-Resolved Fluorometry. Anal. Biochem. 1987, 164 (1), 78-83.

De Sa et al., Spectroscopic properties and design of highly luminescent lanthanide coordination complexes. Coord. Chem. Rev. 2000, 196 (1), 165-195.

Demas and Crosby, Measurement of Photoluminescence Quantum Yields. A Review. J. Phys. Chem. 1971, 75 (8), 991-1024.

Dexter, D.L., A Theory of Sensitized Luminescence in Solids. J. Chem. Phys. 1953, 21 (5), 836-850.

Dickins et al., Synthesis, time-resolved luminescence, NMR spectroscopy, circular dichroism and circularly polarised luminescence studies of enantiopure macrocyclic lanthanide tetraamide complexes. Chem. Eur. J. 1999, 5 (3), 1095-1105.

Dickson et al., Time-resolved detection of lanthanide luminescence for ultrasensitive bioanalytical assays. J. Photochem. Photobiol. B. 1995, 27 (1), 3-19.

Doble et al., Toward optimized high-relaxivity MRI agents: the effect of ligand basicity on the thermodynamic stability of hexadentate hydroxypyridonate/catecholate gadolinium(III) complexes. Inorg. Chem. 2003, 42 (16), 4930-4937.

Durbin et al., In vivo chelation of Am(III), Pu(IV), Np(V) and U(VI) in mice by TREN-(Me-3,2-HOPO). Chem. Abstr. 1995, 122, 4449p.

Durbin et al., Specific sequestering agents for the actinides: 10. Enhancement of plutonium-238 elimination from mice by poly(catechoylamide) ligands. Chem. Abstr. 1984, 101, 125980e.

Eid et al., Real-Time DNA Sequencing from Single Polymerase Molecules. Science 2009, 323 (5910), 133-138.

Edelstein et al. Optical properties of Cm(III) in crystals and solutions and their application to Cm(III) speciation. Coord. Chem. Rev. 250, 2006, 948-973.

Farkas et al., Equilibrium studies on copper(II)- and iron(III)-monohydroxamates. Polyhedron 1998, 17 (19), 3331-3342.

Förster, T., Transfer Mechanisms of Electronic Excitation. Discuss. Faraday Soc. 1959, 27, 7-17.

Förster, T., Zwischenmolekulare Energiewanderung and Fluoreszenz. Ann. Phys. 1948, 437 (1-2), 55-75.

Frank et al., Detection of pulmonary emboli by using MR angiography with MPEG-PL-GdDTPA: an experimental study in rabbits. AJR Am. J. Roentgenol. 1994, 162 (5), 1041-1046.

Galaup et al., Mono(di)nuclear eropium(III) complexes of macrobi(tri)cyclic cryptands derived from diazatetralactams as luminophores in aqueous solution. Helv. Chim. Acta. 1999, 82 (4), 543-560.

Glazer, A. N., Light Harvesting by Phycobilisomes. Annu. Rev. Biophys. Biophys. Chem. 1985, 14, 47-77.

Gong, B., Crescent oligoamides: From acyclic "Macrocycles" to folding nanotubes. Chem Eur J 2001, 7 (20), 4336-4342.

Hajela et al., A tris-hydroxymethyl-substituted derivative of Gd-TREN-Me-3,2-HOPO: An MRI relaxation agent with improved efficiency. J. Am. Chem. Soc. 2000, 122 (45), 11228-11229.

Hajela et al., Synthesis of homochiral tris(2-alkyl-2-aminoethyl) amine derivatives from chiral a-amino aldehydes and their application in the synthesis of water soluble chelators. Inorg. Chem. 2001, 40 (13), 3208-3216.

Heid et al., Real time quantitative PCR. Genome Res. 1996, 6 (10), 986-994.

Hemmila et al., Development of luminescent lanthanide chelate labels for diagnostic assays. J. Alloys Compd. 1997, 249 (1-2), 158-162.

Hemmiläet al., Europium as a label in time-resolved immunofluorometric assays. Anal. Biochem. 1984, 137 (2), 335-343.

Hemmila, I. A. In Immunochemistry 1; Johnstone, A. P., Turner, M. W., Eds.; IRL Press: Oxford, U.K., 1997; pp. 193-214.

Hemmila, I., LANCE™: Homogeneous Assay Platform for HTS. J. Biomol. Screening 1999, 4 (6), 303-307.

Hemmilä, I., Luminescent lanthanide chelates—a way to more sensitive diagnostic methods. J. Alloys Compd. 1995, 225 (1-2), 480-485.

Higuchi. et al., Simultaneous Amplification and Detection of Specific DNA Sequences. Biotechnology (NY) 1992, 10 (4), 413-417.

Hochstrasser et al., Distance distribution in a dye-linked oligonucleotide determined by time-resolved fluorescence energy transfer. Biophys. Chem. 1992, 45 (2), 133-141.

Holland et al., Detection of specific polymerase chain reaction product by utilizing the 5'.fwdarw.3' exonuclease activity of Thermus aquaticus DNA polymerase. Proc. Nat. Acad. Sci. USA 1991, 88 (16), 7276-7280.

Jaakkola et al., Solid-phase synthesis of oligonucleotides labeled with luminescent lanthanide(III) chelates. Bioconjug. Chem. 2005, 16 (3), 700-709.

Jagannathan and Soundararajan, "Complexes of lanthanide perchlorated with N,N,N'n'-tetra-amethyl-α-carboxamido-o-anisamide and N, N'-di-t-butyl-60 -carboxamido-o-anisamide" Inorganica Chim. Acta 1979, 37, L449-L451.

Johansson et al., Time Gating Improves Sensitivity in Energy Transfer Assays with Terbium Chelate/Dark Quencher Oligonucleotide Probes. J. Am. Chem. Soc. 2004, 126 (50), 16451-16455.

Johnson et al., Synthesis of a ligand based upon a new entry into the 3-hydroxy-N-alkyl- 2(1H0-pyridinone ring system and thermodynamic evaluation of its gadolinium complex. Inorg. Chem. 2000, 39 (12), 2652-2660.

Ju et al., Fluorescence energy transfer dye-labeled primers for DNA sequencing and analysis. Proc. Natl. Acad. Sci. U.S.A. 1995, 92 (10), 4347-4351.

Karpishin et al., Stereoselectivity in chiral iron(III) and gallium(III) tris(catecholate) complexes effected by nonbonded weakly polar interactions. J. Am. Chem. Soc. 1993, 115 (14), 6115-6125.

Kelly and Lang, Total Synthesis of Dimethyl Sulfomycinamate. J. Org. Chem. 1996, 61 (14), 4623-4633.

Kheterpal et al., DNA sequencing using a four-color confocal fluorescence capillary array scanner. Electrophoresis 1996, 17 (12): 1852-1859.

Kling, J., Ultrafast DNA sequencing. Nat. Biotechnol. 2003, 21 (12), 1425-1427.

Knight, C.G., Fluorimetric Assays of Proteolytic Enzymes. Methods Enzymol. 1995, 248: 18-34.

Kostrikis et al., Spectral Genotyping of Human Alleles. Science 1998, 279 (5354), 1228-1229.

Kulmala et al, Electrochemiluminescent labels for applications in fully aqueous solutions at oxide-covered aluminium electrodes. Anal. Chim. Acta 1999, 386 (1-2), 1-6.

Kunkely and Vogler, Photoluminescence of thorium(IV) 2-methyl-8-quinolinolate. Chem. Phys. Lett. 304, 1999, 187-190.

Lassiter et al., Time-resolved fluorescence imaging of slab gels for lifetime base-calling in DNA sequencing applications. Anal. Chem. 2000, 72 (21), 5373-5382.

Lee et al., Allelic discrimination by nick-translation PCR with fluorogenic probes. Nucleic Acids Res. 1993, 21 (16), 3761-3766.

Lee et al., New energy transfer dyes for DNA sequencing. Nucleic Acids Res. 1997, 25 (14), 2816-2822.

Lee et al., Seven-Color, Homogeneous Detection of Six PCR Products. Biotechniques 1999, 27 (2), 342-349.

Li et al., A photocleavable fluorescent nucleotide for DNA sequencing and analysis. Proc. Natl. Acad. Sci. U.S.A. 2003, 100 (2), 414-419.

Li et al., Shape-persistent aromatic amide oligomers: new tools for supramolecular chemistry, Chem. Asian J. 2006, 1 (6), 766-778.

Lichtenberger and Geyer, Cyanoethylation. II. Substituted β-phenoxypropionic acids. Bull. Soc. Chim. Fr. 1963, 275-282.

Lieberwirth et al., Multiplex dye DNA sequencing in capillary gel electrophoresis by diode laser-based time-resolved fluorescence detection. Anal. Chem. 1998, 70 (22), 4771-4779.

Margulies et al., Genome sequencing in microfabricated high-density picolitre reactors. Nature 2005, 437 (7057), 376-380.

(56) References Cited

OTHER PUBLICATIONS

Mathis, G., HTRF® Technology. J. Biomol. Screen. 1999, 4 (6), 309-314.
Mathis, G., Rare earth cryptates and homogeneous fluoroimmunoassays with human sera. Clin Chem. 1993, 39 (9), 1953-1959.
Mattoussi et al., Self-Assembly of CdSe-ZnS Quantum Dot Bioconjugates Using an Engineered Recombinant Protein. J. Am. Chem. Soc. 2000, 122 (49), 12142-12150.
Metzker et al., Electrophoretically uniform fluorescent dyes for automated DNA sequencing. Science 1996, 271 (5254), 1420-1422.
Metzker, M. L., Emerging technologies in DNA sequencing. Genome Res. 2005, 15 (12), 1767-1776.
Mikola et al., Syntheses and properties of luminescent lanthanide chelate labels and labeled haptenic antigens for homogeneous immunoassays. Bioconjug. Chem. 1995, 6 (3), 235-241.
Momany et al. Crystal structure of dimeric HIV-1 capsid protein. Nat. Struct. Biol. 1996, 3 (9), 763-770.
Moore et al., "Cymothoe sangaris": An Extremely Stable and Highly Luminescent 1,2-Hydroxypyridinonate Chelate of Eu(III). J. Am. Chem. Soc. 2006, 128 (33), 10648-10649.
Moore et al., An octadentate luminescent Eu(III) 1,2-HOPO chelate with potent aqueous stability. Inorg. Chem. 2007, 46 (14), 5468-5470.
Moore et al., Eu (III) Complexes of Functionalized Octadentate 1-Hydroxypyridin-2-ones: Stability, Bioconjugation, and Luminescence Resonance Energy Transfer Studies. Inorg. Chem. 2010, 49, 9928-9939.
Moyer et al. Enhanced liquid-liquid anion exchange using macrocyclic anion receptors: effect of receptor structure on sulphate-nitrate exchange selectivity. Supra Molecular Chemistry. 2010 vol. 22, pp. 653-671.
Mugabe et al., Liposome-mediated gentamicin delivery: development and activity against resistant strains of Pseudomonas aeruginosa isolated from cystic fibrosis patients. J. Antimicrob. Chemother. 2005, 55 (2), 269-271.
Nazarenko et al., A closed tube format for amplification and detection of DNA based on energy transfer. Nucleic Acids Res. 1997, 25 (12), 2516-2521.
Nunnally et al., Characterization of visible dyes for four-decay fluorescence detection in DNA sequencing. Anal. Chem. 1997, 69 (13), 2392-2397.
Okawa et al., Binuclear metal complexes. V. Template synthesis of a binuclear copper(II) complex of a macrocycle containing amino groups. Chem. Lett. 1972, 10, 1027-1030.
Ost, H., Synthese mehrbasischer Säuren aus Salicylsäure und Kohlensäure. J. Prakt. Chem. 1876, 14 (1), 93-124.
Petoud et al., Stable Lanthanide Luminescence Agents Highly Emissive in Aqueous Solution: Multidentate 2-Hydroxyisophthalamide Complexes of Sm3+, Eu3+, Tb3+, Dy3+. J. Am. Chem. Soc. 2003, 125 (44), 13324-13325.
Pierre et al., Substituent effects on Gd(III)-based MRI contrast agents: optimizing the stability and selectivity of the complex and the number of coordinated water molecules. Inorg. Chem. 2006, 45 (20), 8355-8364.
Poole et al., Synthesis and characterisation of highly emissive and kinetically stable lanthanide complexes suitable for usage "in cellulo". Org. Biomol. Chem. 2005, 3 (6), 1013-1024.
Prober et al., A System for Rapid DNA Sequencing with Fluorescent Chain-Terminating Dideoxynucleotides. Science 1987, 238 (4825), 336-341.
Puerta et al., Tris(pyrone) Chelates of Gd(III) as High Solubility MRI-CA. J. Am. Chem. Soc. 2006, 128 (7), 2222-2223.
Rajapakse et al., Luminescent Terbium Protein Labels for Time-Resolved Microscopy and Screening. Angew. Chem. Int. Ed. Engl. 2009, 48 (27), 4990-4992.
Raymond and Pierre, Next Generation, High Relaxivity Gadolinium MRI Agents. Bioconjug. Chem. 2005, 16 (1), 3-8.
Riehl and Richardson, Circularly Polarized Luminescence Spectroscopy. Chem. Rev. 1986, 86 (1), 1-16.
Ruparel et al., Design and synthesis of a 3'-O-allyl photocleavable fluorescent nucleotide as a reversible terminator for DNA sequencing by synthesis. Proc. Natl. Acad. Sci. U.S.A. 2005, 102 (17), 5932-5937.
Sabbatini et al., Luminescent lanthanide complexes as photochemical supramolecular devices. Coord. Chem. Rev. 1993, 123 (1), 201-228.
Saha et al., Time-resolved fluorescence new europium chelate complex: Demonstration of highly sensitive detection of protein and DNA samples. J. Am. Chem. Soc. 1993, 115 (23), 11032-11033.
Scarrow et al., Ferric ion sequestering agents. 14. 1-Hydroxy-2(1H)-pyridinone complexes: properties and structure of a novel iron-iron dimer. J. Am. Chem. Soc. 1985, 107 (23), 6540-6546.
Schoket et al., Increased sensitivity for determination of polycyclic aromatic hydrocarbon-DNA adducts in human DNA samples by dissociation-enhanced lanthanide fluoroimmunoassay (DELFIA). Cancer Epidemiol. Biomarkers Prev. 1993, 2 (4), 349-353.
Selvin, P. R., Principles and biophysical applications of lanthanide-based probes. Annu. Rev. Biophys. Biomol. Struct. 2002, 31, 275-302.
Selvin, P., Fluorescence Resonance Energy Transfer. Methods Enzymol. 1995, 246, 300-334.
Seo et al., Four-color DNA sequencing by synthesis on a chip using photocleavable fluorescent nucleotides. Proc. Natl. Acad. Sci. U.S. A. 2005. 102 (17), 5926-5931.
Sequoia, E., Complexes of Lanthanide Perchlorates. Inorganica Chim. Acta 1979, 37 (1), L-449-L451.
Smith et al., Fluorescence detection in automated DNA sequence analysis. Nature 1986, 321 (6071), 674-679.
Soini et al., Time-resolved fluorescence of lanthanide probes and applications in biotechnology. CRC Crit. Rev. Anal. Chem. 1987, 18 (2), 105-154.
Soulere et al., Selective Inhibition of Fe-versus Cu/Zn-Superoxide Dismutases by 2,3-Dihydrosybenzoic Acid Derivavtives. Chem. Pharm. Bull. (Tokyo) 2002, 50 (5), 578-582.
Southwood-Jones et al. Oxygen-17 NMR and EPR studies of water exchange from the first coordination sphere of gadolinium(III) aquoion and gadolinium(III) propylenediaminetetra-acetate. J. Chem. Phys. 1980, 73 (12), 5909-5918.
Stack et al. Rational reduction of the conformational space of a siderophore analog through nonbonded interactions: the role of entropy in enterobactin. J. Am. Chem. Soc. 1993, 115 (14), 6466-6467.
Steemers et al. Water-soluble neutral calix[4]arene-lanthanide complexes: Synthesis and luminescence properties. J. Org. Chem. 1997, 62 (13), 4229-4235.
Steinberg, I., Long-Range Nonradiative Transfer of Electronic Excitation Energy in Proteins and Polypeptides. Annu. Rev. Biochem. 1971, 40, 83-114.
Stenroos et al., Homogeneous time-resolved IL-21L-R.alpha. assay using fluorescence resonance energy transfer. Cytokine 1998, 10 (7), 495-499.
Streater et al., Novel 3-hydroxy-2(1H)-pyridinones. Synthesis, Iron(III)-Chelating Properties, and Biological Activity. J. Med. Chem. 1990, 33 (6), 1749-1755.
Stryer, L., Fluorescence Energy Transfer as a Spectroscopic Ruler. Ann. Rev. Biochem. 1978, 47, 819-846.
Sunderland et al., 6-Carboxamido-5, 4-Hydroxypyrimidinones: A New Class of Heterocyclic Ligands and Their Evaluation as Gadolinium Chelating Agents. Inorg. Chem. 2001, 40 (26), 6746-6756.
Syvanen et al., Time-resolved fluorometry: a sensitive method to quantify DNA-hybrids. Nucleic Acids Res. 1986, 14 (2), 1017-1028.
Takalo et al., Synthesis of europium(III) chelates suitable for labeling of bioactive molecules. Bioconjug. Chem. 1994, 5 (3), 278-282.
Tedeschi et al. A solid-state study of eight-coordinate lanthanide(III) complexes (Ln=Eu, Gd, Tb, Dy) with 1-hydroxy-2-pyridinone. Dalton Trans. 2003, 9, 1738-1745.
Tsien, R. Y., The Green Fluorescent Protein. Annu. Rev. Biochem. 1998, 67, 509-544.
Tyagi et al., Molecular Beacons: Probes that Fluoresce upon Hybridization. Nat. Biotechnol. 1996, 14 (3), 303-308.

(56) References Cited

OTHER PUBLICATIONS

Tyagi et al., Multicolor molecular beacons for allele discrimination. Nat. Biotechnol. 1998, 16 (1), 49-53.

Uhlir et al., Specific Agents for the Actinides. 21. Synthesis and Initial Biological Testing of Octadentate Mixed Catecholate-Hydroxypridinoate Ligands. J. Med. Chem. 1993, 36 (4), 504-509.

Uhlir, L. C., Mixed Functionality Actinide Sequestering Agents. Ph.D. Thesis, University of California, Berkeley, CA, 1992.

Ullman et al., Fluorescent excitation transfer immunoassay. A general method for determination of antigens. J. Biol. Chem. 1976, 251 (14), 4172-4178.

Unger et al., Gadolinium-containing copolymeric chelates-a new potential MR contrast agent. Magn. Reson. Mater. Phys., Biol. Med. 1999, 8 (3), 154-162.

Vander Elst et al., Stereospecific binding of MRI contrast agents to human serum albumin: the case of Gd-(S)- EOB-DTPA (Eovist) and its (R) isomer. J. Biol. Inorg. Chem. 2001, 6 (2), 196-200.

Veiopoulou et al., Comparative study of fluorescent ternary terbium complexes. Application in enzyme amplified fluorimetric immunoassay for .alpha.-fetoprotein. Anal. Chim. Acta 1996, 335 (1-2), 177-184.

Vereb et al., Temporally and Spectrally Resolved Imaging Microscopy of Lanthanide Chelates. Biophys. J. 1998, 74 (5), 2210-2222.

Vicentini et al., Luminescence and structure of europium compounds. Coord. Chem. Rev. 2000, 196 (1), 353-382.

Villa et al., Force Field Parametrization for Gadolinium Complexes Based on ab Initio Potential Energy Surface Calculations. J. Phys. Chem. A 2000, 104 (15), 3421-3429.

Voss et al., Direct genomic fluorescent on-line sequencing and analysis using in vivo amplification of DNA. Nucleic Acids Res. 1989, 17 (7), 2517-2527.

Wagnon and Jackels, Synthesis, characterization, and aqueous proton relaxation enhancement of a manganese(II) heptaaza macrocyclic complex having pendant arms. Inorg. Chem. 1989, 28 (10), 1923-1927.

Wang et al., Design and Synthesis of New Fluorogenic HIV Protease Substrates Based on Resonance Energy Transfer. Tetrahedron Lett. 1990, 31 (45), 6493-6496.

Wang et al., Rapid Sizing of Short Tandem Repeat Alleles Using Capillary Array Electrophoresis and Energy-Transfer Fluorescent Primers. Anal. Chem. 1995, 67 (7), 1197-1203.

Wang et al., Unnatural Amino Acid Mutagenesis of Green Fluorescent Protein. J. Org. Chem. 2003, 68 (1), 174-176.

Weibel et al., Engineering of highly luminescent lanthanide tags suitable for protein labeling and time-resolved luminescence imaging. J. Am. Chem. Soc. 2004, 126 (15), 4888-4896.

Werner et al., Highly Soluble Tris-hydroxypyridonate Gd(III) Complexes with Increased Hydration Number, Fast Water Exchange, Slow Electronic Relaxation, and High Relaxivity. J. Am. Chem. Soc. 2007, 129 (7), 1870-1871.

Whitcombe et al., Detection of PCR products using self-probing amplicons and fluorescence. Nat. Biotechnol. 1999, 17 (8), 804-807.

White et al., Specific Sequestering Agents for the Actinides. 16. Synthesis and Initial Bioological Testing of Polydentate Oxohydroxypyridinecarboxylate Ligands. J. Med. Chem. 1988, 31 (1), 11-18.

Xiao and Selvin, Quantum yields of luminescent lanthanide chelates and far-red dyes measured by resonance energy transfer. J. Am. Chem. Soc. 2001, 123 (29), 7067-7073.

Xu et al., Gadolinium (III) 1,2-hydroxypyridonate-based complexes: toward MRI contrast agents of high relaxivity. Inorg. Chem. 2004, 43 (18), 5492-5494.

Xu et al., Gadolinium complex of tris[(3-hydroxy-1-methy1-2-oxo-1,2-didehydropyridine-4-carboxamido)ethyl]—amine: A new class of gadolinium magnetic resonance relaxation agents. J. Am. Chem. Soc. 1995, 117 (27), 7245-7246.

Xu et al., Gadolinium(III) 1,2-hydroxypyridonate-based complexes: toward MRI contrast agents of high relaxivity. Inorg. Chem. 2004, 43 (18), 5492-5494.

Xu et al., Plutonium(IV) Sequestration: Structural and Thermodynamic Evaluation of the Extraordinarily Stable Cerium(IV) Hydroxypyridinonate Complexes. Inorg. Chem. 2000, 39 (18), 4156-4164.

Xu et al., Specific Sequestering Agents for the Actinides. 28. Synthesis and Initial Evaluation of Multidentate 4-Carbamoyl-3-hydroxy-1-methyl-2-(1H)-pyridinone Ligands for in Vivo Plutonium (IV) Chelation. J. Med. Chem. 1995, 38 (14), 2606-2614.

Yamada et al., Selective Modification of Asparatic Acid-101 in Lysozyme by Carbodiimide Reaction. Biochemistry. 1981, 20, 4836-4842.

Yue et al., Potentiometric and spectrophotometric determination of stabilities of the 1-hydroxy-2-pyridinone complexes of trivalent and divalent metal ions. Inorg. Chim. Acta 1993, 214 (1-2), 103-111.

\* cited by examiner

LUMINESCENT 1-HYDROXY-2-PYRIDINONE CHELATES OF LANTHANIDES

CROSS-REFERENCE TO RELATED APPLICATIONS

This application is a Continuation of U.S. patent application Ser. No. 12/373,275, filed Aug. 14, 2009, which is a National Stage Entry of International Application No. PCT/US2007/073185, filed Jul. 10, 2007, which claims priority from U.S. Provisional Patent Application No. 60/819,904, filed Jul. 10, 2006, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant Numbers HL069832 and DK057814 awarded by the National Institutes of Health and Contract Number DE-AC3-76SF00098 awarded by the Department of Energy. The government has certain rights in the invention.

FIELD OF THE INVENTION

This invention relates to lanthanide complexes, useful as luminescent markers, as well as methods utilizing the complexes of the invention.

BACKGROUND OF THE INVENTION

Luminescent metal complexes are valuable as probes and labels in a variety of applications such as diagnostic products and bioanalytical assay systems.

There is a continuing and expanding need for rapid, highly specific methods of detecting and quantifying chemical, biochemical and biological substances as analytes in research and diagnostic mixtures. Of particular value are methods for measuring small quantities of proteins, nucleic acids, peptides, pharmaceuticals, metabolites, microorganisms and other materials of diagnostic value. Examples of such materials include small molecular bioactive materials (e.g., narcotics and poisons, drugs administered for therapeutic purposes, hormones), pathogenic microorganisms and viruses, antibodies, and enzymes and nucleic acids, particularly those implicated in disease states.

The presence of a particular analyte can often be determined by binding methods that exploit the high degree of specificity, which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which has been attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

A wide variety of labels have been developed, each with particular advantages and disadvantages. For example, radioactive labels are quite versatile, and can be detected at very low concentrations, such labels are, however, expensive, hazardous, and their use requires sophisticated equipment and trained personnel. Thus, there is wide interest in non-radioactive labels, particularly in labels that are observable by spectrophotometric, spin resonance, and luminescence techniques, and reactive materials, such as enzymes that produce such molecules.

Labels that are detectable using fluorescence spectroscopy are of particular interest, because of the large number of such labels that are known in the art. Moreover, the literature is replete with syntheses of fluorescent labels that are derivatized to allow their facile attachment to other molecules, and many such fluorescent labels are commercially available.

In addition to being directly detected, many fluorescent labels operate to quench or amplify the fluorescence of an adjacent second fluorescent label. Because of its dependence on the distance and the magnitude of the interaction between the quencher and the fluorophore, the quenching of a fluorescent species provides a sensitive probe of molecular conformation and binding, or other, interactions. An excellent example of the use of fluorescent reporter quencher pairs is found in the detection and analysis of nucleic acids.

An alternative detection scheme, which is theoretically more sensitive than autoradiography, is time-resolved fluorimetry. According to this method, a chelated lanthanide metal with a long radiative lifetime is attached to a molecule of interest. Pulsed excitation combined with a gated detection system allows for effective discrimination against short-lived background emission. For example, using this approach, the detection and quantification of DNA hybrids via an europium-labeled antibody has been demonstrated (Syvanen et al., *Nucleic Acids Research* 14: 1017-1028 (1986)). In addition, biotinylated DNA was measured in microtiter wells using Eu-labeled streptavidin (Dahlen, *Anal. Biochem*, 164: 78-83 (1982)). A disadvantage, however, of these types of assays is that the label must be washed from the probe and its fluorescence developed in an enhancement solution. A further drawback has been the fact that the fluorescence produced has only been in the nanosecond (ns) range, a generally unacceptably short period for adequate detection of the labeled molecules and for discrimination from background fluorescence.

In view of the predictable practical advantages it has been generally desired that the lanthanide chelates employed should exhibit a delayed luminescence with decay times of more than 10 µs. The fluorescence of many of the known fluorescent chelates tends to be inhibited by water and require augmentation with e.g. fluoride or micelles. As water is generally present in an assay, particularly an immunoassay system, lanthanide complexes that undergo inhibition of fluorescence in the presence of water are viewed as somewhat unfavorable or impractical for many applications. Moreover, the short fluorescence decay times is considered a disadvantage of these compounds. This inhibition is due to the affinity of the lanthanide ions for coordinating water molecules. When the lanthanide ion has coordinated water molecules, the absorbed light energy (excitation energy) is transferred from the complex to the solvent rather than being emitted as fluorescence.

Thus, stable lanthanide chelates, particularly coordinatively saturated chelates having excellent luminescence properties are highly desirable. In the alternative, coordinatively unsaturated lanthanide chelates that exhibit acceptable luminescence in the presence of water are also advantageous. Such chelates that are derivatized to allow their conjugation to one or more components of an assay, find use in a range of different assay formats. The present invention provides these and other such compounds and assays using these compounds.

Derivatives of 1-hydroxy-2-pyridinone (Structure 1) are of particular interest, since the ligand and its mono-anion (Structure 2) have a zwitterionic resonance form (Structure 3) that is isoelectronic with the catechol dianion.

Further, the 1-hydroxy-2-pyridinone structure possesses synthetic advantages, since the 6-carboxylic acid derivative (Structure 4) can be made in a straightforward manner.

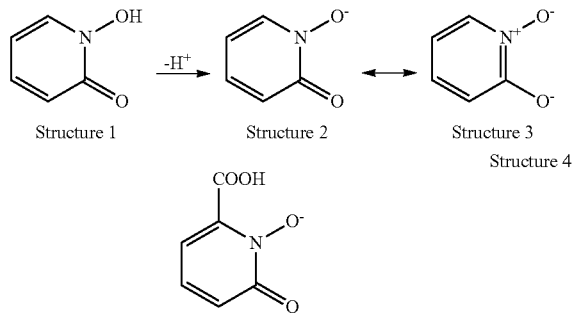

Structure 1    Structure 2    Structure 3

Structure 4

Since the 1,2-HOPO ligands are useful sequestering agents for hard metal ions, especially for the f-elements, effort has been directed towards improving the initial synthesis of complexing ligands based on 1,2-HOPO. The original synthesis of multidentate 1,2-HOPO ligands, reported a decade ago, involves several low yield steps, difficult purifications and the use of phosgene (White et al., *J. Med. Chem.* 31: 11-18 (1988). The use of phosgene gas is undesirable for a number of reasons: the procedure is tedious; phosgene is highly toxic and volatile; the yield of the amine conjugate is low (e.g., yields of 3,4-LI-1,2-HOPO, and 3,4,3-LI-1,2-HOPO using phosgene were 34% and 15%, respectively); and the separation of the resulting product is difficult, often requiring the use of HPLC.

Uhlir reported that, following benzyl protection of the N-hydroxyl group of 6-carboxy-1,2-HOPO, this protected species could be activated and coupled to an amine scaffold (Uhlir, L. C. MIXED FUNCTIONALITY ACTINIDE SEQUESTERING AGENTS. Ph.D. thesis, University of California, Berkeley, 1992). Uhlir activated the HOPO carboxyl group using NHS/DCC and HOBT/DCC (see, Bodansky, M.; Bodanszky, A., THE PRACTICE OF PEPTIDE SYNTHESIS 2nd Ed., Springer-Verlag Berlin Heidelberg 1994, pp 96-125). Uhlir did not disclose the formation of an acid halide from the benzyl protected HOPO derivative.

Bailly et al. reported the multistep preparation of a benzyl protected 1,2-HOPO acid chloride and the use of the protected acid chloride to form amine conjugates of 1,2-HOPO (*C. R. Acad. Sci. Paris* 1, Serie II: 241-245 (1998)). The procedure of Bailly et al. is cumbersome, requiring conversion of the carboxylic acid to the corresponding methyl ester, activation and protection of the N-hydroxyl group, saponification of the methyl ester, followed by the activation of the carboxylic acid as the acid chloride. Bailly et al. does not suggest that the hydroxyl group can be protected in the presence of the free acid at the 6-position.

Other related art includes U.S. Pat. No. 4,698,431, which discloses polyvalent 1,2-HOPO chelators having an amide or a carboxylic acid moiety in the 6-position. The chelating agents are useful in selectively removing certain cations from solution and are particularly useful as ferric ion and actinide chelators. U.S. Pat. No. 5,892,029 and U.S. Pat. No. 5,624,901 also set forth polyvalent 1,2-HOPO chelators. None of the patents discloses or suggests preparing a polyvalent chelator from a protected, acid halide intermediate.

U.S. Pat. No. 4,666,927, discloses a number of chelating agents having 1,2-HOPO, 3,2-HOPO, or 3,4-HOPO moieties incorporated within their structures that are linked through a number of possible combinations of linking groups, including —CONH— groups. However, U.S. Pat. No. 4,666,927 teaches against a HOPO moiety having a substitution ortho to the hydroxy or oxo group of the HOPO ring, and does not disclose or suggest an acyl halide 1,2-HOPO intermediate.

A need for luminescent complexes, which are stable under biological relevant conditions and at low concentrations, remains. The current invention addresses these and other needs.

BRIEF SUMMARY OF THE INVENTION

The present invention is directed toward new classes of chelating agents and metal complexes formed with these chelating agents. The invention is exemplified by reference to the use of the chelating agents to complex lanthanide metal ions, particularly those lanthanide ions, which, when complexed by a chelating agent of the invention form a luminescent lanthanide chelate. The luminescent metal chelates incorporating a pyridinone, particularly a hydroxypyridinone subunit. An exemplary hydroxy-pyridinone subunit is 1-hydroxy-2-pyridinone. The invention provides luminescent complexes formed between lanthanides, e.g., $Tb^{+3}$ and $Eu^{+3}$, and organic ligands that incorporate 1-hydroxy-2-pyridinone subunits as chelating agents. Also provided are complexes formed between actinides (e.g., ions of elements 89-103) and a chelating agent of the invention.

Luminescent (including fluorescent, phosphorescent and emission arising from metal ions) markers find a wide variety of applications in science, medicine and engineering. In many situations, these markers or probes provide competitive replacements for radiolabels, chromogens, radiation-dense dyes, etc. Moreover, improvements in fluorometric instrumentation have increased attainable sensitivities and permitted quantitative analysis.

Lanthanide chelates in combination with time-resolved fluorescent spectroscopy is a widely used analytical, e.g., immunochemical tool. Lanthanide ions generally utilized in analytical procedures include $Dy^{3+}$, $Sm^{3+}$, $Tb^{3+}$, $Er^{3+}$ and $Eu^{3+}$, $Nd^{3+}$, $Tm^{3+}$, $Yb^{3+}$. Other lanthanide ions, such as $La^{3+}$, $Gd^{3+}$ and $Lu^{3+}$ are useful as well.

The present invention provides luminescent lanthanide complexes that possess many features desired for luminescent markers and probes of use in fluorescent assay systems. Among these advantages are: 1) ligands acting as both chelators and chromophore/energy transfer devices; 2) high quantum yields of lanthanide ion luminescence of the present complexes in water without external augmentation, such as by micelles or fluoride; 3) high stability and solubility of these complexes in water; 4) straight forward syntheses employing inexpensive starting materials; and 5) facile access to many derivatives for linking these luminescent probes to, for example, an immunoreactive agent or solid support (e.g., polymer).

Unexpectedly, the inventors have discovered that chelates formed between a lanthanide ion and one or more organic ligands, incorporating a 1-hydroxy-2-pyridinone (1,2-HOPO) subunit, are luminescent and exhibit superior stability in aqueous solutions, including those with low pH. Moreover, these ligands complex actinides to form highly stable actinide ion complexes.

Thus, in one aspect, the invention provides a luminescent complex between a lanthanide ion and an organic ligand comprising the subunit of Formula I:

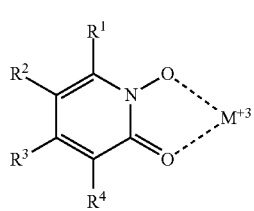

(I)

wherein $R^1$, $R^2$, $R^3$ and $R^4$ are members independently selected from H, an aryl group substituent defined herein, a linker to a scaffold moiety and a linker to a functional moiety. $M^{+3}$ is a metal ion, e.g., an actinide ion or a lanthanide ion, preferably forming the luminescent complex with one or more organic ligands.

Other objects and advantages of the present invention are apparent from the detailed description below.

DETAILED DESCRIPTION OF THE INVENTION

1. Introduction

The present invention provides a class of chelating agents of use to chelate metal ions, e.g., actinides and lanthanides, and are particularly preferred to form luminescent probes. The chelating agents of the invention are based on 1,2-hydroxypyridinone-based ligands ("1,2-HOPO"). Exemplary chelating agents (and metal ion complexes) of the invention include 1,2-HOPO and other chelating moieties, e.g., maltol derivatives, hydroxypyrimidinone (HOPY) derivatives, hydroxy-iso-phthalic acid derivatives, catecholic acid derivatives, terephthalic acid derivatives (e.g., terephthalamidyl, TAM) and salicylic acid derivatives, preferably incorporated into a single ligand in which the subunits are linked by a scaffold moiety, e.g., tris(2-aminoethyl) amine (TREN) and, preferably octadentate topology scaffolds, such as H22.

Selected complexes of the invention emit light or they can be used to absorb light emitted by a reporter fluorophore. The fluorophores of the invention can be used as small molecules in solution assays or they can be utilized as a label that is attached to an analyte or a species that interacts with, and allows detection and/or quantification of an analyte.

Luminescent (e.g., fluorescent) labels have the advantage of requiring few precautions in their handling, and being amenable to high-throughput visualization techniques (optical analysis including digitization of the image for analysis in an integrated system comprising a computer). Preferred labels are typically characterized by high sensitivity, high stability, low background, long lifetimes, low environmental sensitivity and high specificity in labeling.

The fluorophores of the invention can also be used in conjunction with other fluorophores or quenchers as components of energy transfer probes. Many fluorescent labels are useful in combination with the chelators of the invention. Many such labels are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful with the complexes of the present invention. Such proteins include, for example, green fluorescent proteins of cnidarians (Ward et al., *Photochem. Photobiol.* 35:803-808 (1982); Levine et al., *Comp. Biochem. Physiol.*, 72B:77-85 (1982)), yellow fluorescent protein from *Vibrio fischeri* strain (Baldwin et al., *Biochemistry* 29:5509-15 (1990)), Peridinin-chlorophyll from the dinoflagellate Symbiodinium sp. (Morris et al., *Plant Molecular Biology* 24:673:77 (1994)), phycobiliproteins from marine cyanobacteria, such as Synechococcus, e.g., phycoerythrin and phycocyanin (Wilbanks et al., *J. Biol. Chem.* 268:1226-35 (1993)), and the like.

The compounds of the invention can be used as probes, as tools for separating particular ions from other solutes, as probes in microscopy, enzymology, clinical chemistry, molecular biology and medicine. The compounds of the invention are also useful as therapeutic agents in modalities, such as photodynamic therapy and as diagnostic agents in imaging methods. Moreover, the compounds of the invention are useful as components of optical amplifiers of light, waveguides and the like. Furthermore, the compounds of the invention can be incorporated into inks and dyes, such as those used in the printing of currency or other negotiable instruments.

The complexes of the invention emit fluorescence upon excitation using any manner known in the art, including, for example, with light or electrochemical energy (see, for example, Kulmala et al, *Analytica Chimica Acta* 386: 1 (1999)). The luminescence can, in the case of chiral compounds of the invention, be circularly polarized (see, for example, Riehl et al., *Chem. Rev.* 86: 1 (1986)).

The chelating agents and their metal ion complexes, e.g., luminescent complexes, and methods discussed in the following sections are generally representative of the compositions of the invention and the methods in which such compositions can be used. Many of the chelating agents are shown in the sections that follow in their complexed form (e.g., complexed with $M^{+3}$). These formulae are not limited to the metal ion complexes, but merely recite one form of the chelating agent, i.e., complexed. The formulae are equally representative of the uncomplexed chelating agents, unless the chelating agent is designated as being complexed with a specific metal ion or as having a specific property imparted to the complex by chelation of the metal ion (e.g., luminescence). The following discussion is intended as illustrative of selected aspects and embodiments of the present invention and it should not be interpreted as limiting the scope of the present invention.

2. Definitions

Unless defined otherwise, all technical and scientific terms used herein generally have the same meaning as commonly understood by one of ordinary skill in the art to which this invention belongs. Generally, the nomenclature used herein and the laboratory procedures in molecular biology, organic chemistry and nucleic acid chemistry and hybridization described below are those well known and commonly employed in the art. Standard techniques are used for nucleic acid and peptide synthesis. The nomenclature used herein and the laboratory procedures in analytical chemistry, and organic synthetic described below are those known and employed in the art. Standard techniques, or modifications thereof, are used for chemical syntheses and chemical analyses.

"Analyte", as used herein, means any compound or molecule of interest for which a diagnostic test is performed, such as a biopolymer or a small molecular bioactive material. An analyte can be, for example, a protein, peptide, a lipid, a carbohydrate, polysaccharide, glycoprotein, hormone, receptor, antigen, antibody, virus, substrate, metabolite, transition state analog, cofactor, inhibitor, drug, dye, nutrient, growth factor, lipid etc., without limitation.

As used herein, "energy transfer" refers to the process by which the light emission of a luminescent group is altered by a luminescence-modifying group. When the luminescence-modifying group is a quenching group then the light emission from the luminescent group is attenuated (quenched). Energy transfer mechanisms include luminescence resonance energy transfer by dipole-dipole interaction (e.g., in longer range energy transfer) or electron transfer (e.g., across shorter distances). While energy transfer is often based on spectral overlapping of the emission spectrum of the luminescent group and the absorption spectrum of the luminescence-modifying group, (in addition to distance between the groups) it has been demonstrated that spectral overlap is not necessarily required for energy transfer to occur (see e.g., Latva et al., U.S. Pat. No. 5,998,146, which is incorporated by reference in its entirety). It is to be understood that any reference to "energy transfer" in the instant application encompasses all mechanistically-distinct phenomena.

"Energy transfer pair" is used to refer to a group of molecules that participate in energy transfer. Such complexes may comprise, for example, two luminescent groups, which may be different from one-another and one quenching group, two quenching groups and one luminescent group, or multiple luminescent groups and multiple quenching groups. In cases where there are multiple luminescent groups and/or multiple quenching groups, the individual groups may be different from one another. Typically, one of the molecules acts as a luminescent group, and another acts as a luminescence-modifying group. The preferred energy transfer pair of the invention comprises a luminescent group and a quenching group of the invention. There is no limitation on the identity of the individual members of the energy transfer pair in this application. All that is required is that the spectroscopic properties of the energy transfer pair as a whole change in some measurable way if the distance between the individual members is altered by some critical amount.

As used herein, "luminescence-modifying group" refers to a molecule of the invention that can alter in any way the luminescence emission from a luminescent group. A luminescence-modifying group generally accomplishes this through an energy transfer mechanism. Depending on the identity of the luminescence-modifying group, the luminescence emission can undergo a number of alterations, including, but not limited to, attenuation, complete quenching, enhancement, a shift in wavelength, a shift in polarity, and a change in luminescence lifetime. One example of a luminescence-modifying group is a fluorescence-modifying group. Another exemplary luminescence-modifying group is a quenching group.

As used herein, "quenching group" refers to any luminescence-modifying group of the invention that can attenuate at least partly the light emitted by a luminescent group. This attenuation is referred to herein as "quenching". Hence, excitation of the luminescent group in the presence of the quenching group leads to an emission signal that is less intense than expected, or even completely absent. Quenching typically occurs through energy transfer between the luminescent group and the quenching group.

"Fluorescence resonance energy transfer" or "FRET" is used interchangeably with FET, and refers to an energy transfer phenomenon in which the light emitted by an excited fluorescent group is absorbed at least partially by a fluorescence-modifying group of the invention. If the fluorescence-modifying group is a quenching group, then that group will preferably not radiate a substantial fraction of the absorbed light as light of a different wavelength, and will preferably dissipate it as heat. FRET depends on energy transfer between the fluorescent group and the fluorescence-modifying group. FRET also depends on the distance between the quenching group and the fluorescent group.

"Moiety" refers to a radical of a molecule that is attached to another portion of the molecule.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Modifications can also include 3' and 5' modifications such as capping with a fluorophore or another moiety.

"Peptide" refers to a polymer in which the monomers are amino acids and are joined together through amide bonds, alternatively referred to as a polypeptide. When the amino acids are alpha-amino acids, either the L-optical isomer or the D-optical isomer can be used. Additionally, unnatural amino acids, for example, beta.-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. The term "peptide" or "polypeptide", as used herein, refers to naturally occurring as well as synthetic peptides. In addition, peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

Where substituent groups are specified by their conventional chemical formulae, written from left to right, they optionally equally encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl" with the difference that the heteroalkyl group, in order to qualify as an alkyl group, is linked to the remainder of the molecule through a carbon atom. Alkyl groups that are limited to hydrocarbon groups are termed "homoalkyl".

The term "alkenyl" by itself or as part of another substituent is used in its conventional sense, and refers to a radical derived from an alkene, as exemplified, but not limited by, substituted or unsubstituted vinyl and substituted or unsubstituted propenyl. Typically, an alkenyl group will have from 1 to 24 carbon atoms, with those groups having from 1 to 10 carbon atoms being generally preferred.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. A "cycloalkyl" or "heterocycloalkyl" substituent may be attached to the remainder of the molecule directly or through a linker, wherein the linker is preferably alkylene. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) optionally includes both aryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") optionally include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro (C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted (C$_1$-C$_6$)alkyl.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si), boron (B) and phosphorus (P).

The symbol "R" is a general abbreviation that represents a substituent group, e.g., one that is selected from substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The terms "enantiomeric excess" and diastereomeric excess" are used interchangeably herein. Compounds with a single stereocenter are referred to as being present in "enantiomeric excess," those with at least two stereocenters are referred to as being present in "diastereomeric excess."

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds. ORGANIC FUNCTIONAL GROUP PREPARATIONS, Academic Press, San Diego, 1989).

"Non-covalent protein binding groups" are moieties that interact with an intact or denatured polypeptide in an associative manner. The interaction may be either reversible or irreversible in a biological milieu. The incorporation of a "non-covalent protein binding group" into a chelating agent or complex of the invention provides the agent or complex with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxylate, boronate, sulfate, sulfone, sulfonate, thiosulfate, and thiosulfonate.

As used herein, "linking member" or "linking moiety" refers to a covalent chemical bond that preferentially includes at least one heteroatom. Exemplary linking moieties include —C(O)NH—, —C(O)O—, —NH—, —S—, —O—, and the like.

The term "targeting moiety" is intended to mean any moiety attached to the complexes of the invention. The targeting moiety can be a small molecule, which is intended to include both non-peptides and peptides. The targeting group can also be a macromolecule, which includes saccharides, lectins, receptors, ligands for receptors, proteins such as BSA, antibodies, solid supports and so forth. The targeting group can also be a polymer, such as a plastic surface, a poly-ethyleneglycol derivative and the like.

The symbol ∿∿, whether utilized as a bond or displayed perpendicular to a bond indicates the point at which the displayed moiety is attached to the remainder of the molecule, solid support, etc.

3. Compositions

Chelating Agents and Complexes

In one embodiment, the invention provides organic ligand contains at least one 1-hydroxy-2-pyridinone (1,2-HOPO) subunit as a chelating moiety. The HOPO subunit is optionally covalently linked to a scaffold moiety. In an exemplary embodiment, the chelate complexes a lanthanide ion and forms a luminescent lanthanide complex of the invention. Alternatively, the metal ion is an actinide or other metal ion (e.g., transition metal ion).

Throughout this specification, the chelating subunits are exemplified as being complexed with a metal ion having a +3 charge. The chemical formulae showing this representation are intended to also encompass the unmetallated chelating agents as well as complexes in which the metal ion has a charge other than +3, e.g., $U^{6+}$ or $Pu^{4+}$.

The chelates and complexes of the invention can contain any number of "free chelating moieties" and "linked chelating moieties", wherein a "linked chelating moiety" is covalently linked to at least one other chelating moiety through a scaffold moiety and wherein a "free chelating moiety" is not covalently linked to another chelating moiety through a scaffold moiety.

In one exemplary embodiment, the complex of the invention is formed between a metal ion (e.g, a lanthanide ion or actinide ion) and one organic ligand having four or more chelating moieties that are linked through a scaffold moiety. In another exemplary embodiment, the complex is formed between a lanthanide ion and two organic ligands, wherein each organic ligand is composed of two chelating moieties that are covalently linked through a scaffold moiety. In yet another exemplary embodiment, the complex is formed utilizing an organic ligand containing two chelating moieties that are linked through a scaffold moiety as well as two "free chelating moieties". Other permutations of "linked-" and "free chelating moieties" are encompassed within the scope of the present invention.

In addition, the complexes between the metal ion and the organic ligands may be charged or uncharged. For instance, in those complexes wherein the overall electric charge is negative, the negative charge may be "offset" by a cation, such as a quaternary amine (e.g., $NMe_4^+$).

Preferred complexes of the invention include those in which the organic ligand complexes the metal ion through oxygen atoms. Even more preferred is a chelate that complexes metal ions only through oxygen atoms. A further preferred complex includes an organic ligand that has 8 donor oxygen atoms that are coordinated to the metal ion, e.g., lanthanide ion.

Currently preferred metal ions include, but are not limited to $Fe^{3+}$, $Gd^{3+}$, $Eu^{3+}$, $Tb^{3+}$. $Am^{3+}$, $Pu^{4+}$, $Np^{4+}$, $Np^{5+}$ and $U^{6+}$ ions.

In one embodiment, the present invention provides a metal complex, e.g., a luminescent complex between a metal ion, e.g., a lanthanide ion or actinide ion, and an organic ligand that includes a chelating moiety of Formula (I):

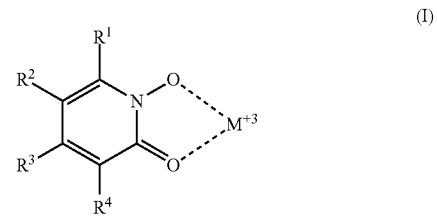

In Formula (I), $R^1$, $R^2$, $R^3$ and $R^4$ are members independently selected from H, an aryl group substituent as defined herein and a linker to a scaffold or functional moiety. $M^{+3}$ is metal ion, e.g., a lanthanide ion forming the complex, e.g., the luminescent complex, with the organic ligand.

The complexes of the invention can contain one or more chelating moieties, each optionally based on 1-hydroxy-2-pyridinone (1,2-HOPO) subunits of Formula (I).

In one exemplary embodiment, in Formula (I), $R^1$, $R^2$, $R^3$, and $R^4$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, halogen, CN, $CF_3$, —C(O)$R^{17}$, —SO$_2$N$R^{17}R^{18}$, —N$R^{17}R^{18}$, —O$R^{17}$, —S(O)$_2R^{17}$, —COO$R^{17}$, —S(O)$_2$O$R^{17}$, —OC(O)$R^{17}$, —C(O)N$R^{17}R^{18}$, —N$R^{17}$C(O)$R^{18}$, —N$R^{17}$SO$_2R^{18}$, —NO$_2$, a linker to a functional moiety and a linker to a scaffold moiety. At least two of $R^1$, $R^2$, $R^3$ and $R^4$ are optionally joined to form a ring system which is a member selected from substituted or unsubstituted cycloalkyl, substituted or unsubstituted heterocycloalkyl, substituted or unsubstituted aryl and substituted or unsubstituted heteroaryl. $R^{17}$ and $R^{18}$ are each members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, a linker to a functional moiety and a linker to a scaffold moiety. $R^{17}$ and $R^{18}$, together with the atoms to which they are attached, are optionally joined to form a 5- to 7-membered ring.

Exemplary linker moieties include a bond ("zero-order"), —C(O)N$R^5$—, —C(O)O—, —C(O)S—, and —C(O)C$R^{20}R^{21}$, wherein $R^5$, $R^{20}$ and $R^{21}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. Preferred linkers include $C_1$-$C_{10}$, preferably, $C_1$-$C_6$ substituted or unsubstituted alkyl or substituted or unsubstituted heteroalkyl moieties.

In one exemplary embodiment, the organic ligand is an amide derived from 1-hydroxy-2-pyridinone-6-carboxylic acid. Exemplary amides include those in which $R^1$ is —C(O) N$R^{17}R^{18}$. In another exemplary embodiment, $R^{17}$ is H and $R^{18}$ is substituted or unsubstituted alkyl. Two exemplary amides are shown below. Both the hexylamide and the decylamide showed strong luminescence under long-wave UV light when mixed with an aqueous solution of a lanthanide ion.

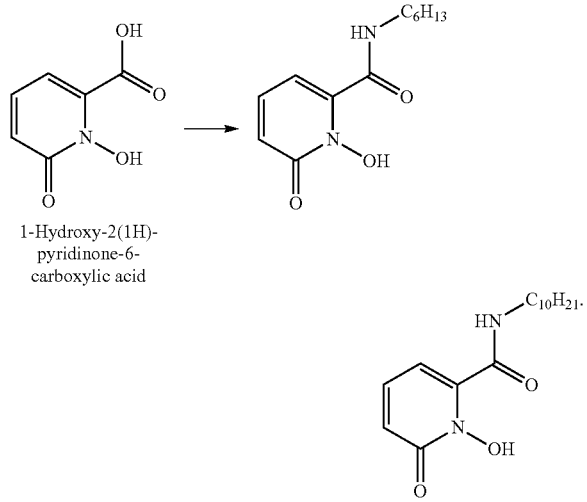

1-Hydroxy-2(1H)-pyridinone-6-carboxylic acid

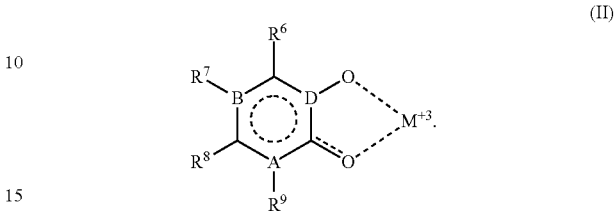

In another exemplary embodiment, the 1,2-HOPO subunit is covalently linked to a scaffold moiety and the chelating moiety of Formula (I) has the structure:

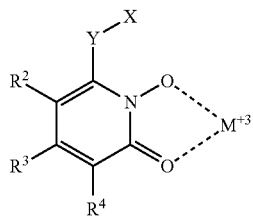

wherein X is a scaffold moiety, and Y is a linker moiety. Exemplary linker moieties include a bond ("zero-order"), —C(O)NR$^5$—, —C(O)O—, —C(O)S—, and -C(O)CR$^{20}$R$^{21}$, wherein R$^5$, R$^{20}$ and R$^{21}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

In yet another embodiment, the hydroxypyridinone subunit of the complex has the structure:

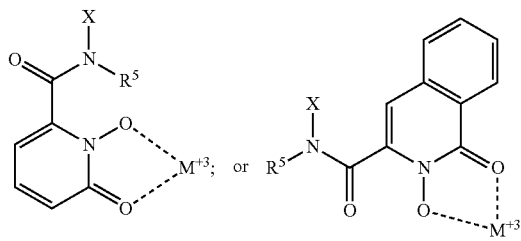

wherein X and R$^5$ are as defined above. The heterocycle or the aryl ring are optionally functionalized with one or more substituent defined herein as an "aryl group substituent" or an "alkyl group substituent."

In a further embodiment, the chelating agents and their complexes, e.g., luminescent complexes, of the invention contain one or more chelating moieties that, in addition to a 1,2-HOPO moiety, include a structure distinct from the 1,2-HOPO derivatives discussed above. In a preferred embodiment, each of those chelating moieties is independently selected from a structure according to Formula (II):

(II)

In Formula (II), the chelating agent is shown in the form of its complex. It will be apparent to those of skill in the art that Formula (II) also discloses the uncomplexed chelating agent. In one exemplary embodiment, in Formula (II), each R$^6$, R$^7$, R$^8$, and R$^9$ in each chelating moiety are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, halogen, CN, CF$_3$, —C(O)R$^{17}$, —SO$_2$NR$^{17}$R$^{18}$, —NR$^{17}$R$^{18}$, —OR$^{17}$, —S(O)$_2$R$^{17}$, —COOR$^{17}$, —S(O)$_2$OR$^{17}$, —OC(O)R$^{17}$, —C(O)NR$^{17}$R$^{18}$, —NR$^{17}$C(O)R$^{18}$, —NR$^{17}$SO$_2$R$^{18}$, —NO$_2$, a linker to a functional moiety, and a linker to a scaffold moiety. At least two of R$^6$, R$^7$, R$^8$ and R$^9$ are optionally joined to form a ring system which is a member selected from substituted or unsubstituted cycloalkyl, substituted or unsubstituted heterocycloalkyl, substituted or unsubstituted aryl and substituted or unsubstituted heteroaryl. R$^{17}$ and R$^{18}$ are each members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, a linker to a functional moiety and a linker to a scaffold moiety. R$^{17}$ and R$^{18}$, together with the atoms to which they are attached, are optionally joined to form a 5- to 7-membered ring.

A and B in Formula (II) are members independently selected from carbon, nitrogen, sulfur and oxygen. D is a member selected from carbon and nitrogen. If A is oxygen or sulfur, R$^9$ is preferably not present; and if B is oxygen or sulfur, R$^7$ is preferably not present.

The chelating moiety of Formula (II) is preferably not 3-hydroxy-2-pyridinone:

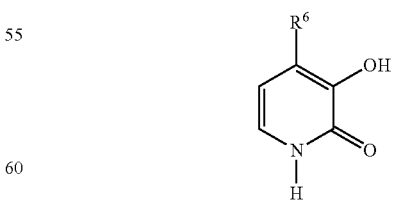

or this moiety complexed with a metal ion.

In one exemplary embodiment, the chelating moieties of Formula (II) are members independently selected from the following structures.

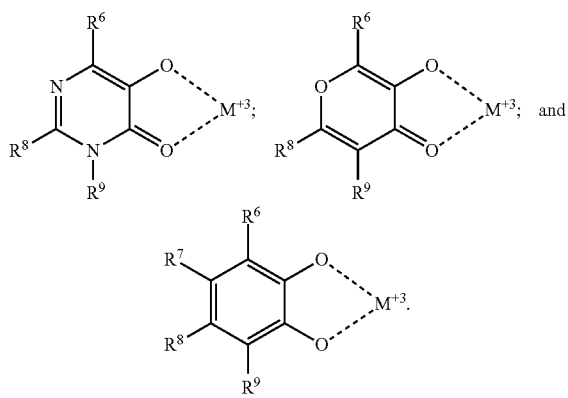

Similar to Formula (II), these structures should be interpreted as disclosing both the complexed and uncomplexed chelating agents. In another exemplary embodiment, $R^6$ in Formula (II) represents a linker to a scaffold moiety. Exemplary chelating moieties according to this aspect have the following structures:

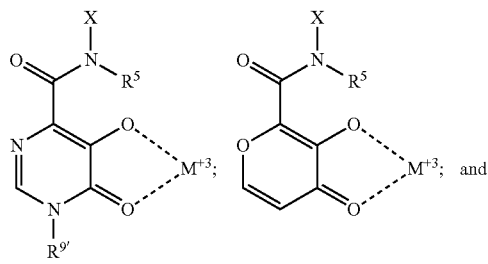

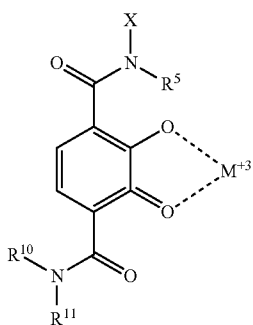

wherein X is a scaffold moiety. $R^5$ and $R^{10}$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl. $R^{11}$ is a member selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and a functional moiety. $R^{9'}$ in the pyrimidinone is a member selected from substituted or unsubstituted alkyl, substituted or unsubstituted heteroalkyl, substituted or unsubstituted aryl, substituted or unsubstituted heteroaryl, and substituted or unsubstituted heterocycloalkyl and is preferably a member selected from $C_1$-$C_6$ alkyl.

In one embodiment, two or more of the chelating moieties, which are independently selected from Formula (I) and Formula (II) can be covalently linked through a scaffold moiety. This is, for example, the case when at least one of $R^1$, $R^2$, $R^3$ and $R^4$ in Formula (I) is covalently linked to a scaffold moiety, wherein the scaffold moiety is covalently linked to at least one chelating moiety of Formula (II).

Thus, in an exemplary embodiment the luminescent complexes of the invention have a structure according to Formula (III):

(III)

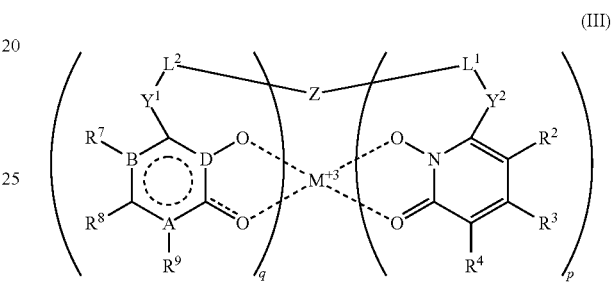

In Formula (III) Z is a member selected from substituted or unsubstituted alkyl, substituted or unsubstituted heteroalkyl, substituted or unsubstituted aryl, substituted or unsubstituted heteroaryl, substituted or unsubstituted heterocycloalkyl, N, $NR^{30}$, O and S. In an exemplary embodiment, Z is $CR^{31}R^{32}$. $R^{30}$, $R^{31}$ and $R^{32}$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl and a linker to a functional moiety. In another exemplary embodiment, Z is substituted with a chelating moiety. The integer p is selected from 1-3 and q is an integer selected from 0-2. The sum of p and q is preferably not greater than 4, and if Z is O or S, the sum of p and q is preferably 2. $Y^1$ and $Y^2$ are linker moieties. In one exemplary embodiment, each of $Y^1$ and $Y^2$ is a member independently selected from —C(O)$NR^5$—, —C(O)O—, —C(O)S—, and —C(O)$CR^{20}R^{21}$, wherein $R^5$, $R^{20}$ and $R^{21}$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl and a functional moiety.

$L^1$ and $L^2$ are linker groups, and each $L^1$ and $L^2$ is a member independently selected from a bond, substituted or unsubstituted alkyl, substituted or unsubstituted heteroalkyl, substituted or unsubstituted aryl, substituted or unsubstituted heteroaryl and substituted or unsubstituted heterocycloalkyl. At least one of Z, $Y^1$, $Y^2$, $L^1$ and $L^2$ is optionally substituted with a functional moiety. In an exemplary embodiment, Z is O and $L^1$ and $L^2$ are each ethyl.

In one exemplary embodiment, Z is $NR^{30}$ (e.g., when the sum of p and q is 2), wherein $R^{30}$ is a member selected from substituted or unsubstituted alkyl, substituted or unsubstituted heteroalkyl, substituted or unsubstituted aryl, substituted or unsubstituted heteroaryl, substituted or unsubstituted heterocycloalkyl and a linker to a functional moiety.

Tetradentate Ligands
In one embodiment, the organic ligand is a tetradentate ligand. Exemplary tetradentate ligands include:
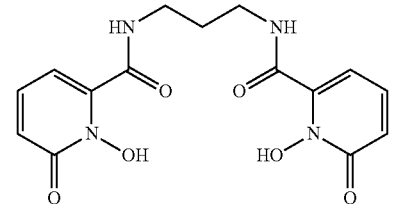
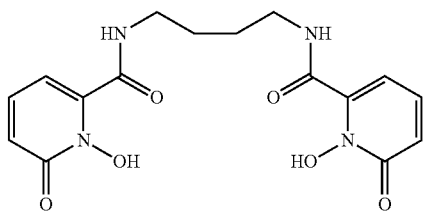
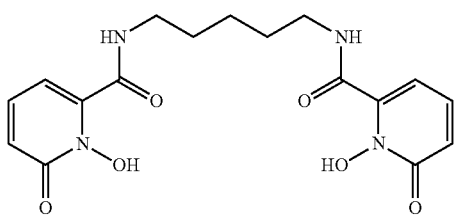
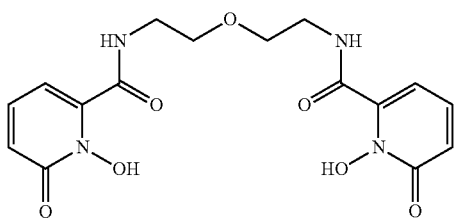
5LIO-1,2-HOPO
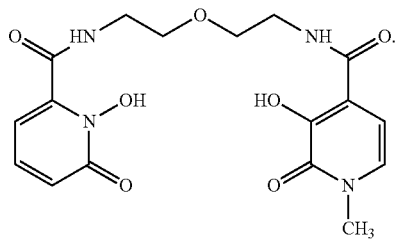
5LIO-1,2-Me-3,2-HOPO
Hexadentate Ligands
In another exemplary embodiment, the organic ligand is a hexadentate ligand. Exemplary hexadentate ligands include rigid and flexible structures:
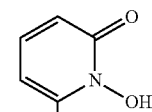
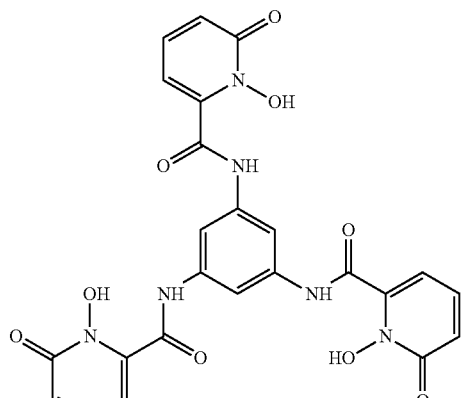
Benzene-1,3,5-tris-1,2-HOPO
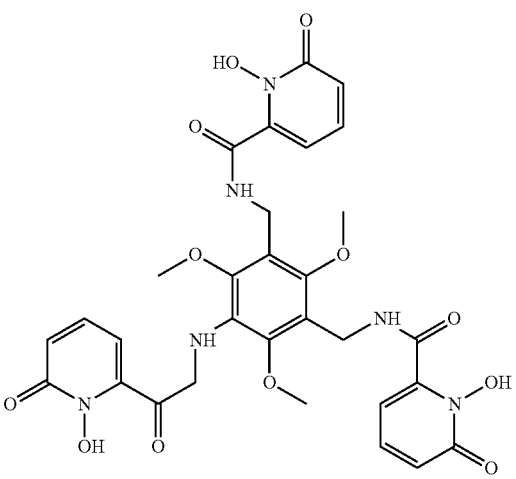
MeOMe-1,2-HOPO
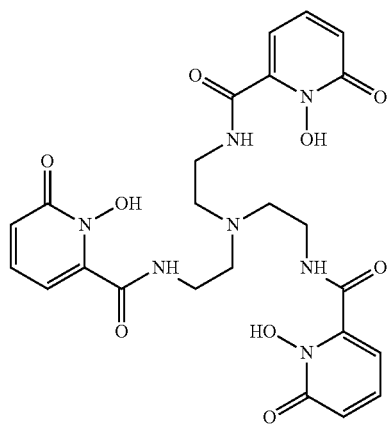
TREN-1,2-HOPO

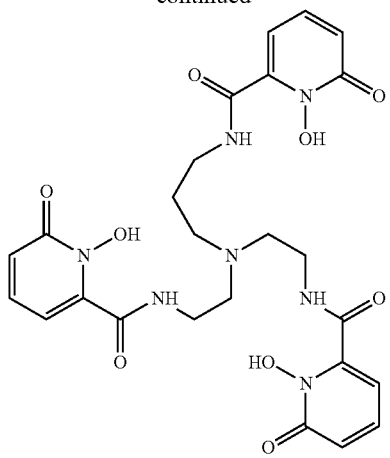

TR223-1,2-HOPO

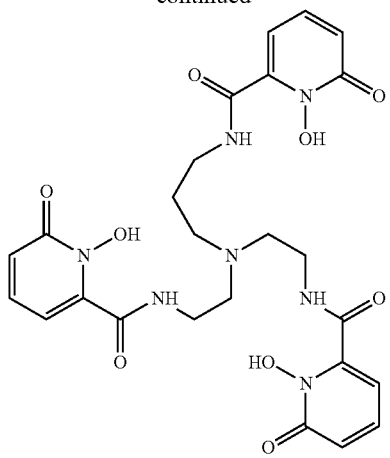

TR322-1,2-HOPO

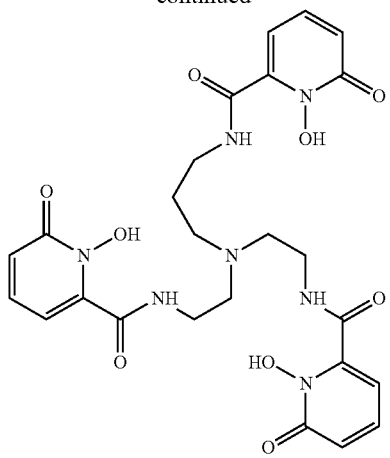

TRPN-1,2-HOPO

Octadentate Ligands

In another embodiment, the luminescent complex of the invention includes an octadentate ligand having a structure according to Formula (IV):

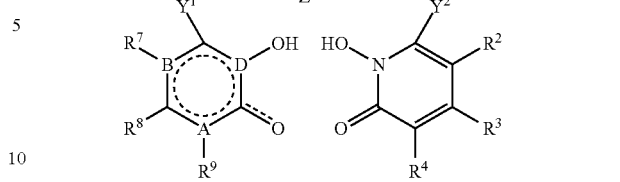

wherein Z, $L^1$, $L^2$, $Y^1$, $Y^2$, $R^2$, $R^3$, $R^4$, $R^7$, $R^8$, $R^9$, A, B and D are as defined above for Formula (I), Formula (II) and Formula (III). In Formula (IV) at least one of Z, $Y^1$, $Y^2$, $L^1$ and $L^2$ is substituted with a moiety having the structure:

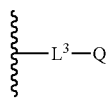

$L^3$ is a linker group, which is a member selected from a bond, substituted or unsubstituted alkyl, substituted or unsubstituted heteroalkyl, substituted or unsubstituted aryl, substituted or unsubstituted heteroaryl and substituted or unsubstituted heterocycloalkyl. In an exemplary embodiment $L^3$ is substituted with one or more groups that include a chelating moiety. In another embodiment, $L^3$ is chosen to increase the water solubility of the complex. Accordingly, in one example, $L^3$ includes an ether group or a polyether moiety. In a preferred embodiment, $L^3$ includes 2 to 10 linear atoms, and more preferably 2 to 8 linear atoms. Q has the structure of Formula (V):

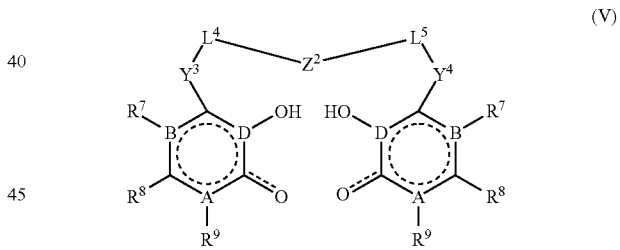

wherein $Z^2$ is a member selected from substituted or unsubstituted alkyl, substituted or unsubstituted heteroalkyl, substituted or unsubstituted aryl, substituted or unsubstituted heteroaryl, substituted or unsubstituted heterocycloalkyl, N, $NR^{30}$, O and S. In an exemplary embodiment, $Z^2$ is $CR^{31}R^{32}$. $R^{30}$, $R^{31}$ and $R^{32}$ are as defined above. In another exemplary embodiment, $Z^2$ is substituted with a chelating moiety. $Y^3$ and $Y^4$ are linker moieties, which are members independently selected from —C(O), —C(O)$NR^5$—, —C(O)O—, —C(O)S—, and —C(O)$CR^{20}R^{21}$, wherein $R^5$, $R^{20}$ and $R^{21}$ are as defined above. $L^4$ and $L^5$ are linker groups, which are members independently selected from a bond, substituted or unsubstituted alkyl, substituted or unsubstituted heteroalkyl, substituted or unsubstituted aryl, substituted or unsubstituted heteroaryl and substituted or unsubstituted heterocycloalkyl. In Formula (V), at least one of $Z^2$, $Y^3$, $Y^4$, $L^4$ and $L^5$ is linked to $L^3$. At least one of the chelating moieties of Formula (V) is preferably a 1,2-HOPO unit.

Exemplary octadentate ligands include those with linear as well as tetrapodal topology:
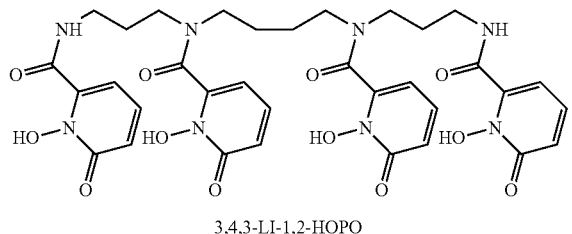
3,4,3-LI-1,2-HOPO
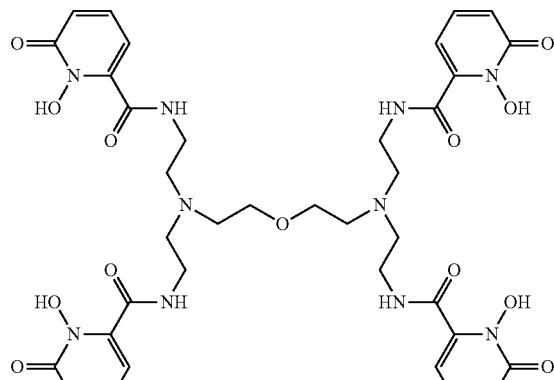
H(5O,2)-1,2-HOPO
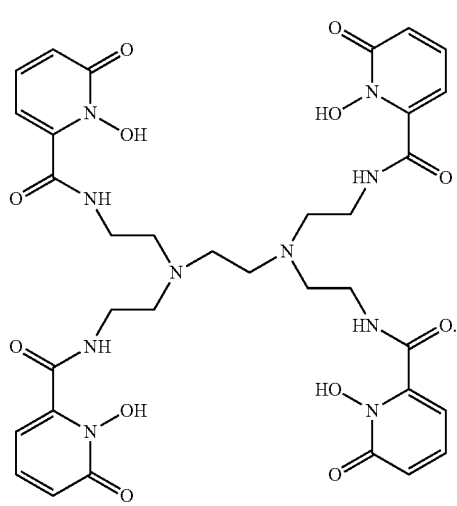
H(2,2)-1,2-HOPO
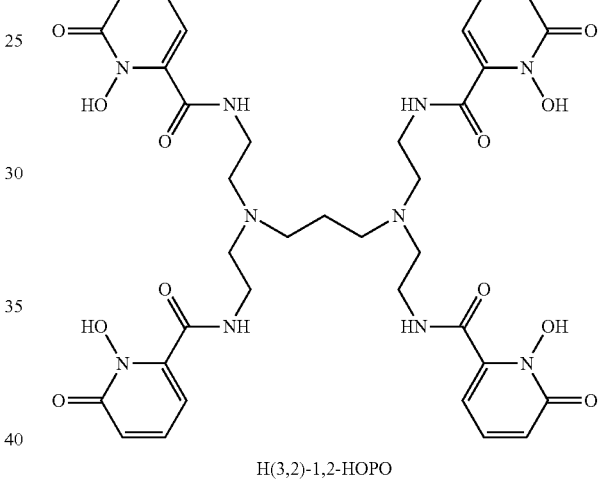
H(3,2)-1,2-HOPO
Other examples for ligands with tetrapodal topology include:
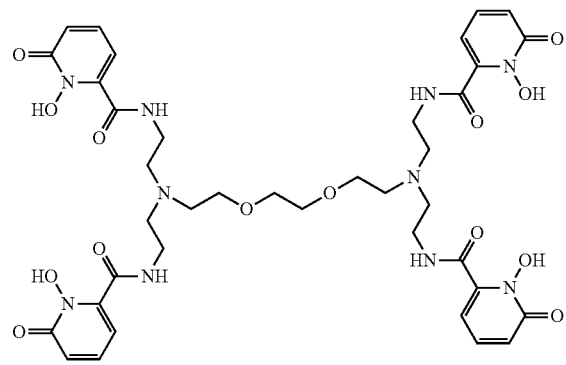
H(8O2,2)-1,2-HOPO
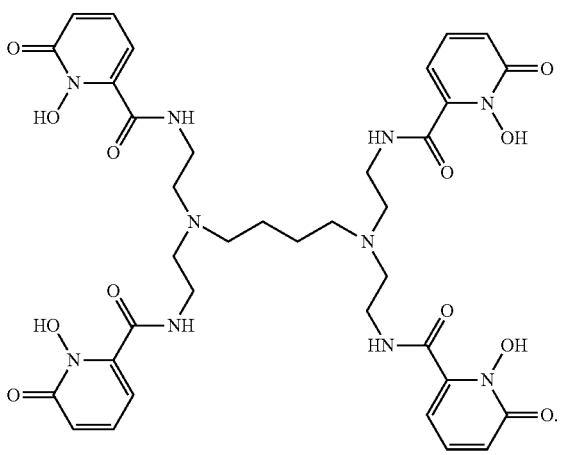
H(4,2)-1,2-HOPO $L^3$ can be positioned to link two sub-structures of a ligand in the center or "off-center", for instance as shown below:

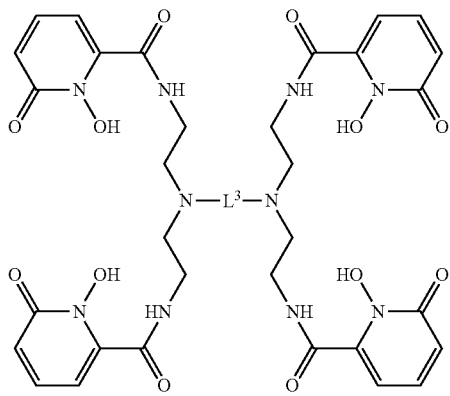

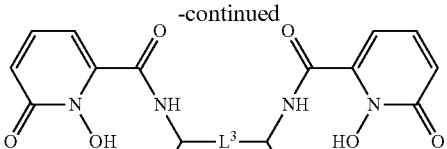

In an exemplary embodiment, the organic ligands of the invention can have higher than octadentate denticities. Those can, for example, be generated using scaffold moieties with more than four functional groups (e.g. $NH_2$ groups). In one example, additional chelating moieties are not used for chelation but instead may be used for protecting the central metal ion from water coordination.

Exemplary decadentate ligands include the following molecules, which also carry exemplary functional moieties:

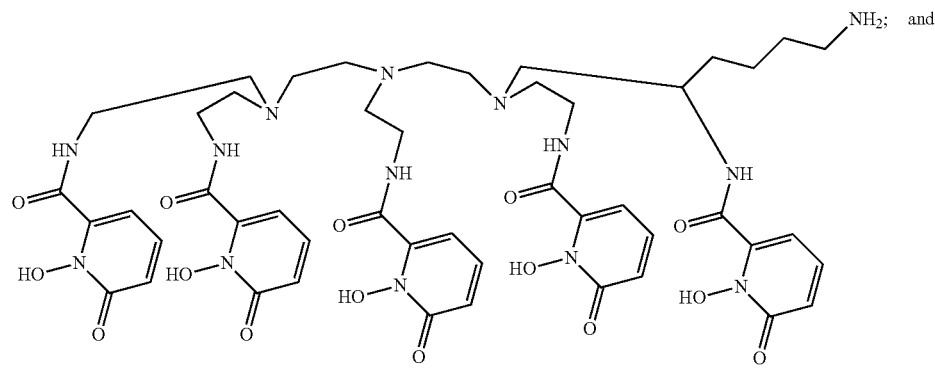

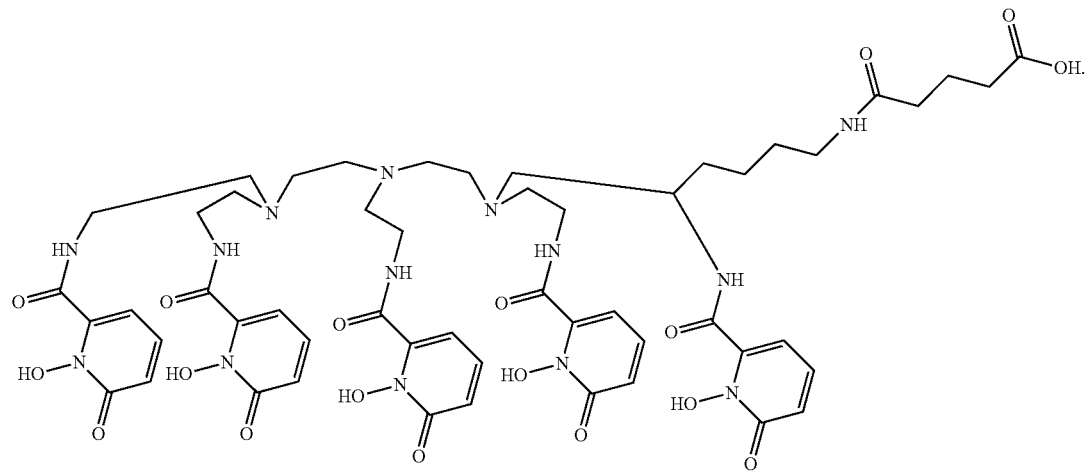

Scaffold Moiety

The scaffold moiety of the invention can be any moiety useful for covalently linking two or more chelating moieties. In one embodiment, the scaffold moiety is a member selected from substituted or unsubstituted alkyl and substituted or unsubstituted heteroalkyl. Exemplary scaffold moieties include linear or branched ethers and amines.

Other exemplary scaffolds include, but are not limited to:

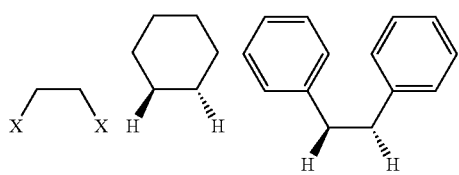

A generally preferred moiety for at least one of the X radicals is the 1,2-HOPO amide moiety shown above, however, those of skill in the art will appreciate that other chelating agents including, without limitation, a chelating moiety according to Formula (II) hereinabove. In each of the scaffold structures, and the 1,2-HOPO structure set forth above, the aryl moiety or alkyl moiety can be substituted with one or more "aryl group substituent" or "alkyl group substituent" as defined herein.

Other scaffold moieties that include functional moieties (or a linker to a functional moiety) include linkers prepared by the following exemplary methods.

Scheme 1.1 Reverse synthetic scheme for carboxyl functionalized H22 cap-amine.

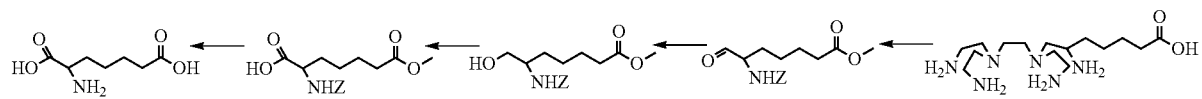

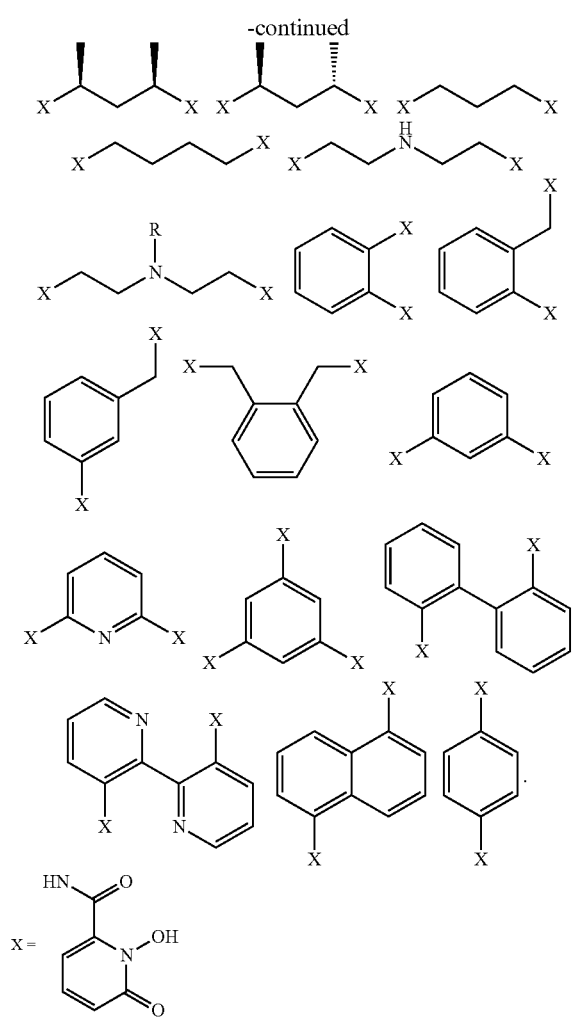

Other functionalize scaffolds include those in which the chiral carbon is placed on the central ethylene bridge of H22-amine. An exemplary route to such a scaffold initiates with 2,3-Diaminopropionic acid, as its carboxyl group is connected directly to the amine backbone to give a very rigid geometry, extended carboxyl chain is needed to provide flexibility for eventual protein conjugating. A synthetic scheme to the scaffold is shown in scheme 1.2.

Scheme 1.2

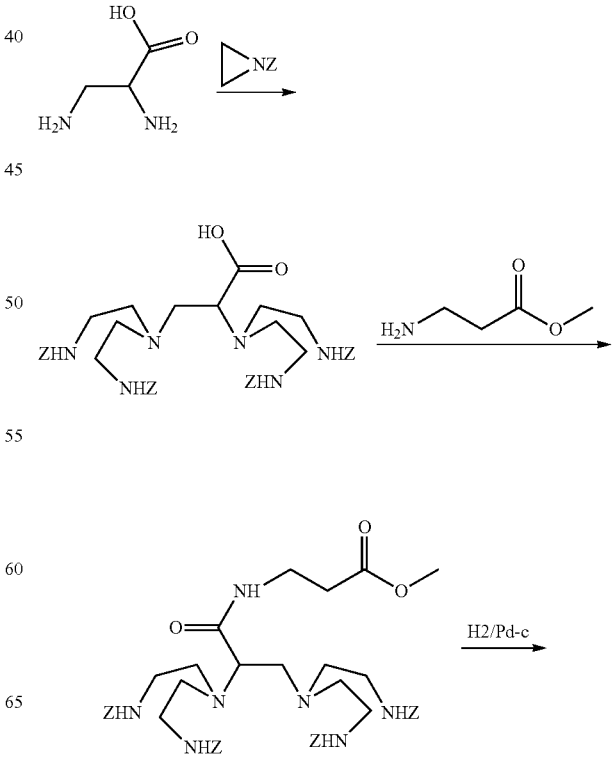

31
-continued
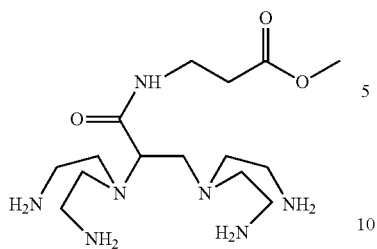
Variations on this synthesis include the use of a nitrophenylalanine or a BOC-amino group, which are optionally converted to carboxyl groups. Synthetic routes to these scaffolds are shown in Schemes 1.3 and 1.4.
32
-continued
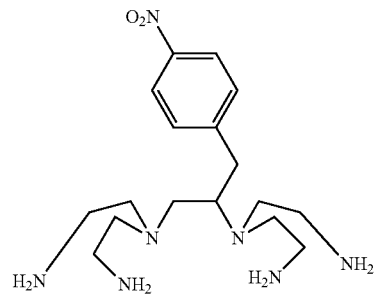
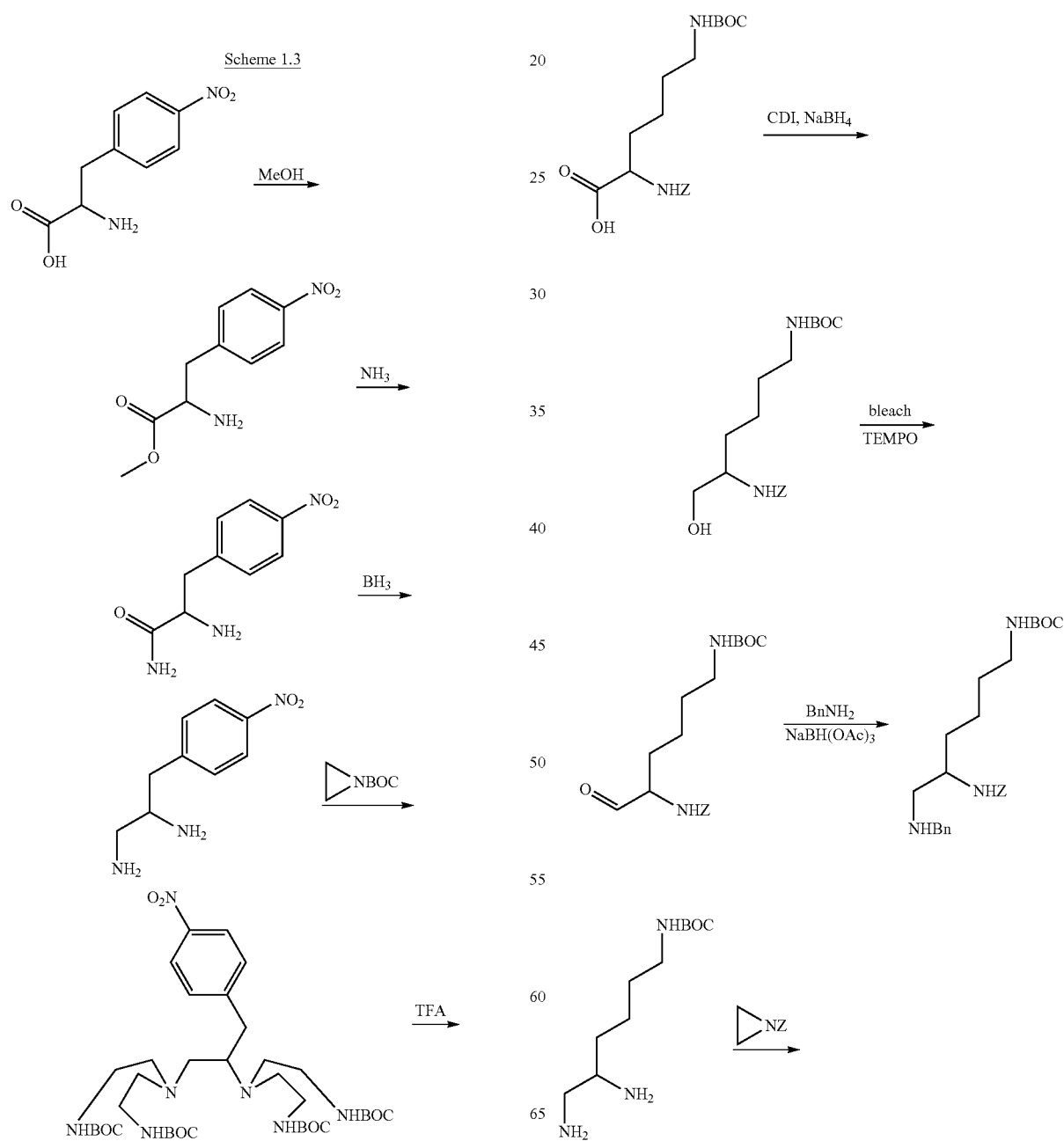

-continued

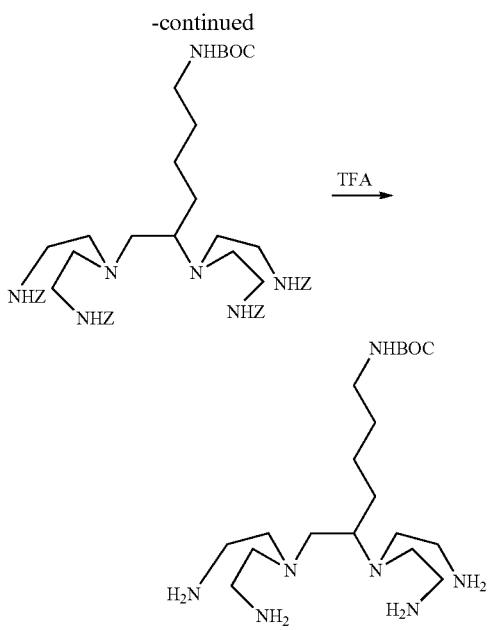

Functional Moiety

In one exemplary embodiment, the complexes of the invention are derivatized with at least one functional moiety. The term "functional moiety" includes any substituent group, which is useful to link a complex of the invention to another molecule. Such linkage can be either covalent or non-covalent. Hence, the functional moiety may contain a reactive functional group. "Functional moiety" also includes any substituent group that includes a targeting moiety, such as a polypeptide, a ligand to a receptor, an antibody and the like.

The functional moiety is preferably attached, so that the resulting functionalized ligand will be able to undergo formation of stable metal ion complexes. In one exemplary embodiment, the functional moiety can be attached to the scaffold moiety, for instance, to one of the linker groups, such as $L^1$ or $L^2$ in Formula (III). In another exemplary embodiment, the functional moiety is attached to one of the chelating moieties of Formula (I) or Formula (II). For example, the functional moiety can be part of $R^{11}$ in a TAM moiety. The functional moiety can also be attached to any other linker moiety (e.g., $R^5$ may include a functional moiety) or linker group within the complex. In another example, a functional moiety is attached to at least one of $L^1$, $L^2$, $L^3$, $L^4$ or $L^5$ in Formula (IV) and/or Formula (V).

Exemplary organic ligands including a functional moiety are shown below:

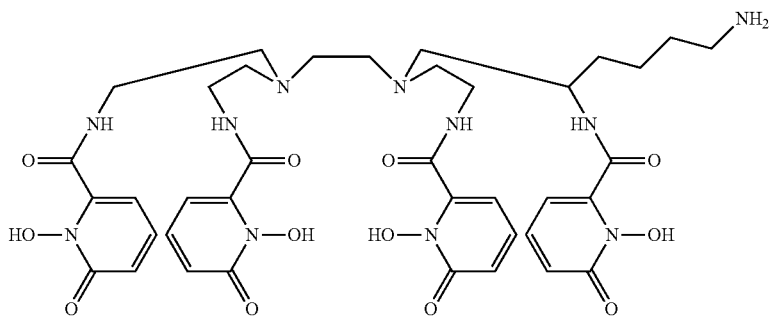

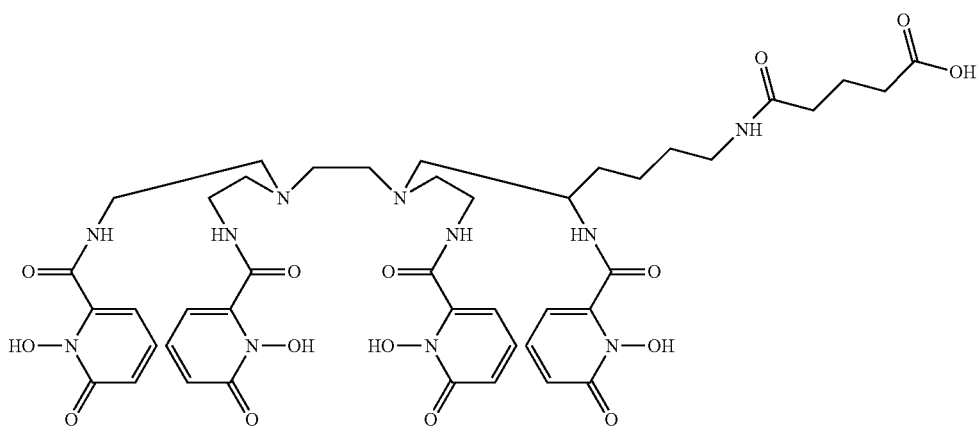

In an exemplary embodiment, the functional moiety has the structure:

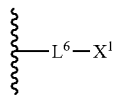

wherein $L^6$ is a linker moiety, which is a member selected from substituted or unsubstituted alkyl, substituted or unsubstituted heteroalkyl, substituted or unsubstituted aryl, substituted or unsubstituted heteroaryl and substituted or unsubstituted heterocycloalkyl. $X^1$ is a member selected from a reactive functional group and a targeting moiety.

Reactive Functional Groups

In one embodiment, the functional moiety includes a reactive functional group, which can be used to covalently attach the ligand to a targeting moiety, such as a protein, a small molecule, a lipid, a carbohydrate and the like. Alternatively, the reactive functional group can be used to link the ligand to a nano-particle of any kind. Reactive groups and classes of reactions useful in practicing the present invention are generally those that are well known in the art of bioconjugate chemistry. Currently favored classes of reactions available with reactive functional groups of the invention are those which proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in: March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

a) Amines and Amino-Reactive Groups

In one embodiment, the reactive functional group is a member selected from amines, such as a primary or secondary amine, hydrazines, hydrazides, and sulfonylhydrazides. Amines can, for example, be acylated, alkylated or oxidized. Useful non-limiting examples of amino-reactive groups include N-hydroxysuccinimide (NHS) esters, sulfur-NHS esters, imidoesters, isocyanates, isothiocyanates, acylhalides, arylazides, p-nitrophenyl esters, aldehydes, sulfonyl chlorides, thiazolides and carboxyl groups.

NHS esters and sulfur-NHS esters react preferentially with the primary (including aromatic) amino groups of the reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with the amine groups of e.g., a protein. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of carboxylic acids are also useful amino-reactive groups. Although the reagent specificity is not very high, α- and ε-amino groups appear to react most rapidly.

Aldehydes react with primary amines of the conjugate components (e.g., ε-amino group of lysine residues). Although unstable, Schiff bases are formed upon reaction of the protein amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., *Biochemistry* 1981, 20: 4836-4842, e.g., teach how to modify a protein with carbodiimides.

b) Sulfhydryl and Sulfhydryl-Reactive Groups

In another embodiment, the reactive functional group is a member selected from a sulfhydryl group (which can be converted to disulfides) and sulfhydryl-reactive groups. Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

c) Other Reactive Functional Groups

Other exemplary reactive functional groups include:

(i) carboxyl groups and various derivatives thereof including, but not limited to, N-hydroxybenztriazole esters, acid halides, acyl imidazoles, thioesters, p-nitrophenyl esters, alkyl, alkenyl, alkynyl and aromatic esters;

(ii) hydroxyl groups, which can be converted to esters, ethers, aldehydes, etc.;

(iii) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;

(iv) dienophile groups, which are capable of participating in Diels-Alder reactions such as, for example, maleimido groups;

(v) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(vi) alkenes, which can undergo, for example, cycloadditions, acylation, Michael addition, etc;

(vii) epoxides, which can react with, for example, amines and hydroxyl groups;

(ix) phosphoramidites and other standard functional groups useful in nucleic acid synthesis and (x) any other functional group useful to form a covalent bond between the functionalized ligand and a molecular entity or a surface.

d) Functional Groups with Non-Specific Reactivities

In addition to the use of site-specific reactive moieties, the present invention contemplates the use of non-specific reactive groups to link the ligand to a targeting moiety. Non-specific groups include photoactivatable groups, for example.

Photoactivatable groups are ideally inert in the dark and are converted to reactive species in the presence of light. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein cross-links.

It is well within the abilities of a person skilled in the art to select a reactive functional group, according to the reaction partner. As an example, an activated ester, such as an NHS ester will be useful to label a protein via lysine residues. Sulfhydryl reactive groups, such as maleimides can be used to label proteins via amino acid residues carrying an SH-group (e.g., cystein). Antibodies may be labeled by first oxidizing their carbohydrate moieties (e.g., with periodate) and reacting resulting aldehyde groups with a hydrazine containing ligand.

The reactive functional groups can be chosen such that they do not participate in, or interfere with, the reactions necessary to assemble the reactive ligand. Alternatively, a reactive functional group can be protected from participating in the reaction by means of a protecting group. Those of skill in the art understand how to protect a particular functional group so that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Targeting Moieties

Exemplary targeting moieties include small-molecule ligands, lipids, linear and cyclic peptides, polypeptides (e.g., EPO, insulin etc.), proteins, such as enzymes and receptors and fusion proteins. Other targeting moieties include antibodies and antibody fragments (e.g., those generated to recognize small-molecules and receptor ligands), antigens, nucleic acids (e.g. RNA and cDNA), carbohydrate moieties (e.g., polysaccharides), lipids and pharmacologically active molecules, such as toxins, pharmaceutical drugs and drugs of abuse (e.g. steroids).

Additional targeting moieties are selected from solid supports and polymeric surfaces (e.g., polymeric beads and plastic sample reservoirs, such as plastic well-plates), sheets, fibers and membranes. Targeting moieties also include particles (e.g., nano-particles) and drug-delivery vehicles.

In one embodiment, the targeting moiety includes at least one unit of a macrocyclic compound. In another exemplary embodiment, the compound of the invention has a dendrimeric structure and encompasses several ligands of the invention covalently linked to each other. In a further exemplary embodiment, according to this aspect, a complex based on such dendrimer includes at least two metal ions.

In another exemplary embodiment, the Linker moiety $L^6$ or the targeting moiety include a polyether, such as polyethylene glycol (PEG) and derivatives thereof. In one example, the polyether has a molecular weight between about 50 to about 10,000 daltons.

In one exemplary embodiment, the targeting moiety is a protein containing a lipid recognition motif. Exemplary lipid binding proteins include those that bind to phosphatidylinositol, phosphatidylinositol phosphates or other biological lipids.

In another exemplary embodiment, the targeting moiety is substituted with a luminescence modifying group that allows luminescence energy transfer between a complex of the invention and the luminescence modifying group when the complex is excited.

In one example, the functional moiety has the structure:

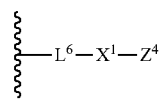

wherein $L^6$ is a linker moiety, which is a member selected from substituted or unsubstituted alkyl, substituted or unsubstituted heteroalkyl, substituted or unsubstituted aryl, substituted or unsubstituted heteroaryl and substituted or unsubstituted heterocycloalkyl. $X^1$ is a targeting moiety and $Z^4$ is a luminescence modifying group allowing luminescence energy transfer between said complex and said luminescence modifying group when said complex is excited.

Linker Moiety $L^6$

In one preferred embodiment, the linker moiety $L^6$ of the functional moiety is long enough to avoid side reactions during synthesis (e.g. intra-molecular reactions, such as intra-molecular peptide bond formation), to allow coupling of the organic ligand or complex of the invention to a targeting moiety and to allow the targeting moiety to fulfill its intended function. Useful linkers include those with about 2 to about 50 linear atoms, preferably about 4 to about 20 linear atoms.

In one exemplary embodiment the linker moiety includes an aliphatic carbon chain or a poly-ethyleneglycol (PEG) chain. Thus, the functional moiety includes a structure which is a member selected from:

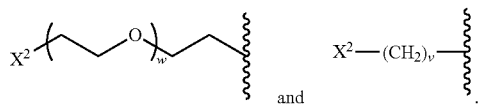

Exemplary $X^2$ groups include OH, alkoxy, and one of the following structures:

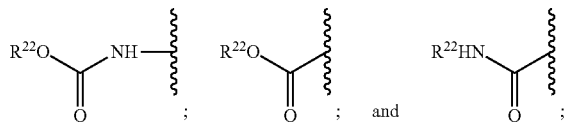

wherein $R^{22}$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl. The integer v is selected from 1 to 20, and w is an integer from 1 to 1,000.

In another exemplary embodiment, the functional moiety has the structure:

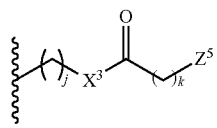

wherein $Z^5$ is a member selected from H, $OR^{23}$, $SR^{23}$, $NHR^{23}$, $OCOR^{24}$, $OC(O)NHR^{24}$, $NHC(O)OR^{23}$, $OS(O)_2OR^{23}$, and $C(O)R^{24}$. $R^{23}$ is a member selected from H, substituted or unsubstituted alkyl, and substituted or unsubstituted heteroalkyl. $R^{24}$ is a member selected from H, $OR^{25}$, $NR^{25}NH_2$, SH, $C(O)R^{25}$, $NR^{25}H$, substituted or unsubstituted alkyl and substituted or unsubstituted heteroalkyl. $R^{25}$ is a member selected from H, substituted or unsubstituted alkyl and substituted or unsubstituted alkyl. $X^3$ is a member selected from O, S and $NR^{26}$, wherein $R^{26}$ is a member selected from H, substituted or unsubstituted alkyl and substituted or unsubstituted heteroalkyl. The integers j an k are members independently selected from 1 to 20.

In linker arms with multiple reactive functional groups, a particular functional group can be chosen such that it does not participate in, or interfere with, the reaction controlling the attachment of the functionalized spacer component to another ligand component. Alternatively, the reactive functional group can be protected from participating in the reaction by the presence of a protecting group. Those of skill in the art understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

In one embodiment, the linker attaches the ligand to a targeting group essentially irreversibly via a "stable bond" between the components. A "stable bond", as used herein, is a bond, which maintains its chemical integrity over a wide range of conditions (e.g., amide, carbamate, carbon-carbon, ether, etc.). In another embodiment the linker attaches two or more components by a "cleaveable bond". A "cleaveable bond", as used herein, is a bond which is designed to undergo scission under selected conditions. Cleaveable bonds include, but are not limited to, disulfide, imine, carbonate and ester bonds.

In an exemplary embodiment, the complex of the invention includes a water-soluble polymer as a scaffold moiety, or as a targeting moiety. Exemplary water-soluble polymers include polylysine, polyethylene glycol (PEG) or polydextran (Dresser, T. R. et al., *J. Magn. Reson. Imaging* 1994, 4: 467)

Thus, in another embodiment, the invention provides a complex (e.g., of Formula III), wherein at least one of $R^1$, $R^2$, $R^3$, and $R^4$ comprise a moiety derived from polyethylene glycol (PEG). PEG is used in biotechnology and biomedical applications. The use of this agent has been reviewed (POLY-ETHYLENE GLYCOL CHEMISTRY: BIOTECHNICAL AND BIOMEDICAL APPLICATIONS, J. M. Harris, Ed., Plenum Press, New York, 1992). Modification of enzymes (Chiu et al., *J. Bioconjugate Chem.*, 4: 290-295 (1993)), RGD peptides (Braatz et al., *Bioconjugate Chem.*, 4: 262-267 (1993)), liposomes (Zalipsky, S. *Bioconjugate Chem.*, 4: 296-299 (1993)), and CD4-IgG glycoprotein (Chamow et al., *Bioconjugate Chem.*, 4: 133-140 (1993)) are some of the recent advances in the use of polyethylene glycol. Surfaces treated with PEG have been shown to resist protein deposition and have improved resistance to thrombogenicity when coated on blood contacting biomaterials (Merrill, "Poly(ethylene oxide) and Blood Contact: A Chronicle of One Laboratory," in POLY(ETHYLENE GLYCOL) CHEMISTRY: BIOTECHNICAL AND BIOMEDICAL APPLICATIONS, Harris, Ed., Plenum Press, New York, (1992), pp. 199-220).

Many routes are available for attaching a ligand or complex of the invention onto a polymeric or oligomeric species. See, for example, Dunn, R. L., et al., Eds. POLYMERIC DRUGS AND DRUG DELIVERY SYSTEMS, ACS Symposium Series Vol. 469, American Chemical Society, Washington, D.C. 1991; Herren et al., *J. Colloid and Interfacial Science* 115: 46-55 (1987); Nashabeh et al., *J. Chromatography* 559: 367-383 (1991); Balachandar et al., *Langmuir* 6: 1621-1627 (1990); and Burns et al., *Biomaterials* 19: 423-440 (1998).

Many activated derivatives of PEG are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.*, 7: 175-186 (1984); Abuchowski et al., *J. Biol. Chem.*, 252: 3582-3586 (1977); Jackson et al., *Anal. Biochem.*, 165: 114-127 (1987); Koide et al., *Biochem Biophys. Res. Commun.*, 111: 659-667 (1983)), tresylate (Nilsson et al., *Methods Enzymol.*, 104: 56-69 (1984); Delgado et al., *Biotechnol. Appl. Biochem.*, 12: 119-128 (1990)); N-hydroxysuccinimide derived active esters (Buckmann et al., *Makromol. Chem.*, 182: 1379-1384 (1981); Joppich et al., *Makromol. Chem.*, 180: 1381-1384 (1979); Abuchowski et al., *Cancer Biochem. Biophys.*, 7: 175-186 (1984); Katre et al. *Proc. Natl. Acad. Sci. U.S.A.*, 84: 1487-1491 (1987); Kitamura et al., *Cancer Res.*, 51: 4310-4315 (1991); Boccu et al., *Z. Naturforsch.*, 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.*, 15: 100-114 (1992); Veronese et al., *Appl. Biochem. Biotech.*, 11: 141-152 (1985)), imidazolyl formates (Beauchamp et al., *Anal. Biochem.*, 131: 25-33 (1983); Berger et al., *Blood*, 71: 1641-1647 (1988)), 4-dithiopyridines (Woghiren et al., *Bioconjugate Chem.*, 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.*, 11: 141-152 (1985).

In another aspect, the present invention provides a metal complex as set forth above, which is attached to a dendrimer via a reactive functional group. Similar to the linker group discussed above, the dendrimer will have at least two reactive functional groups. In one embodiment, one or more fully assembled ligand is attached to the dendrimer. Alternatively, the dendrimer is selected such that it serves as the linker and the chelate is formed directly on the dendrimer.

In one embodiment, complexes of the invention noncovalently bind to macromolecules within a cell, tissue or body (Lauffer, R. B., *Magn. Reson. Med.* 1991, 22, 339). The binding causes an increased concentration and retention of the luminescent complex in the localized region of the biomolecule. The art is replete with examples of metal complexes designed to bind selected targets in vivo. For example, the complex MS-325 forms a noncovalent adduct with the blood protein human serum albumin (HSA) (Parmalee, D. J. W. et al., *Invest. Radiol.* 1997, 32, 741; Lauffer, R. B. P. et al., *Radiology* 1998, 207, 529). Lanthanide complexes have also been designed to target other macromolecules. For example, Gd-BOPTA was designed to target hepatocytes in order to facilitate hepatobiliary imaging (Cavanga, F. M. et al., *Invest. Radiol.* 1997, 32, 780).

Luminescence Modifying Groups (Donor and Acceptor Moieties)

The luminescent compounds of the invention can be used with a wide range of energy donor and acceptor molecules to construct luminescence energy transfer pairs, e.g., fluorescence energy transfer (FET) probes. Fluorophores useful in conjunction with the complexes of the invention are known to those of skill in the art. See, for example, Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

A non-limiting list of exemplary donor or acceptor moieties that can be used in conjunction with the luminescent complexes of the invention, is provided in Table 1.

TABLE 1

Suitable Moieties Useful as Donors or Acceptors in FET Pairs 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4',5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red TABLE 1-continued Suitable Moieties Useful
as Donors or Acceptors in FET Pairs B-phycoerythrin
o-phthaldialdehyde
pyrene and derivatives:
    pyrene
    pyrene butyrate
    succinimidyl 1-pyrene butyrate
quantum dots
Reactive Red 4 (Cibacron™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
    tetramethyl rhodamine
tetramethyl rhodamine isothiocyanate (TRITC)
riboflavin
rosolic acid
lanthanide chelate derivatives There is practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970). The literature also includes references providing exhaustive lists of fluorescent and chromogenic molecules and their relevant optical properties, for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups that can be added to a molecule.

The diversity and utility of chemistries available for conjugating fluorophores to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a small molecular bioactive material, nucleic acid, peptide or other polymer.

In a FET pair, it is generally preferred that an absorbance band of the acceptor substantially overlap a fluorescence emission band of the donor. When the donor (fluorophore) is a component of a probe that utilizes fluorescence resonance energy transfer (FRET), the donor fluorescent moiety and the quencher (acceptor) of the invention are preferably selected so that the donor and acceptor moieties exhibit fluorescence resonance energy transfer when the donor moiety is excited. One factor to be considered in choosing the fluorophore-quencher pair is the efficiency of fluorescence resonance energy transfer between them. Preferably, the efficiency of FRET between the donor and acceptor moieties is at least 10%, more preferably at least 50% and even more preferably at least 80%. The efficiency of FRET can easily be empirically tested using the methods both described herein and known in the art.

The efficiency of FRET between the donor-acceptor pair can also be adjusted by changing ability of the donor and acceptor to dimerize or closely associate. If the donor and acceptor moieties are known or determined to closely associate, an increase or decrease in association can be promoted by adjusting the length of a linker moiety, or of the probe itself, between the two fluorescent entities. The ability of donor-acceptor pair to associate can be increased or decreased by tuning the hydrophobic or ionic interactions, or the steric repulsions in the probe construct. Thus, intramolecular interactions responsible for the association of the donor-acceptor pair can be enhanced or attenuated. Thus, for example, the association between the donor-acceptor pair can be increased by, for example, utilizing a donor bearing an overall negative charge and an acceptor with an overall positive charge.

In addition to fluorophores that are attached directly to a probe, the fluorophores can also be attached by indirect means. In this embodiment, a ligand molecule (e.g., biotin) is preferably covalently bound to the probe species. The ligand then binds to another molecules (e.g., streptavidin) molecule, which is either inherently detectable or covalently bound to a signal system, such as a fluorescent compound of the invention, or an enzyme that produces a fluorescent compound by conversion of a non-fluorescent compound. Useful enzymes of interest as labels include, for example, hydrolases, particularly phosphatases, esterases and glycosidases, or oxidotases, particularly peroxidases. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

IV. Methods

The complexes of the invention are useful as probes in a variety of biological assay systems and diagnostic applications. An overview of assay systems, such as competitive assay formats, immunological assays, microarrays, membrane binding assays and enzyme activity assays, is given e.g., in U.S. Pat. No. 6,864,103 to Raymond et al., which is incorporated herein in its entirety for all purposes. It is within the ability of one of skill in the art to select and prepare a probe that includes a complex of the invention, and which is suitable for a selected assay system. In an exemplary embodiment, the luminescent probe molecule is used to detect the presence or absence of an analyte in a sample.

Thus, in a second aspect, the invention provides mixtures that contain a luminescent complex of the invention and an analyte.

In a third aspect, the invention provides a method of detecting the presence or absence of an analyte in a sample. The method comprises (a) contacting the sample and a composition including a complex of the invention; (b) exciting said complex; and (c) detecting luminescence from the complex.

In a fourth aspect, the invention provides a method of detecting the presence or absence of an analyte in a sample. The method comprises (a) contacting the sample and a composition including a complex of the invention, and a luminescence modifying group, wherein energy can be transferred between the complex and the luminescence modifying group when the complex is excited, and wherein the complex and the luminescence modifying group can be part of the same molecule or be part of different molecules; and (b) exciting said complex; and (c) determining the luminescent property of the sample, wherein the presence or absence of the analyte is indicated by the luminescent property of the sample. In one example, the presence or absence of the analyte results in a change of the luminescent property of the sample.

In an exemplary embodiment, the analyte is detected using a competition assay format. For example, the analyte, if present in the sample, displaces a targeting moiety of a complex of the invention from a binding site located on a recognition molecule, by binding to the binding site.

Hence, in another aspect, the invention provides a kit including a recognition molecule and a complex of the invention. Exemplary recognition molecules include biomolecules, such as whole cells, cell-membrane preparations, antibodies, antibody fragments, proteins (e.g., cell-surface receptors, such as G-protein coupled receptors), protein domains, peptides, nucleic acids and the like. Alternatively the kit may contain a lanthanide ion and an organic ligand, which form a luminescent complex when contacted with each other.

Analytes

The compounds, complexes and methods of the invention can be used to detect any analyte or class of analytes in any sample. A sample may contain e.g., a biological fluid or tissue. Other samples can e.g., include solutions of synthetic molecules or extracts from a plant or microorganism (e.g., for drug screening efforts). Exemplary analytes are pharmaceutical drugs, drugs of abuse, synthetic small molecules, biological marker compounds, hormones, infectious agents, toxins, antibodies, proteins, lipids, organic and inorganic ions, carbohydrates and the like. (see e.g., U.S. Pat. No. 6,864,103 to Raymond et al. for additional examples of analytes).

Synthesis

The following section and the Examples appended hereto set forth exemplary synthetic routes to compounds of the invention.

1-Hydroxy-2-pyridinone (1,2-HOPO) Complexes

Useful 1,2-HOPO ligands of the invention and their metal chelates may be synthesized using art recognized methods. In one example, the ligands are synthesized utilizing a reactive 1,2-HOPO intermediate prepared from the corresponding acid as described, e.g., in Appendix B, which is incorporated into this application in its entirety.

Once the ligand is formed and purified, the metal complex is synthesized by any of a wide range of art-recognized methods, including, for example, by incubating a salt of the ligand with a metal salt, such as a lanthanide salt (e.g., lanthanide trihalide, lanthanide triacetate). The reaction of the ligand with the metal ion is carried out either before or after coupling the ligand to a targeting moiety in order to generate a complex of the invention.

For example, 1,2-HOPO derivatives in which the carboxylic acid is activated as an acid halide and the N-hydroxyl group is protected can be used to prepare the organic ligands that form the complexes of the invention.

An exemplary method of preparing a 1,2-HOPO chelator is outlined in Scheme 1:

Scheme 1

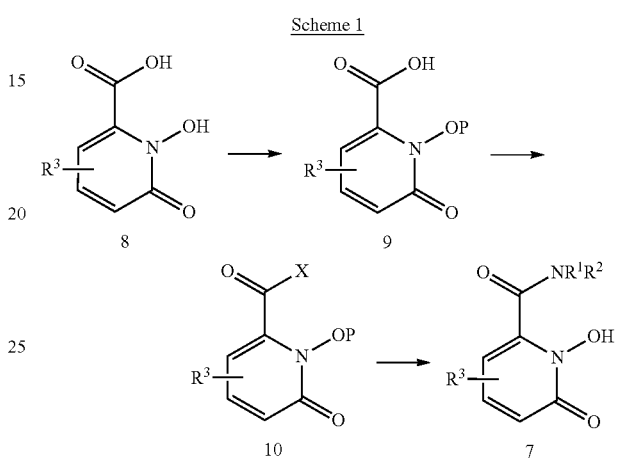

$R^1$ and $R^2$ represent members independently selected from the group described herein as aryl group substituents. The symbol $R^3$ represents a member selected from the group of H, $C_1$-$C_4$ substituted or unsubstituted alkyl, and substituted or unsubstituted aryl.

The method includes contacting compounds of structure 8 with a protecting agent, thereby forming the protected compounds of structure 9, in which P is a protecting group. Compounds according to structure 9 are then contacted with an agent that converts the carboxylic acid to the corresponding acid halide, thereby forming compounds of structure 10, which are then contacted with $HNR^1R^2$ and subsequently deprotected thereby forming the chelators according to structure 7.

An example of this method according to Scheme 1 is:

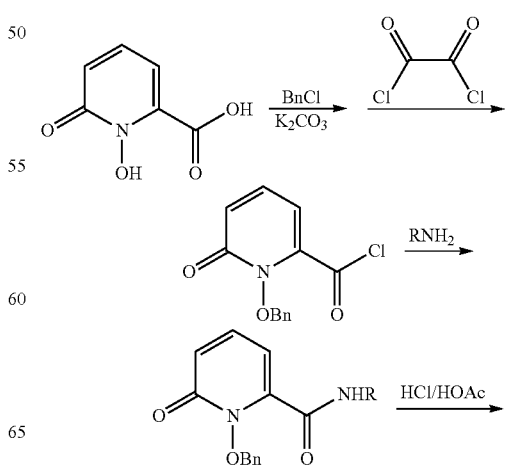

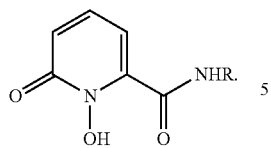

In an exemplary embodiment, the route from 1-hydroxy-2(1H)pyridinone-6-carboxylic acid to the corresponding amide involves the steps:

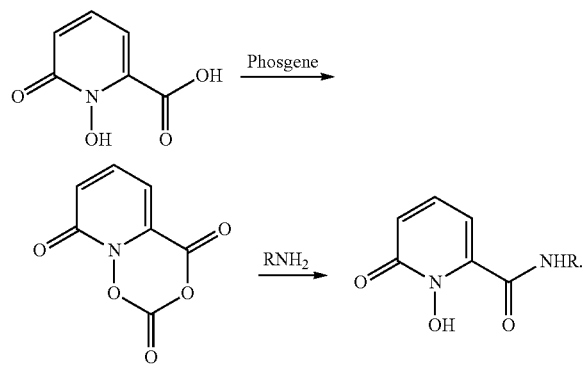

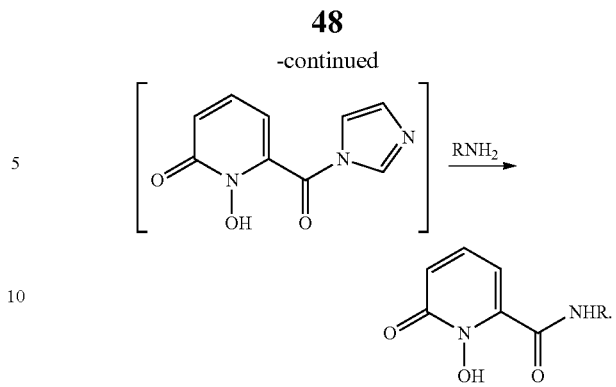

In a presently preferred embodiment, the acid halide is an acid chloride. A presently preferred agent for converting the carboxylic acid to the halide is oxalyl chloride. Other acid halides and agents for converting the carboxylic acid to those halides will be apparent to those of skill in the art. See, for example, Wade, COMPENDIUM OF ORGANIC SYNTHETIC METHODS, John Wiley and Sons, New York, 1984; and March, ADVANCED ORGANIC CHEMISTRY, 4th Edition, Wiley-Interscience, New York.

The protected 1,2-HOPO acid 9 can also be activated by forming various activated esters or amides. An exemplary reaction sequence is shown below in Scheme 2:

Scheme 2

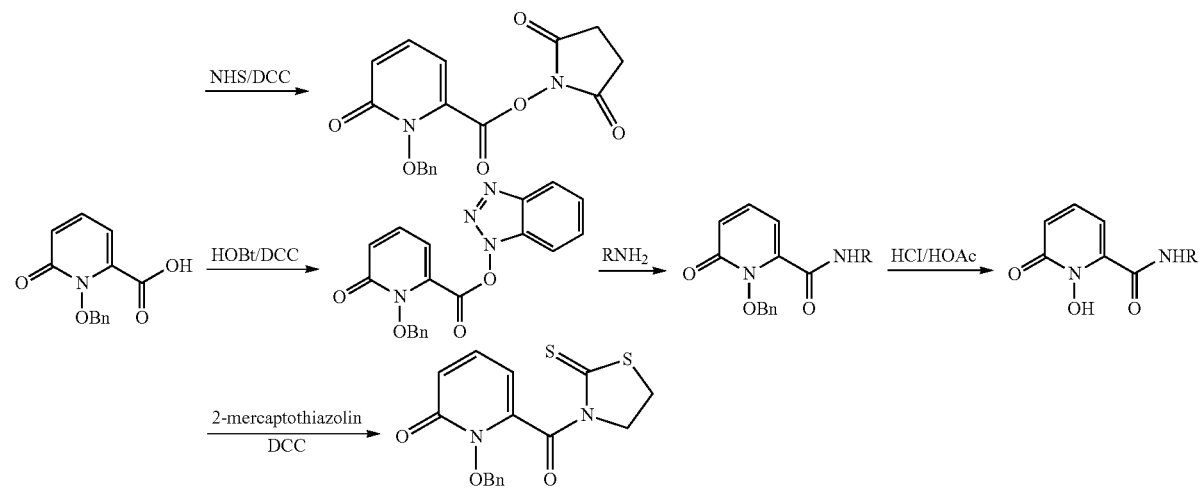

In another exemplary route, the acid is activated with carbonyldiimidazole:

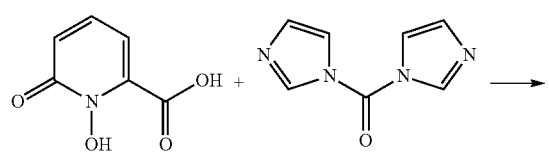

Benzyl protected 1,2-HOPO-6-carboxylic acid (1,2-HOPOBn acid) is a versatile compound for synthesizing 1,2-HOPO ligands. It can be converted to various activated intermediates and then coupled to a variety of amines, sulfhydryls, alcohols and other nucleophilic groups. For example, 1,2-HOPO-6-carboxylic acid reacts with 2-mercaptothiazoline in the presence of DCC (dicyclohexyl carbodiimide) and DMAP (1,4-Dimethylaminopyridine) to give 1,2-HOPO thiazolide, which selectively reacts with aliphatic primary amines, like its 3,2-HOPO analogue, 3,2-HOPO-thiazolide. The protected HOPO-acid can also be converted to the corresponding N-hydroxysuccinimide or other activated esters and coupled to various backbones that include nucleophilic moieties. In most cases, the active esters are not isolated, but are coupled with amines or other nucleophilic moieties in situ.

Protecting agents and protecting groups useful in practicing the present invention are generally those known in the art to be of use in protecting hydroxyl moieties (see, for example, Greene, PROTECTIVE GROUPS IN ORGANIC SYNTHESIS, 2nd Edition, Wiley-Interscience, 1991). A presently preferred protecting group is the benzyl group. Preferred protecting agents include, but are not limited to, benzyl halides, benzyl sulfonates, and benzyl triflates.

The chelating agent 1,2HOIQO is prepared and attached to an exemplary scaffold by the scheme set forth below:

ment, $NR^{17}R^{18}$ is a polyamine Preferred polyamines include 1,3-diaminopropane, spermidine, and spermine Representative amine species to which compound 10 can be conjugated include, but are not limited to, those set forth in U.S. Pat. No. 4,698,431, U.S. Pat. No. 5,624,901 and U.S. Pat. No. 5,892,029, the disclosures of which are incorporated herein by reference.

An exemplary synthetic route for the synthesis of octadentate, tetrapodal 1,2-HOPO ligands is outlined in Schemes 3 to 5:

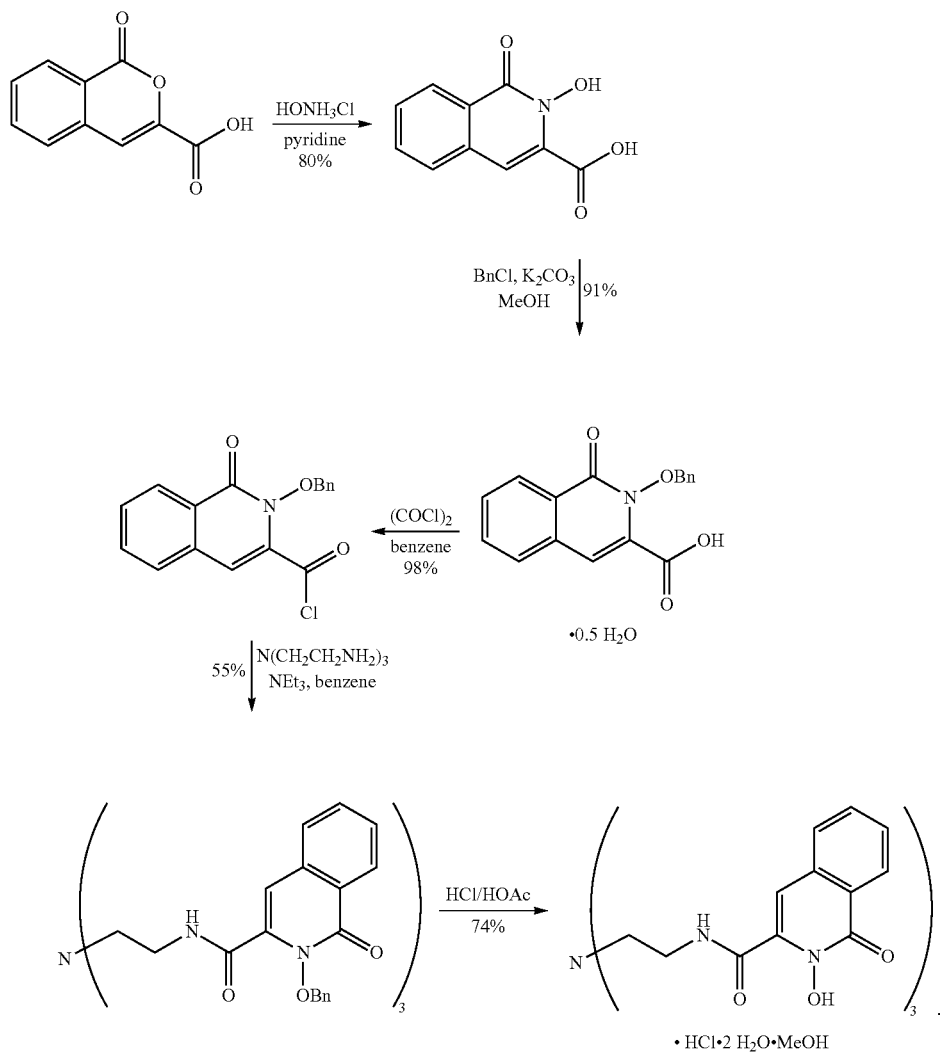

As will be apparent to those of skill in the art, if the synthesis is initiated with a starting material functionalized on the phenyl ring or the heterocycle, a similarly functionalized chelating moiety will result. The scaffold set forth above is purely exemplary and it is understood that any of the scaffolds set forth herein, or art recognized scaffolds are equally applicable.

Any nucleophilic species that reacts with the material according to structure 10 is useful in practicing the present invention. In a preferred embodiment, the nucleophilic species is an amine, $NR^{17}R^{18}$. In a further preferred embodi- Scheme 3

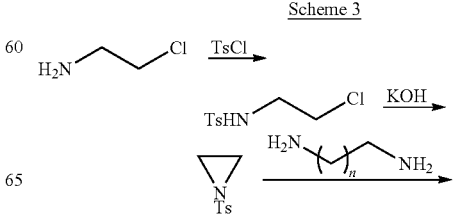

51
-continued
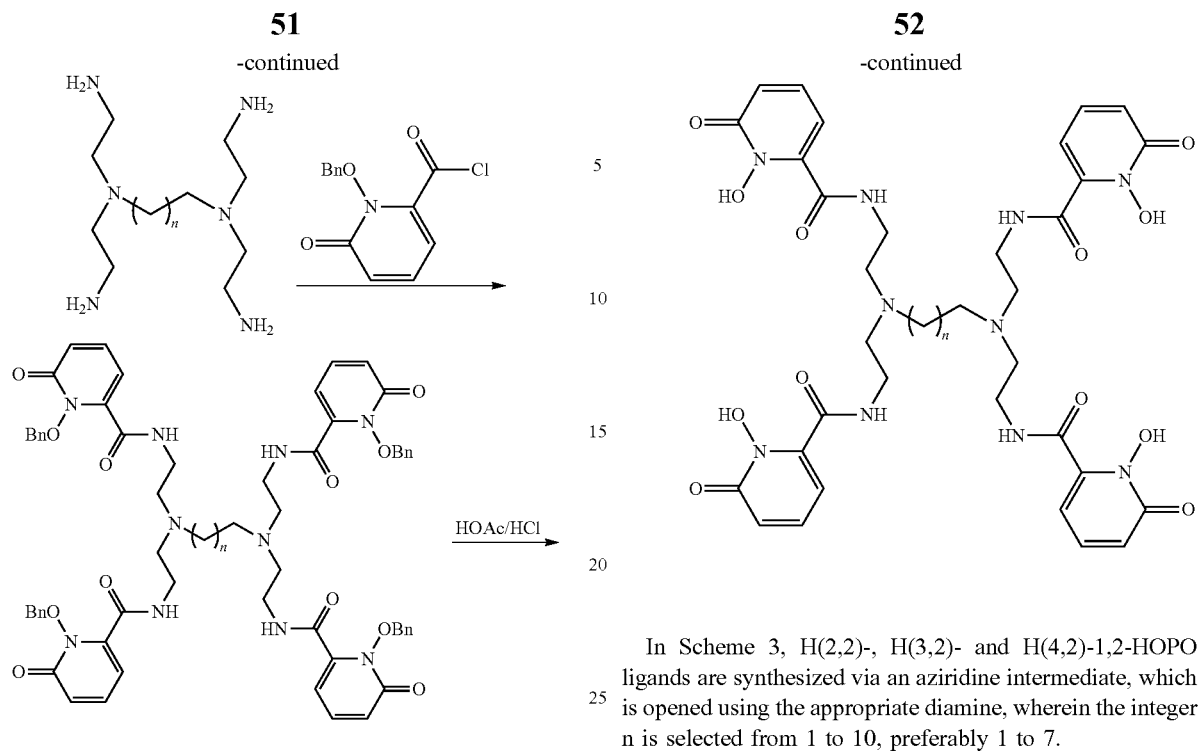
In Scheme 3, H(2,2)-, H(3,2)- and H(4,2)-1,2-HOPO ligands are synthesized via an aziridine intermediate, which is opened using the appropriate diamine, wherein the integer n is selected from 1 to 10, preferably 1 to 7.
Scheme 4
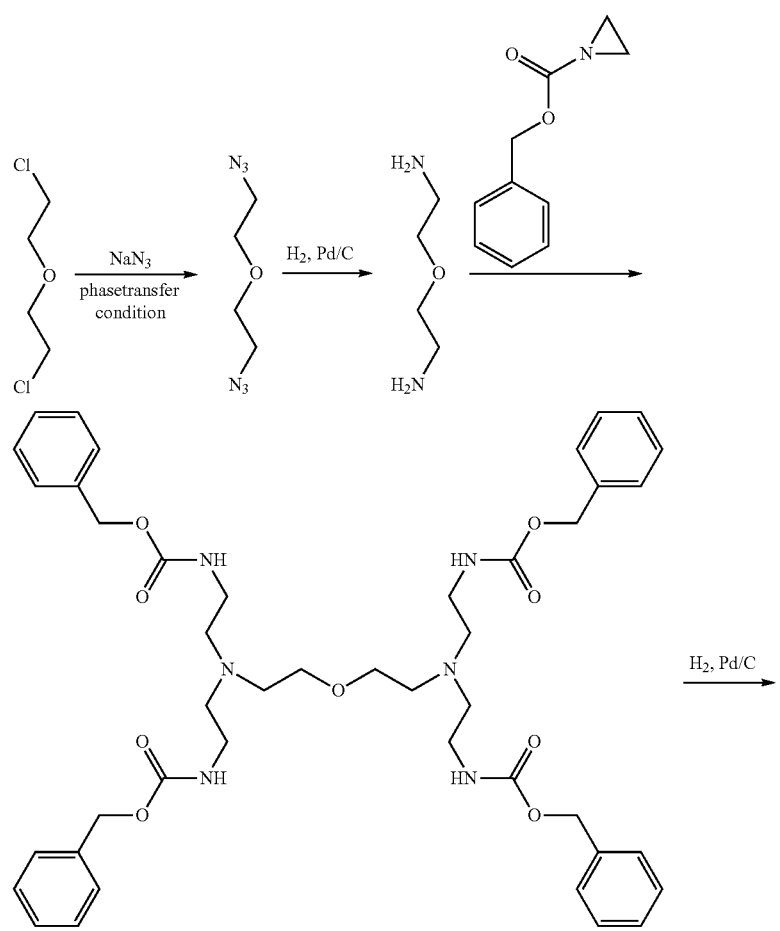

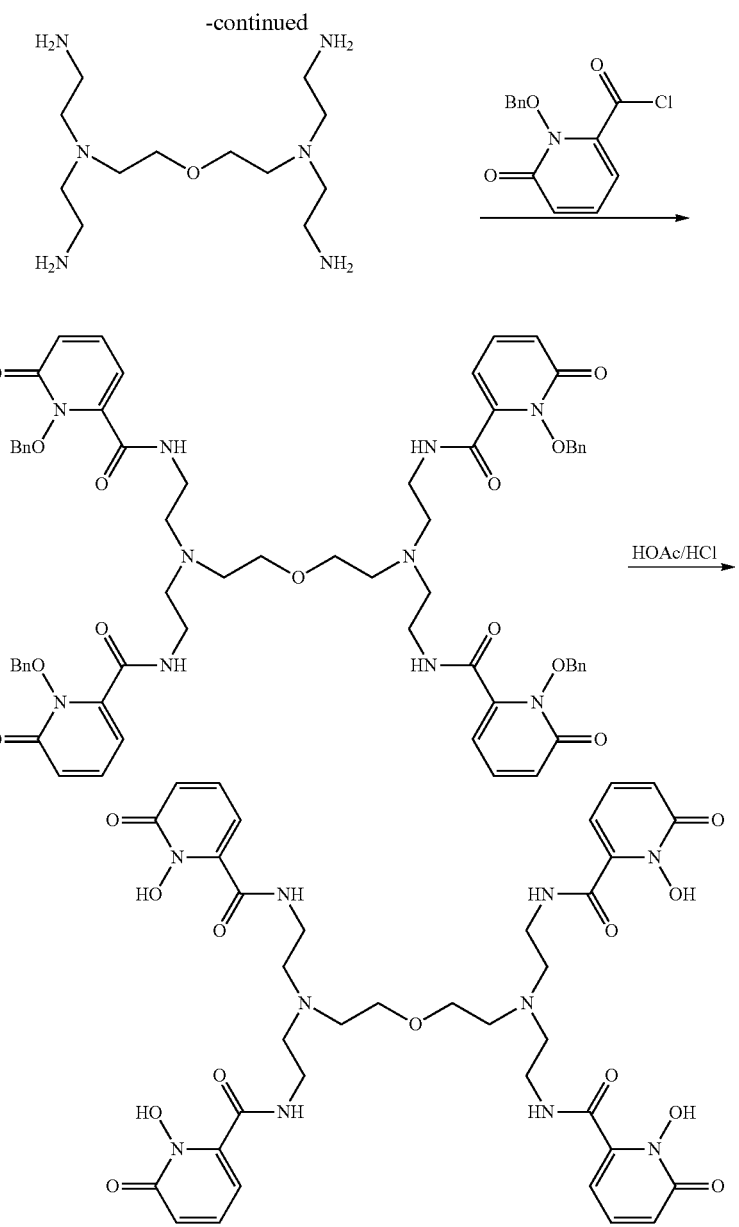
Scheme 4 outlines the synthesis of H(5O,2)-1,2-HOPO.
Scheme 5
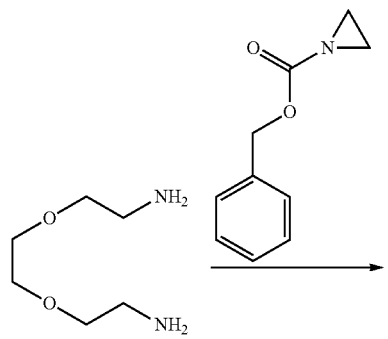

-continued
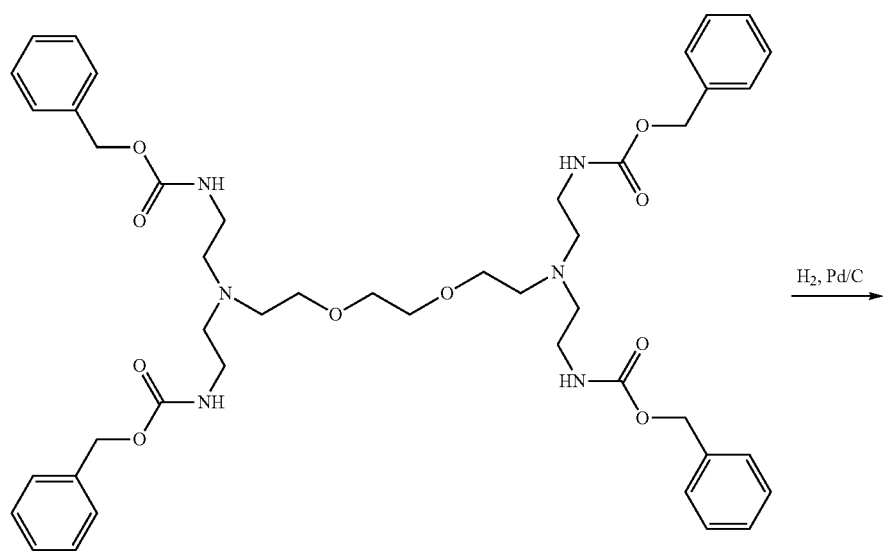
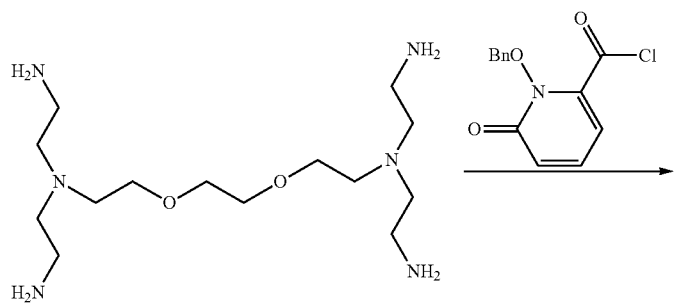
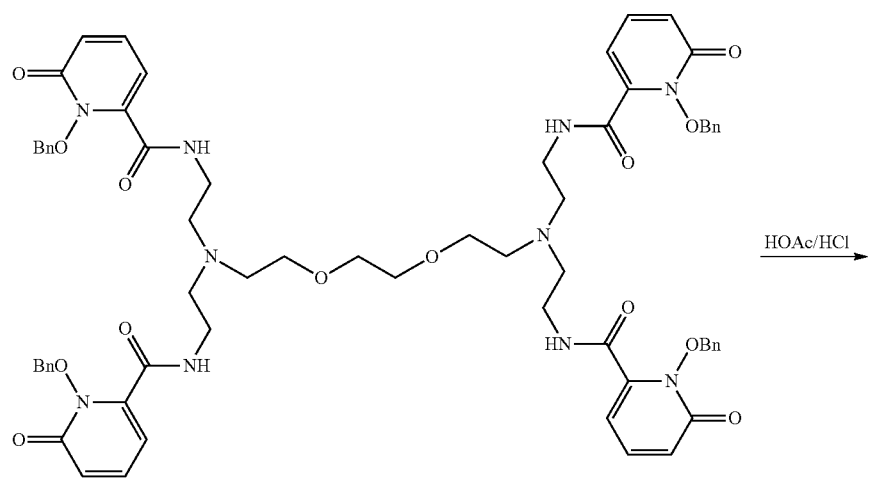

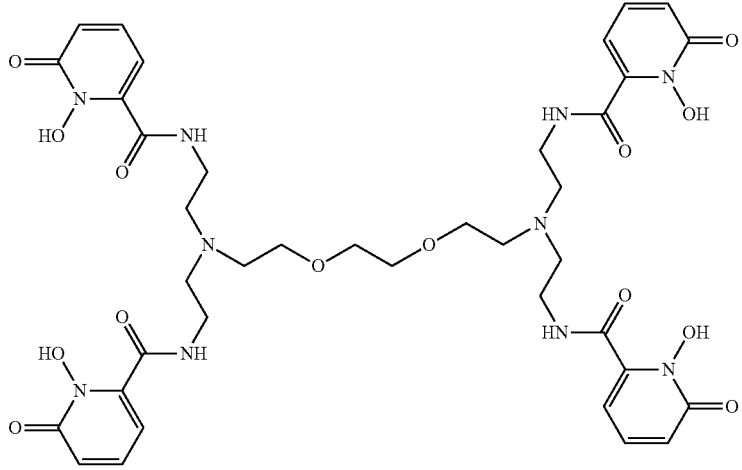

Scheme 5 outlines the synthesis of H(8O2,2)-1,2-HOPO.

The carboxylic acid starting material according to structure 8 may be prepared by any method known in the art. In a preferred embodiment, the carboxylic acid is prepared by a method that includes contacting a trifluoroacetic acid solution of a hydroxyl-containing compound having a structure according to structure 11:

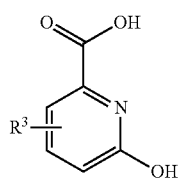

with a mixture comprising acetic anhydride and hydrogen peroxide, thereby forming a precipitate of an N-hydroxyamide compound having a structure according to structure 9. Other starting materials for the preparation of 8 include 6-chloro-picolinic acid and 6-bromo-picolinic acid.

Mixed ligands that include at least one 1,2-HOPO subunit in combination with another complexing moiety can also be prepare using art recognized methods.

Functionalization of 1-Hydroxy-2-Pyridinonate Chelating Agents

TAM moieties conveniently contain a second amide group, which can be functionalized either prior to or following connection with the scaffold moiety (e.g., TREN in Scheme 6 or the octadentate scaffold H(2,2)).

Scheme 6

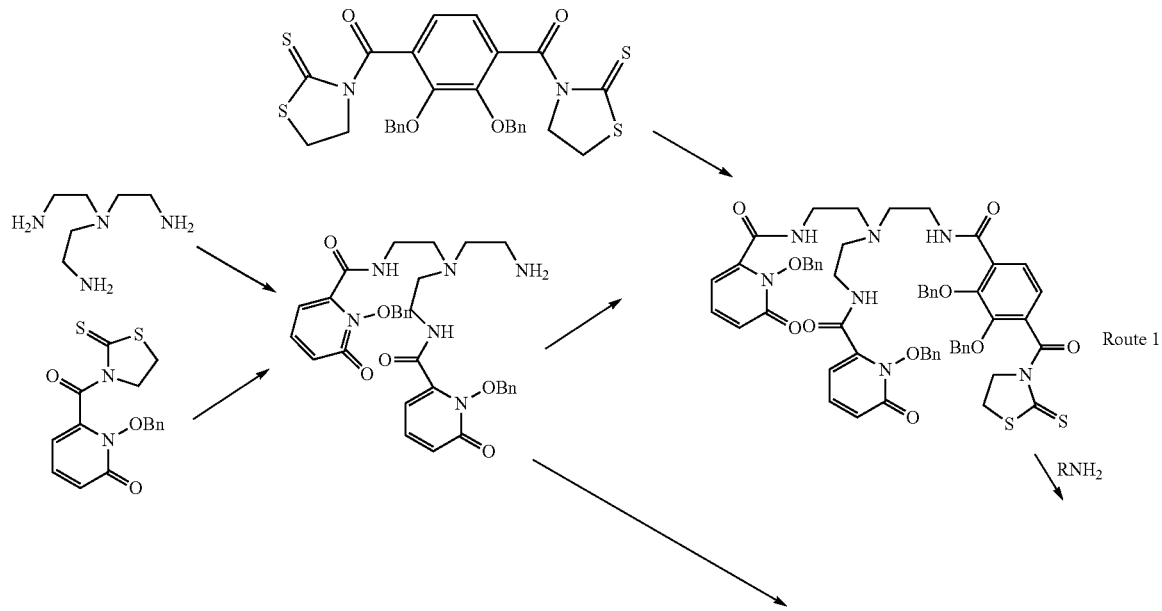

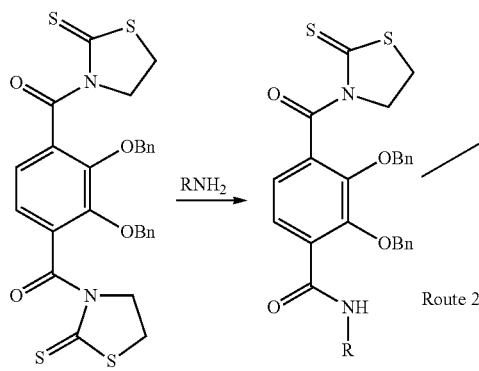
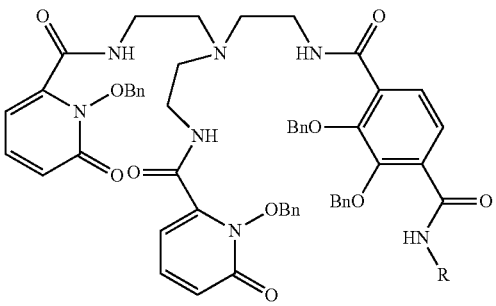

Route 2

A series of TREN-HOPO-TAM derivatives are synthesized using either route. The choice of route may depend on the choice of amine $RNH_2$.

The use of benzyl (Bn) protecting groups on TAM is generally preferable to the methyl groups previously reported (Cohen, S. M. et al., *Inorg. Chem.* 2000, 39, 4339), since the deprotection conditions are less severe, making the method amenable to a greater range of primary amines ($RNH_2$).

Synthesis of Chelating Agents Containing PEG Functionalization

In another embodiment, the invention provides poly(ethylene glycol) (PEG) functionalized chelates. In an exemplary embodiment, the invention provides derivatives of TREN-1,2-HOPO-TAM 12. The PEG group increases the rather low solubility of the parent complexes.

12

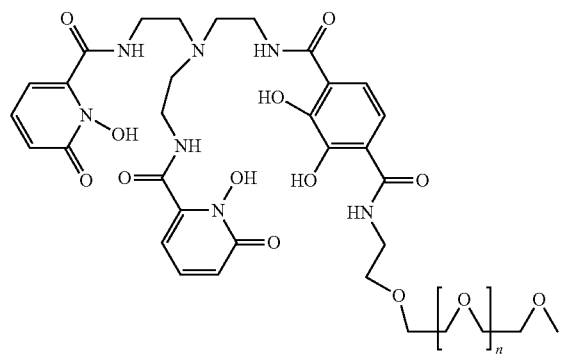

Also included in the present invention is a method of preparing a chelating agent having a polymeric backbone and at least one functionality to which a chelating ligand of the invention is bonded. Examples of suitable polymers include, but are not limited to, poly(styrene-divinylbenzene), agarose (manufactured by Bio-Rad Corp., Richmond, Calif., under the name "Affi-Gel"), and polyacrylamide. Those of skill in the art will appreciate that the method of the invention is not limited by the identity of the backbone species, and that numerous amine-, hydroxyl- and sulfhydryl-containing compounds are useful as backbones in practicing the method of the invention.

Evaluation of Ligands and Complexes

The present invention generally utilizes art recognized methods to characterize the new ligands and their metal complexes. For example, the basicity of the ligands can be assessed by determining the protonation constants ($pK_a$'s) by potentiometric titrations.

Methods of determining stability constant measurements include, but are not limited to those set forth in, Johnson, A. R. et al., *Inorg. Chem.* 2000, 39: 2652-2660; and Cohen, S. M. et al., *Inorg. Chem.* 2000, 39: 5747.

The Bjerrum method can be used for metal complex stability measurements (pH titrations of ligand and metal+ligand). Competition titrations with DTPA can be performed to determine the stability of very stable complexes where direct pH titration methods are inappropriate. Spectrophotometric techniques can be used to monitor metal-ligand complexation reactions which give rise to changes in the V is/UV spectra relative to the parent metal and ligand species. With digitally-recording automated spectrophotometeric titrators, factor analysis of the V is/UV spectra readily determined the species in solution, their individual spectra and the equilibrium constants, which interrelate them.

The emissive properties of Eu(III) and/or Tb(III), are used to reflect the rates of emissive decay in distinct sites that the metal ion occupies. Hence, luminescence titration of the Eu(III) and Tb(III) complexes of the ligands with HSA is a good method for determining biomolecule affinity (Feig, A. L. P. et al., *Chem. & Biol.* 1999, 6, 801; Chaudhuri, D. H. et al., *Biochem.* 1997, 36, 9674; Cronce, D. T. H. et al., *Biochem.* 1992, 31, 7963.

The following examples are provided to illustrate selected embodiments of the invention and are not to be construed as limiting its scope.

EXAMPLES

2-Bromopyridine-6-carboxylic Acid

A 9.7-g (0.048-mol) portion of 6-bromopyridine-2-carboxylicacid was added to a solution of 125 mL of $CF_3CO_2H$ and 18 mL of 30% $H_2O_2$ and heated to 80° C. for 6.5 h. The reaction mixture was concentrated to ca. 25 mL by rotary evaporation and then added to 1 L of water. The product immediately precipitated as a finely divided, white crystalline solid. It was isolated by filtration, washed with water, and dried in vacuum. This yielded 10.2 g (97%) of product, mp 180° C. dec.

$^1$H NMR (300 MHz, DMSO-d$_6$): δ 7.70 (t, 1H), 8.24 (dd, 1H), 8.29 (dd, 1H). Anal. Calcd for C$_6$H$_4$BrNO$_3$: C, 33.05; H, 1.85; Br, 36.65; N, 6.43. Found: C, 33.30; H, 1.88; Br. 36.37; N, 6.52.

1-Hydroxy-6-carboxy-2(1H)pyridinone

A 10.1-g (0.046 mol) portion of 2-bromopyridine-6-carboxylicAcid was dissolved in 175 mL of a 10% aqueous KOH solution, and the resulting solution was maintained at 80° C. overnight and then cooled in an ice bath and treated with 85 mL of concentrated HCl. The white suspended solid was isolated by filtration, washed with dilute HCl followed by three 15 mL portions of water, and then dried in vacuo yielding 6.21 g (86.4%), mp 216° C. dec.

An alternative route is described below: Acetic anhydride (100 ml) was mixed with 30% hydrogen peroxide solution (25 ml) with cooling; the mixture was stirred for 3 hr until a homogenous peracetic acid solution formed. To a solution of 6-hydroxy-picolinic acid (Fluka, 25 g, 0.18 mol) in a mixture of trifluoroacetic acid (150 mL) and glacial acetic acid (100 mL), the above peracetic acid solution was added slowly with stirring. (CAUTION! any solid particle in the mixture will caused vigorous oxygen release and lead to out of control of the reaction). The mixture stirred at room temperature for one 1 hr, and heated slowly to 75° C. and kept at 80° C. (oil bath temperature) for 10 hr. White precipitate formed during this period, it was collected by filtration, washed with cold methanol, and dried in a vacuum oven, yield 20.5 g (0.132 mol, 73%). mp 176-177° C.

$^1$H NMR (300 MHz, DMSO-d$_6$): δ 6.634 (dd, J$_{ortho}$=7 Hz, J$_{meta}$=1.5 Hz, 1H), 6.710 (dd, J$_{ortho}$=9.2 Hz, J$_{meta}$=1.5 Hz, 1H), 7.437 (dd, J$_{ortho}$=9, J$_{meta}$=7 Hz, 1H). $^{13}$C NMR (75 MHz, DMSO-d$_6$): δ 106.9, 120.6, 135.0, 137.3, 157.4, 163.3. IR (KBr pellet) ν 1734 (br, C=O), 1616 (m, C=O) cm$^{-1}$. Anal. Calcd (Found) for C$_6$H$_5$NO$_4$(F.W. 155.15): C, 46.46 (46.31); H, 3.25 (3.45); N, 9.03 (9.12).

1-Benzyloxy-6-carboxy-2(1H)-pyridinone (1,2-HOPOBn acid)

1-Hydroxy-6-carboxy-2(1H)-pyridinone (15.5 g, 0.1 mol) and anhydrous potassium carbonate (27.6 g, 0.2 mol) were mixed with benzyl chloride (15.2 g, 0.12 mol) in methanol (250 mL). The mixture was refluxed for 16 h, filtered, and the filtrate evaporated to dryness. The residue was dissolved in water (50 mL) and acidified with 6 N HCl to pH 2. The white precipitate was isolated by filtration, washed with cold water, and dried in vacuum, to yield 22.3 g (91%) of 1-Benzyloxy-6-carboxy-2(1H)-pyridinone, mp 176-177° C.

$^1$H NMR (300 MHz, CDCl$_3$): δ 5.269 (s, 2H), 6.546 (dd, J=1.6 Hz, J=6.7 Hz, 1H), 6.726 (dd, J=1.6 Hz, J=9.2 Hz, 1H), 7.39-7.51 (m, 6H). $^{13}$C NMR (75 MHz, DMSO-d$_6$): δ 77.9, 106.0, 124.1, 128.5, 129.1, 129.6, 133.8, 138.7, 140.5, 157.7, 161.7. Anal. Calcd (Found) for C$_{13}$H$_{11}$NO$_4$: C, 63.66 (63.75); H, 4.53 (4.55); N, 5.71 (5.52).

1,2-HOPOBn Acid Chloride

To a suspension of 1,2-HOPOBn acid (5.0 g, 20 mmol) in toluene or benzene (50-70 mL), excess of oxalyl chloride (2.0 g) was added with stirring A lot of gas bubbles evolved and the suspension turned to be clear upon the addition of a drop of DMF as catalyst. The mixture was then warmed to 40° C. (oil bath temperature) for 4-6 hr, and the solvent was moved on a rotovap to leave pale yellow oil. The residual solvent and oxallyl chloride were removed in a vacuum line (0.1 mm Hg) when the oil solidified as pale yellow crystalline solid, raw yield 5.0 g (95%). It is generally used directly for next step reaction without further purification.

$^1$H NMR (300 MHz, CDCl$_3$): δ 5.32 (s, 2H), 6.88 (d, 1H), 6.94 (d, 1H), 7.3-7.4 (m, 4H), 7.49 (m, 2H). $^{13}$C NMR (75 MHz, CDCl$_3$): δ 78.5, 112.3, 128.4, 128.6, 129.4, 130.3, 132.7, 136.4, 140.2, 158.1, 158.8.

1-Benzyloxy-6-(2-thioxothiazolidin-1-yl)-carbonyl-2 (1H)-pyridinone (1,2-HOPOBn-thiazolide)

To a solution of 1-benzyloxy-6-carboxy-2(1H)-pyridinone (4.90 g, 20 mmol), 2-mercaptothiazoline (2.62 g, 22 mmol), and a catalytic amount of 4-dimethyl-aminopyridine (DMAP) in dry THF (50 mL), was added N,N'-dicyclohexylcarbodiimide (DCC) (4.6 g, 22 mmol). After stirring overnight, the dicyclohexylurea (DCU) solids are removed by filtration the yellow filtrate is removed by rotary evaporation to give a yellow solid. Crystallization from isopropanol-methylene chloride gives the title compound (5.80 g, 83.7%) as a pale yellow powder, m.p.: 135-7° C.

$^1$H NMR (300 MHz, CDCl$_3$): δ 3.156 (t, J=7.4 Hz, 2H), 4.450 (t, J=7.4 Hz, 2H), 5.321 (s, 2H), 6.176 (dd, J=1.6 Hz, J=6.8 Hz, 1H), 6.776 (dd, J=1.6 Hz, J=9.2 Hz, 1H), 7.27-7.47 (m, 6H). $^{13}$C NMR (75 MHz, CDCl$_3$): δ 28.9, 54.4, 78.9, 124.2, 128.6, 129.3, 129.8, 133.6, 137.8, 141.5, 158.1, 159.6. Anal for C$_{17}$H$_{16}$N$_2$O$_3$S$_2$ Calcd. (Found): C, 55.47 (55.36); H, 4.07 (4.17); N, 8.08 (7.83); S, 18.51 (18.41).

1-Hydroxy-6-N-octylcarboxamide-2(1H)-pyridinone (Octyl-1,2-HOPO)

Lipophilic bidentate 1,2-HOPO ligand with long aliphatic chains were synthesized as raw models of lanthanide and actinide extractants. The general procedure for synthesizing such extractants is given below.

1,2-HOPO acid (1.00 g, 6.45 mmol) and 1,1'-carbonyldiimidazole (CDI) (1.05 g, 6.47 mmol) were stirred in dry DMF (40 mL) under N$_2$ for 2 hr. Octylamine (0.84 g, 6.46 mmol) was added to the above solution, and the mixture stirred overnight. DMF was then removed by rotary evaporation, the residue taken up in dichloromethane (50 mL). It was extracted three times with 0.1 NaOH (3×25 mL) and the combined aqueous phase reduced in volume to 20 mL by rotary evaporation. The concentrated solution was acidified with 1 M HCl to pH 2, upon which a white precipitate immediately. It was collected by filtration, washed with cold water and dried in vacuo to give a beige solid (1.10 g, 63.1%).

$^1$H NMR (300 MHz, CDCl$_3$): δ 0.878 (t, 3H, CH$_3$), 1.27-1.39 (m, 10H, CH$_2$, 1.653 (qint, 2H, CH$_2$), 3.49 (qint, 2H, CH$_2$), 7.06 (d, 1H, arom H), 7.45 (d, 1H, arom H), 9.65 (s, 1H, NH). $^{13}$C NMR (300 MHz, CDCl$_3$): δ 14.1, 22.6, 27.1, 29.2, 31.8, 113.9, 115.0, 133.0, 137.0, 156.4, 158.7. MS(FAB+): 266 (MH$^+$). Anal. Calcd (Found) for C$_{14}$H$_{22}$N$_2$O$_3$: C, 63.13 (62.71); H, 8.32 (8.47); N, 10.52 (10.63).

Preliminary extraction study indicated octyl-1,2-HOPO exhibits high specificity extractant for Pu(IV) over a wide range of acidity and ionic strength.

Carbostyril-124-1,2-HOPOBn (CS124-1,2-HOPOBn)

To a solution of carbostyril (0.174 g, 1 mmol) and dry triethylamine (0.4 ml, 4 mmol) in DMAA (20 mL) cooling with an ice bath, a solution of raw 1,2-HOPOBn acid chloride (0.58 g, 2.2 mmol) in dry $CH_2Cl_2$ (35 mL) was added dropwisely with stirring. The mixture was heated at room temperature overnight, until TLC indicated the reaction was complete. The volatiles were removed under vacuo, and the residue was loaded on a flash silica column. Elution with 2-6% methanol in methylene chloride allows the separation of the benzyl-protected precursor CS124-1,2-HOPOBn) (0.27 g, 67% based on CS-124) as a thick pale yellow oil.

$^1$H NMR (300 MHz, $CDCl_3$): δ 2.39 (s, 3H), 5.29 (s, 4H), 6.31 (s, 1H), 6.55 (dd, 1H), 6.73 (dd, 1H), 7.25-7.45 (m, 5H), 7.55 (d, 1H), 7.69 (d, 1H), 7.89 (d, 1H), 11.16 (s, 1H), 11.66 (s, 1H). $^{13}$C NMR (300 MHz, $CDCl_3$): δ 18.1, 79.2, 105.1, 106.1, 114.6, 117.2, 120.4, 123.8, 126.3, 129.2, 129.8, 130.3, 134.4, 139.8, 140.2, 144.1, 148.4, 158.1, 159.6, 162.7.

Carbostyril-124-1,2-HOPO(CS124-1,2-HOPO)

Since the 1,2-HOPO moiety is reductively sensitive to hydrogenation, most benzyl protected 1,2-HOPO ligands were deprotected under strong acidic conditions. CS124-1,2-HOPOBn (0.4 g, 1 mmol) was dissolved in concentrated HCl (12 M)/glacial acetic acid (1:1, 20 mL), and stirred at room temperature for 2 days. Removal of the solvent gives a beige residue, which was stirred with methanol to form a white slurry which was filtered to give CS124-1,2-HOPO (0.37 g, 93%) as a white powder.

$^1$H NMR (300 MHz, $CDCl_3$): δ 2.38 (s, 3H), 6.30 (s, 1H), 6.46 (dd, 1H), 6.63 (dd, 1H), 7.36 (dd, 1H), 7.45 (dd, 1H), 7.68 (d, 1H), 7.88 (d, 1H), 11.09 (s, 1H), 11.64 (s, 1H). $^{13}$C NMR (75 MHz, $CDCl_3$): δ 18.6, 104.0, 105.5, 114.5, 116.7, 118.8, 120.2, 125.7, 137.7, 139.3, 140.2, 142.1, 148.7, 157.6, 159.1, 162.1. MS (ES$^-$): 310.1 (M$^-$).

2,2-Dimethyl-3LI-1,2-HOPOBn

To a solution of 1,2-HOPOBn-thiazolide (1.22 g, 4 mmol) in dry methylene chloride (30 mL), was added neat 2,2-dimethyl-1,3-propanediamine (184 mg, 1.8 mmol). The mixture was stirred overnight, solvent removed and loaded onto a flash silica column. Elution with 2-6% methanol in methylene chloride allows the separation of the benzyl-protected precursor: 2,2-Dimethyl-3LI-1,2-HOPO-Bn (940 mg, 84.6%) as thick pale yellow oil.

$^1$H NMR (300 MHz, $CDCl_3$): δ 0.844 (s, 6H), 3.027 (d, br, 4H), 5.301 (s, 4H), 6.307 (dd, 2H), 6.635 (dd, 2H), 7.246 (dd, 2H), 7.21-7.37 (m, 6H), 7.43-7.46 (m, 4H), 7.650 (t, 2H, J=6.6 Hz). $^{13}$C NMR (75 MHz, $CDCl_3$): δ 23.2, 36.5, 45.9, 53.2, 81.5, 104.7, 122.7, 128.0, 128.7, 129.3 133.0, 137.9, 143.1, 158.1, 160.9.

2,2-Dimethyl-3LI-1,2-HOPO 2,2-Dimethyl-3LI-1,2-HOPO-Bn (557 mg, 1 mmol) was dissolved in concentrated HCl (12 M)/glacial acetic acid (1:1, 20 mL), and was stirred at room temperature for 2 days. Filtration followed by removal of the solvent gives a beige residue, which was washed with ether to give 2,2-Dimethyl-3LI-1,2-HOPO (412 mg, 92.1%) as a beige powder, m.p. 115-117° C.

$^1$H NMR (300 MHz, DMSO-$d_6$): δ 0.892 (s, 6H), 3.114 (d, 4H), 6.314 (dd, 2H), 6.573 (dd, 2H), 7.394 (dd, 2H), 8.730 (t, 2H, J=6.6 Hz). Anal for $C_{17}H_{18}N_4O_6$.3HCl.$H_2O$ (485.34) Calcd. (Found): C, 42.07 (41.95); H, 5.40 (5.67); N, 11.54 (11.29).

4LI-1,2-HOPOBn

The benzyl protected 4LI-1,2-HOPOBn was prepared following the procedure for 2,2-dimethyl-3LI-1,2-HOPO-Bn, except 1,4-butanediamine (160 mg, 1.8 mmol) was used instead of 2,2-dimethyl-1,3-propanediamine Separation and purification of the benzyl-protected precursor was performed as described above to give the desired product as pale yellow oil (77% based on amine).

$^1$H NMR (300 MHz, $CDCl_3$): δ 1.42 (s, br, 4H), 3.16 (d, br, 4H), 5.27 (s, 4H), 6.35 (dd, 2H), 6.63 (dd, 2H), 6.86 (t, br, 2H), 7.24-7.46 (m, 12H).

4LI-1,2-HOPO

4LI-1,2-HOPOBn was deprotected following the procedure of 2,2-dimethyl-3LI-1,2-HOPO, except 4LI-1,2-HOPOBn (543 mg, 1 mmol) was used instead of 2,2-dimethyl-3LI-1,2-HOPOBn. Separation and purification of the deprotected product are performed as described above to afford a beige solid (452 mg, 92.2%).

$^1$H NMR (300 MHz, DMSO-$d_6$): δ 1.52 (s, br, 4H), 3.21 (d, br, 4H), 6.26 (dd, 2H), 6.55 (dd, 2H), 7.38 (dd, 2H), 8.74 (t, 2H, J=5.6 Hz). Anal for $C_{16}H_{18}N_4O_6$.3HCl.$H_2O$, Cacld. (Found): C, 39.23 (39.52); H, 3.73 (3.69); N, 11.43 (11.27).

5LI-1,2-HOPOBn

The benzyl protected 5LI-1,2-HOPOBn was prepared following the procedure for 2,2-dimethyl-3LI-1,2-HOPO-Bn, except 1,5-pentanediamine (184 mg, 1.8 mmol) was used instead of 2,2-dimethyl-1,3-propanediamine Separation and purification of the protected precursor was performed as described above to give a pale yellow oil (0.9 g, 90% based on amine).

$^1$H NMR (300 MHz, $CDCl_3$): δ 1.18 (qin, 2H), 1.39 (qin, 4H), 3.17 (q, 4H), 5.26 (s, 4H), 6.32 (dd, 2H), 6.62 (dd, 2H), 6.78 (t, 2H), 7.26-7.45 (m, 12H). $^{13}$C NMR (75 MHz, $CDCl_3$): δ 23.4, 27.9, 39.3, 79.1, 105.9, 123.2, 128.4, 129.2, 129.9 133.2, 138.5, 142.9, 158.5, 160.3.

5LI-1,2-HOPO

5LI-1,2-HOPO was deprotected following the procedure for 2,2-dimethyl-3LI-1,2-HOPO, except 5LI-1,2-HOPOBn (557 mg, 1 mmol) was used instead of 2,2-dimethyl-3LI-1,2-HOPOBn. Separation and purification of the deprotected product was performed as described above to yield the desired product as a beige solid (344 mg, 91%).

$^1$H NMR (300 MHz, DMSO-$d_6$): δ 1.35 (qin, 2H), 1.46 (qin, 4H), 3.18 (q, 4H), 6.26 (dd, 2H), 6.55 (dd, 2H), 7.37 (dd, 2H), 8.73 (t, 2H, J=5.6). MS(FAB+): 377 (MH$^+$). Anal for $C_{17}H_{20}N_4O_6$.2HCl.$H_2O$ (467.32), Cacld. (Found): 43.69 (43.75), 5.17 (4.93), 11.98 (11.65).

$C_5H_6N[Eu(5LI-1,2-HOPO)_2]$

A solution of europium chloride hexahydrate (37 mg, 0.1 mmol) in methanol (1 mL) was added to a solution of 5LI-1,2-HOPO.2HCl.$H_2O$ (94 mg, 0.20 mmol) in methanol (5 mL) while stirring. The mixture was refluxed for 6 hr. under nitrogen, during which time the complex deposits as a white precipitate. This solid was isolated by filtration, rinsed with cold methanol, and dried to give the pyridinium salt of title complex (80 mg, 82%) as a white solid.

Anal. For EuC$_{34}$H$_{36}$N$_8$O$_{12}$.C$_5$H$_6$N, Calcd. (Found): C, 47.76 (47.45); H, 4.32 (4.22); N, 12.85 (12.67). MS (ES−): 900.1 (M$^-$).

Crystals of Eu5LI-1,2-HOPO suitable for X-ray diffraction are prepared by vapor diffusion of ether into a wet methanol solution of the complex with excess of dimethylamine. The ORTEP diagram and crystallographic data have been mentioned in introduction section.

3-Oxapentane-1,5-diamine (5LIO-amine)

This amine was available from Aldrich as hydrochloride salt form at high cost. However the following modified literature procedure was quite easy to preparation good amount of the free amine.

A mixture of 34.7 g (0.5 mol) of NaN$_3$ and catalytical amount of KI (1 g) in 75 mL of H$_2$O and 6.8 g (0.02 mol) of cetylpyridinium chloride in 42.9 g (0.3 mol) of 1,5-dichloro-3-oxapentan we refluxed and stirred for 20 h. The reaction mixture was filtered, the organic phase of the filtrate separated and the aqueous phase extracted with dichloromethane three times. The combined organic solution was extracted with 10% solution of Na$_2$S$_2$O$_3$ to removed any iodine in the organic phase. The organic phase was then loaded onto a flash silica gel plug to remove the pyridinium salt and residual water. Evaporation under vacuo at 25° C. affords 45 g of crude diazide. It was dissolved in 60 mL of 95% ethanol and hydrogenated at 25° C. (cooling with a water bath) and 50 atm in the presence of 10% Pd/C (1.5 g). Filtration of the catalyst, evaporation of the solvent, and distillation gave 25 g (80%) of 5LIO-amine: bp 48-50° C. (1 torr)].

$^1$H NMR (300 MHz, CDCl$_3$): δ 1.33 (s, br, 4H), 2.83 (t, 4H), 3.45 (t, 4H).

5LIO-1,2-HOPOBn

To a solution of 1,2-HOPO(Bn)-thiazolide (644 mg, 2.1 mmol) in dry methylene chloride (20 mL), was added neat 5LIO-amine (104 mg, 1.0 mmol). The mixture was stirred overnight, after which time the solvent was removed and the residue was loaded onto a flash silica column. Elution with 2-6% methanol in methylene chloride allowed for the separation and isolation of the benzyl-protected 5LIO-1,2-HOPO (Bn) to give a pale yellow oil (447 mg, 85% based on amine).

$^1$H NMR (500 MHz, CDCl$_3$): δ 3.22 (s, 8H, CH$_2$), 5.24 (s, 4H, benzyl CH$_2$), 6.26 (dd, J=7, 1.2 Hz, 2H, HOPO H), 6.31 (d, 2H, J=9.0 Hz, HOPO H), 7.24 (dd, 2H, J=9.0, 2 Hz, ArH), 7.26-7.45 (m, 12H, ArH), 7.74 (s, br, 2H, amideH). $^{13}$C NMR (125 MHz, CDCl$_3$): δ 38.8, 68.1, 78.2, 104.7, 121.7, 127.7, 128.3, 129.0, 132.9, 138.3, 143.2, 157.8, 160.0. MS(FAB+): 559.2 (MH$^+$).

5LIO-1,2-HOPO

5LIO-1,2-HOPOBn (558 mg, 1 mmol) was dissolved in concentrated HCl (12 M)/glacial acetic acid (1:1, 20 mL), and was stirred at room temperature for 2 days. Filtration followed by removal of the solvent gave a beige residue, which was dissolved in a minimum amount of methanol and then mixed with diethyl ether while stirring, 5LIO-1,2-HOPO precipitated, and was collected by filtration and dried under vacuum at 80° C. affording a white powder as product (340 mg, 90%).

$^1$H NMR (500 MHz, DMSO-d$_6$): δ 3.37 (q, 4H, J=6.0 Hz, CH$_2$), 3.52 (t, 4H, J=6.0 Hz, CH$_2$), 6.29 (dd, 2H, J=7.0, 1.5 Hz, HOPO H), 6.57 (dd, 2H, J=9.0, 2.0 Hz, HOPO H), 7.32 (dd, 2H, J=9.0, 2.0 Hz, HOPO H), 8.82 (t, 2H, J=5.5 Hz, amide H). $^{13}$C NMR (300 MHz, CDCl$_3$): δ 39.2, 68.0, 108.4, 120.2, 138.6, 139.7, 159.2, 161.7. MS(FAB+): 379 (MH$^+$). Anal for C$_{16}$H$_{18}$N$_4$O$_2$ (378.34), Cacld. (Found): 50.79 (50.60), 4.80 (4.99), 14.80 (14.50).

C$_5$H$_6$N [Eu-5LIO-1,2-HOPO].H$_2$O

A solution of europium chloride hexahydrate (37 mg, 0.1 mmol) in methanol (1 mL) was added to a solution of 5LIO-1,2-HOPO (76 mg, 0.20 mmol) in methanol (5 mL) while stirring. The clear solution became turbid after 2 drops of dry pyridine was added. The mixture was refluxed for 6 hr. under nitrogen, during which time the complex deposits as a white precipitate. This solid was isolated by filtration, rinsed with cold methanol, and dried to give the pyridinium salt of title complex (63 mg, 63%) as a white solid.

Anal. for EuC$_{32}$H$_{32}$N$_8$O$_{14}$.C$_5$H$_6$N.H$_2$O, Calcd. (Found): C, 44.32 (44.15); H, 4.02 (4.08); N, 12.57 (12.40). MS (ES−): 905.1 (M$^-$).

Crystals of Eu5LIO-1,2-HOPO suitable for X-ray diffraction are prepared by vapor diffusion of ether into a methanol solution of the above complex with 1 equivalent of tetramethylammonium hydroxide.

o-Phenylene-1,2-HOPOBn

To a mixture of o-phenylenediamine (0.11 g, 1 mmol) and 30% potassium carbonate solution (5 mL) in CH$_2$Cl$_2$ (20 mL) cooling with an ice bath, a solution of raw 1,2-HOPOBn acid chloride (0.64 g, 2.4 mmol) in dry CH$_2$Cl$_2$ (35 mL) was added dropwise within 1 hr with vigorous stirring. The mixture was warmed to room temperature with stirring, until TLC indicated the reaction was complete. The organic phase was separated loaded on a flash silica column. Elution with 2-4% methanol in methylene chloride allows the separation of the benzyl-protected precursor o-phenylene-1,2-HOPOBn) (0.44 g, 79% based on the free amine) as a thick pale yellow oil which was solidified upon standing overnight.

$^1$H NMR (300 MHz, CDCl$_3$): δ 5.19 (s, 4H), 6.32 (dd, 2H), 7.13-7.30 (m, 14H), 7.61 (m, 2H), 9.02 (s, 2H). $^{13}$C NMR (300 MHz, CDCl$_3$): δ 79.3, 106.4, 123.5, 124.5, 126.4, 128.4, 128.7, 129.2, 132.7, 138.4, 142.6, 158.4, 158.8. MS(FAB+): 562.2 (MH$^+$).

o-Phenylene-1,2-HOPO o-Phenylene-1,2-HOPOBn was deprotected under strong acidic condition as mentioned for CS124-1,2-HOPOBn, yield 90%.

$^1$H NMR (300 MHz, CDCl$_3$): δ 6.67 (m, 4H), 7.30 (dd, 2H), 7.47 (dd, 2H), 7.69 (dd, 2H), 10.52 (s, 2H). $^{13}$C NMR (75 MHz, CDCl$_3$): δ 106.0, 120.0, 125.5, 126.4, 130.2, 137.2, 141.5, 157.7, 159.1. MS(FAB+): 383.3 (MH$^+$). Anal for C$_{18}$H$_{14}$N$_4$O$_6$ (Mr. 382.33), Cacld. (Found): C, 56.55 (56.35); H, 3.69 (3.57); N, 14.65 (14.48).

m-Phenylene-1,2-HOPOBn

The benzyl protected m-phenylene-1,2-HOPOBn was prepared following the procedure for o-phenylene-1,2-HOPO-Bn, except m-phenylenediamine (160 mg, 1.8 mmol) was used instead of o-phenylenediamine. Separation and purification of the benzyl-protected precursor was performed as described for that of o-phenylene-1,2-HOPOBn to give the desired product as pale yellow oil (95% based on amine).

$^1$H NMR (300 MHz, CDCl$_3$): δ 5.28 (s, 4H), 6.58 (d, 2H), 6.71 (d, 2H), 7.15-7.30 (m, 14H), 7.44 (d, 2H), 7.92 (s, 1H), 9.26 (s, 2H). $^{13}$C NMR (300 MHz, CDCl$_3$): δ 79.0, 106.3, 112.0, 116.6, 122.9, 128.1, 128.8, 129.3, 129.6, 132.6, 138.1, 138.3, 142.9, 158.0, 158.7. MS(FAB+): 562.2 (MH$^+$).

m-Phenylene-1,2-HOPO 1,3-Phenylene-Bis(1,2-HOPO) was prepared following the acidic deprotection procedure of 2,2-dimethyl-3LI-1,2-HOPO as a beige solid (158 mg, 82.6%).

$^1$H NMR (300 MHz, DMSO-d$_6$): δ 6.43 (d, 2H), 6.61 (d, 2H), 7.34 (m, 1H), 7.43 (m, 4H), 8.13 (s, 1H), 10.91 (s, 2H), 11.85 (s, br, 2H). MS(FAB+): 383.3 (MH$^+$). Anal for C$_{18}$H$_{14}$N$_4$O$_6$ (Mr. 382.33), Cacld. (Found): C, 56.55 (56.26); H, 3.69 (3.61); N, 14.65 (14.45).

2-Aminomethylaniline-1,2-HOPOBn (o-BnPhen-1,2-HOPOBn)

The benzyl protected o-BnPhen-1,2-HOPOBn was prepared following the procedure for o-phenylene-1,2-HOPOBn, except 2-Aminomethyl-aniline (122 mg, 1.0 mmol) was used instead of o-phenylenediamine Separation and purification of the benzyl-protected precursor was performed as described for that of o-phenylene-1,2-HOPOBn to give the desired product as pale yellow oil which was solidified upon standing (85% based on amine).

$^1$H NMR (500 MHz, CDCl$_3$): δ 4.32 (d, 2H), 4.79 (s, 2H), 5.37 (s, 2H), 6.33 (dd, 1H), 6.40 (d, 2H), 6.69 (dd, 1H), 6.84 (d, 2H), 7.08 (m, 3H), 7.19-7.31 (m, 6H), 7.38 (d, 1H), 7.44 (m, 3H), 8.01 (d, 1H), 8.26 (s, 1H), 10.29 (s, 1H). $^{13}$C NMR (125 MHz, CDCl$_3$): δ 39.7, 78.3, 78.8, 104.7, 106.4, 122.7, 123.0, 124.2, 125.9, 127.9, 128.3, 128.6, 129.3, 129.6, 129.8, 130.8, 132.1, 132.9, 134.5, 137.7, 137.8, 141.3, 143.0, 157.9, 158.1, 158.9, 160.4. MS(FAB+): 577 (MH$^+$).

2-Aminomethylaniline-1,2-HOPO (o-BnPhen-1,2-HOPO)

o-BnPhen-1,2-HOPO) was prepared following the acidic deprotection procedure of CS124-1,2-HOPO. A beige solid was obtained as product, yield 86%.

$^1$H NMR (500 MHz, CDCl$_3$): δ 4.49 (s, 2H), 6.36 (dd, 1H), 6.58 (t, 2H), 6.66 (d, 1H), 7.26 (t, 1H), 7.32 (t, 3H), 7.39-7.52 (m, 4H), 9.28 (t, 1H), 10.62 (s, 1H). $^{13}$C NMR (125 MHz, CDCl$_3$): δ 104.0, 104.5, 119.7, 125.5, 126.4, 127.5, 127.7, 132.6, 134.2, 137.2, 142.1, 157.5, 157.6, 159.2, 160.8. MS(FAB+): 397.1 (MH$^+$). Anal for C$_{19}$H$_{16}$N$_4$O$_6$ (Mr. 396.11), Cacld. (Found): C, 57.58 (57.29); H, 4.07 (4.01); N, 14.14 (13.82).

3-Aminomethylaniline-1,2-HOPOBn (m-BnPhen-1,2-HOPOBn)

The benzyl protected o-BnPhen-1,2-HOPOBn was prepared following the procedure for o-phenylene-1,2-HOPOBn, except 3-Aminomethyl-aniline (122 mg, 1.0 mmol) was used instead of o-phenylenediamine Separation and purification of the benzyl-protected precursor was performed as described for that of o-phenylene-1,2-HOPOBn to give the desired product as pale yellow oil which was solidified upon standing (87% based on amine).

$^1$H NMR (300 MHz, CDCl$_3$): δ 4.43 (d, 2H), 5.20 (s, 2H), 6.43 (dd, 2H), 6.52 (m, 2H), 7.04 (d, 1H), 7.10-7.31 (m, 13H), 7.53 (s, br, 3H), 9.50 (s, 1H). $^{13}$C NMR (125 MHz, CDCl$_3$): δ 43.0, 78.7, 105.7, 118.9, 122.7, 123.6, 128.0, 128.7, 128.8, 128.9, 129.3, 129.6, 132.7, 137.7, 138.0, 138.2, 142.6, 142.8, 158.0, 158.3, 160.1. MS(FAB+): 577 (MH$^+$).

3-Aminomethylaniline-1,2-HOPO (m-BnPhen-1,2-HOPO)

m-BnPhen-1,2-HOPO) was prepared following the acidic deprotection procedure of CS124-1,2-HOPO. A beige solid was obtained as product, yield 86%.

$^1$H NMR (500 MHz, CDCl$_3$): δ 4.41 (s, 2H), 6.36 (d, 1H), 6.42 (d, 1H), 6.60 (t, 2H), 7.10 (d, 1H), 7.32 (t, 1H), 7.32 (t, 3H), 7.39-7.47 (m, 2H), 7.56 (d, 1H), 7.47 (s, 1H), 9.34 (t, 1H), 10.83 (s, 1H). $^{13}$C NMR (125 MHz, CDCl$_3$): δ 42.4, 103.6, 103.9, 118.3, 119.6, 119.9, 123.2, 129.0, 137.4, 137.6, 138.4, 139.5, 142.2, 142.3, 157.5, 157.6, 158.7, 160.5. MS(FAB+): 397.1 (MH$^+$). Anal for C$_{19}$H$_{16}$N$_4$O$_6$ (Mr. 396.35), Cacld. (Found): C, 57.58 (57.36); H, 4.07 (4.02); N, 14.14 (13.93).

o-Aminomethyl-benzylamine-1,2-HOPOBn (o-diBnPhen-1,2-HOPOBn)

The benzyl protected o-diBnPhen-1,2-HOPOBn was prepared following the procedure for o-phenylene-1,2-HOPOBn, except 2-Aminomethylbenzylamine was used instead of o-phenylenediamine Separation and purification of the benzyl-protected precursor was performed as described for that of o-phenylene-1,2-HOPOBn to give the desired product as pale yellow oil which was solidified upon standing (83% based on amine).

$^1$H NMR (500 MHz, CDCl$_3$): δ 4.44 (d, 4H), 5.08 (s, 4H), 6.19 (m, 4H), 7.04 (dd, 2H), 7.10-7.15 (m, 2H), 720-7.40 (m, 12H), 7.83 (d, 2H). $^{13}$C NMR (125 MHz, CDCl$_3$): δ 40.5, 78.5, 105.3, 122.5, 127.8, 128.0, 128.7, 129.4, 132.8, 135.0, 142.5, 158.0, 159.9. MS(FAB+): 591 (MH$^+$).

o-Aminomethyl-benzylamine-1,2-HOPO (o-diBnPhen-1,2-HOPO)

o-diBnPhen-1,2-HOPO was prepared following the acidic deprotection procedure of CS124-1,2-HOPO. A beige solid was obtained as product, yield 90%. $^1$H NMR (500 MHz, DMSO-d$_6$): δ 4.50 (s, 2H), 6.35 (dd, 2H), 6.58 (dd, 2H), 6.66 (d, 1H), 7.26 (dd, 2H), 7.38 (m, 4H), 9.26 (t, 2H). $^{13}$C NMR (125 MHz, CDCl$_3$): δ 103.9, 119.6, 127.3, 127.9, 135.9, 137.4, 142.3, 157.6, 160.5. MS(FAB+): 397.1 (MH$^+$). Anal for C$_{19}$H$_{16}$N$_4$O$_6$. 0.7 H$_2$O (Mr. 422.73), Cacld. (Found): C, 56.82 (57.02); H, 4.62 (4.59); N, 13.25 (12.88).

TREN-1,2-HOPOBn

The benzyl protected TREN-1,2-HOPOBn was prepared following the procedure for 2,2-dimethyl-3LI-1,2-HOPO-Bn, except tris(2-aminoethyl)amine (TREN) was used instead of 2,2-dimethyl-1,3-propanediamine Separation and purification of the benzyl-protected precursor are performed as described above to give pale yellow oil (89% based on amine).

$^1$H NMR (300 MHz, CDCl$_3$): δ 2.329 (s, br, 6H), 2.992 (d, br, 4H), 5.234 (s, 4H), 6.086 (dd, 6H), 6.365 (dd, 6H), 6.785 (t, 6H), 7.131 (dd, 6H) 7.27-7.35 (m, 12H). $^{13}$C NMR (300

MHz, CDCl$_3$): δ 37.5, 52.9, 79.0, 105.0, 122.8, 128.3, 129.0, 129.6 133.2, 138.4, 142.9, 158.1, 160.4.

TREN-1,2-HOPO

TREN-1,2-HOPO was prepared following the procedure for 2,2-dimethyl-3LI-1,2-HOPO, except TREN-1,2-HOPOBn (827 mg, 1 mmol) was used instead 2,2-dimethyl-3LI-1,2-HOPOBn. Separation and purification of the deprotected product was performed as described above affording a beige solid (502 mg, 90.1%).
$^1$H NMR (300 MHz, DMSO-d$_6$): δ 1.35 (qin, 2H), 1.47 (qin, 4H), 3.18 (q, 4H), 6.26 (dd, 2H), 6.55 (dd, 2H), 7.37 (dd, 2H), 8.73 (t, 2H, J=5.6 Hz). MS(FAB+): 558 (MH$^+$). Anal for C$_{24}$H$_{22}$N$_2$O$_9$.HCl.H$_2$O, Cacld. (Found): 47.10 (47.34), 4.94 (4.79), 16.02 (15.95).

Europium Complex with TREN-1,2-HOPO

To a solution of TREN-1,2-HOPO (61 mg, 0.10 mmol) in methanol (10 mL), was added a solution of europium chloride hexahydrate (36 mg, 0.1 mmol) in methanol (10 mL) while stirring. The clear solution becomes turbid after 2 drops of dry pyridine are added. The mixture was refluxed overnight under nitrogen, during which time the complex deposits as a white precipitate. This was filtered, rinsed with cold methanol, and dried to give the title complex (63 mg, 89%) as a white solid. Anal. for EuC$_{24}$H$_{24}$N$_2$O$_9$.H$_2$O, Calcd. (Found): C, 39.79 (40.01); H, 3.62 (3.47); N, 13.53 (13.26).

Crystals of this compound suitable for X-ray diffraction are prepared by vapor diffusion of ether into a DMF solution. The chemical formula was Eu (C$_{24}$H$_{24}$N$_7$O$_9$.C$_3$H$_7$NO)$_2$2C$_3$H$_7$NOC$_4$H$_{10}$O. The ORTEP diagram and crystallographic data and parameters for Eu-TREN-1,2-HOPO are given in introduction section.

1,3,5-Tris(bromomethyl)-2,4,6-trimethoxybenzene (MeOMEtribromide)

To a solution of 1,3,5-trimethoxybenzene (5.0 g, 30 mmol) and paraformaldehyde (3.0 g, 99 mmol) in 10 mL of acetic acid was added 22 mL of hydrogen bromide (30 wt % in HOAc). The mixture was heated at 60-70° C. in a round bottom flask equipped with a condenser cooled with ice water for 3 hrs. The mixture then was poured in 100 mL of water. The precipitate was filtered and dried. Flash chromatography using hexane/ethyl acetate (20/1) as the eluent gave the product as white powder. Yield, 1.7 g (13%); mp 126° C. $^1$H NMR (300 MHz, CDCl$_3$) δ 4.14 (s, 9H), 4.60 (s, 6H).

1,3,5-Tris-azidomethyl-2,4,6-trimethoxy-benzene (MeOMEtriazide)

The MeOME-triazide was prepared in high yield from the corresponding tetrabromide by nucleophilic substitution with azide anion. The triazide was handled with great care due to the high N:C ratio of this compound. In a typical preparation, MeOMEtribromide (0.9 g, 2 mmol) was mixed with excess of sodium azide (1.0 g, 15 mmol) in dry DMF (20 mL). The mixture was stirred at 40° C. overnight, the solvent was removed under reduced pressure at room temperature and the oily residue solidified after stirring with cold water. It was then washed thoroughly with water and air dried. Yield 0.60 g (90%).

$^1$H NMR (500 MHz, CDCl$_3$) δ 3.92 (s, 9H, methoxy CH$_3$), 4.45 (s, 6H, ArCH$_2$). $^{13}$C NMR (125 MHz, CDCl$_3$) δ 44.1, 63.2, 119.8, 160.3.

1,3,5-Bis-aminomethyl-2,4,6-trimethoxy-benzylamine (MeOMEtriaamine)

To a solution of MeOMEtriazide (0.6 g, 2 mmol) in methanol (20 mL) was added palladium on carbon (10%) catalyst (50 mg). The mixture was hydrogenated at room temperature in a Parr bomb at 500 psi overnight. The catalyst was then removed by filtration (fine glass frit) and the filtrate was evaporated under reduced pressure, yield 0.41 g (90%). The MeOMEtriaamine was directly used for the next amidation reaction.
$^1$H NMR (500 MHz, CDCl$_3$) δ 1.70 (s, 6H, ArCH$_2$), 3.81 (s, 9H, methoxy CH). $^{13}$C NMR (125 MHz, CDCl$_3$) δ 35.4, 61.7, 126.1, 156.4.

MeOME-1,HOPOBn

To a mixture of o-MeOMEtriaamine (0.13 g, 0.5 mmol) and 30% potassium carbonate solution (5 mL) in CH$_2$Cl$_2$ (20 mL) cooling with an ice bath, a solution of raw 1,2-HOPOBn acid chloride (form 0.5 g of 1,2-HOPOBn avid, 2 mmol) in dry CH$_2$Cl$_2$ (15 mL) was added dropwise within 1 hr with vigorous stirring. The mixture was warmed to room temperature with stirring, until TLC indicated the reaction was complete. The organic phase was separated loaded on a flash silica column. Elution with 2-5% methanol in methylene chloride allows the separation of the benzyl-protected precursor o-phenylene-1,2-HOPOBn) (0.34 g, 74% based on the free amine) as a thick pale yellow oil which was solidified upon standing overnight.
$^1$H NMR (300 MHz, CDCl$_3$): δ 3.61 (s, 9H, CH$_3$), 4.57 (d, 6H, ArCH$_2$), 5.25 (s, 6H), 6.40 (dd, 3H), 6.74 (dd, 3H), 6.95 (t, 3H, amide H), 7.20-7.36 (m, 15H), 7.38 (d, 3H). MS(FAB+): 937 (MH$^+$).

MeOME-1,2-HOPO

MeOME-1,2-HOPO was prepared following the acidic deprotection procedure of 2,2-dimethyl-3LI-1,2-HOPO as a beige solid, yield 83%.
$^1$H NMR (500 MHz, DMSO-d$_6$): δ 3.80 (s, 9H), 6.49 (d, 6H, ArCH$_2$), 6.38 (d, 3H), 6.59 (dd, 3H), 7.37 (dd, 3H), 9.06 (t, 3H, amideH). $^{13}$C NMR (125 MHz, DMSO-d$_6$) δ 33.5, 62.3, 105.1, 118.9, 120.5, 136.6, 141.5, 157.3, 159.1, 159.8. MS(FAB+): 667 (MH$^+$). Anal for C$_{30}$H$_{30}$N$_6$O$_{12}$.H$_2$O (Mr. 684.606), Cacld. (Found): C, 52.63 (52.66); H, 4.71 (4.64); N, 12.27 (12.42).

H(2,2)-1,2-HOPOBn

The benzyl protected H(2,2)-1,2-HOPOBn was prepared following the procedure for 2,2-dimethyl-3LI-1,2-HOPOBn, except H(2,2) amine (or PENTEN, 198 mg, 0.9 mmol) was used instead of 2,2-dimethyl-1,3-propanediamine Separation and purification of the benzyl-protected precursor was performed as described above affording a pale yellow oil (893 mg, 87% based on amine).
$^1$H NMR (300 MHz, CDCl$_3$): δ 1.77 (s, 2H), 2.20 (t, 8H), 3.02 (d, br, 8H), 5.28 (s, 8H), 6.15 (dd, 4H), 6.59 (dd, 4H), 7.21 (dd, 4H), 7.30-7.34 (m, 20H), 7.47-7.51 (m, 8H). $^{13}$C NMR (300 MHz, CDCl$_3$): δ 37.2, 51.8, 52.6, 79.0, 105.0, 123.1, 128.3, 129.2, 130.0 133.2, 138.1, 142.8, 158.2, 160.5.

H(2,2)-1,2-HOPO

H(2,2)-1,2-HOPO was prepared following the procedure for 2,2-dimethyl-3LI-1,2-HOPO, except H(2,2)-1,2-HOPOBn (856 mg, 0.75 mmol) was used instead of 2,2-dimethyl-3LI-1,2-HOPOBn. Separation and purification of the deprotected product was performed as described above yield a beige solid (529 mg, 81%).

$^1$H NMR (300 MHz, DMSO-$d_6$): δ 3.15 (s, br, 8H), 3.55 (s, br, 4H), 3.62 (s, br, 8H), 6.42 (d, 2H), 6.59 (dd, 2H), 7.40 (dd, 2H), 9.05 (t, 2H, J=5.6 Hz). Anal for $C_{34}H_{40}N_{10}O_{12}$·2HCl·$H_2O$, Cacld. (Found): C, 46.84 (46.75); H, 5.08 (5.10); N, 16.07 (16.05).

H(3,2)-1,2-HOPOBn

The benzyl protected H(3,2)-1,2-HOPOBn was prepared following the procedure for H(2,2)-1,2-HOPOBn, except N,N,N',N'-Tetrakis-(2-amino-ethyl)-propane-1,3-diamine, (H(3,2) amine 220 mg, 0.9 mmol) was used instead of H(2,2)-amine. Separation and purification of the benzyl-protected precursor was performed as described above affording a pale yellow oil (0.73 g, 71% based on amine).

$^1$H NMR (500 MHz, CDCl$_3$): δ 1.03 (s, 2H), 1.87 (s, 4H), 2.13 (s, 8H), 3.08 (s, br, 8H), 5.22 (s, 8H), 6.15 (d, 4H), 6.52 (d, 4H), 7.15 (t, 4H), 7.30-7.34 (m, 12H), 7.44 (d, 8H), 7.49 (s, 4H). $^{13}$C NMR (125 MHz, CDCl$_3$): δ 24.2, 37.3, 51.0, 52.3, 78.8, 105.0, 122.9, 128.1, 128.9, 129.7, 133.1, 138.0, 142.8, 158.1, 160.4. MS(FAB+, DTT/DTE): 1155.6 (MH$^+$).

H(3,2)-1,2-HOPO

H(3,2)-1,2-HOPO was prepared following the strong acidic deprotection procedure for H(2,2)-1,2-HOPO, except H(2,2)-1,2-HOPOBn (0.87 g, 0.75 mmol) was used instead of H(2,2)-1,2-HOPOBn. Separation and purification of the deprotected product was performed as described above yield a beige solid (0.52 g, 87%).

$^1$H NMR (500 MHz, DMSO-$d_6$): δ 1.67 (s, br, 2H), 2.70-2.85 (m, 12H), 3.07 (s, br, 4H), 5.97 (dd, 4H), 6.02 (dd, 4H), 6.67 (dd, 4H). $^1$H NMR (500 MHz, CD$_3$OD): δ 20.5, 36.3, 51.7, 54.7, 109.9, 121.5, 138.8, 140.7, 160.3, 163.8. Anal for $C_{35}H_{42}N_{10}O_{12}$·2HCl·1.5$H_2O$ (894.714), Cacld. (Found): C, 46.98 (47.19); H, 5.29 (5.22); N, 15.66 (15.55). MS (ES$^-$, MeOH): 793 (M$^-$).

H(4,2)-1,2-HOPOBn

The benzyl protected H(4,2)-1,2-HOPOBn was prepared following the procedure for H(2,2)-1,2-HOPOBn, except N,N,N',N'-Tetrakis-(2-amino-ethyl)-butane-1,4-diamine, (H(4,2) amine 234 mg, 0.9 mmol) was used instead of H(2,2)-amine. Separation and purification of the benzyl-protected precursor was performed as described above affording a pale yellow oil (0.72 g, 68% based on amine).

$^1$H NMR (500 MHz, CDCl$_3$): δ 0.85 (s, 4H), 1.95 (s, 4H), 2.29 (s, 8H), 3.15 (s, br, 8H), 5.24 (s, 8H), 6.18 (s, 4H), 6.50 (dd, 4H), 7.14 (m, 4H), 7.30-7.34 (m, 12H), 7.43-7.50 (m, 12H). $^{13}$C NMR (125 MHz, CDCl$_3$): δ 23.9, 37.4, 52.1, 53.0, 78.8, 105.0, 122.9, 128.1, 128.9, 129.7, 133.1, 137.8, 142.9, 158.1, 160.3. MS(FAB+, DTT/DTE): 1169.5 (MH$^+$).

H(4,2)-1,2-HOPO

H(4,2)-1,2-HOPO was prepared following the strong acidic deprotection procedure for H(2,2)-1,2-HOPO. Separation and purification of the deprotected product was performed as described above yield a beige solid (0.42 g, 90%).

$^1$H NMR (500 MHz, DMSO-$d_6$): δ 1.81 (s, br, 4H), 3.15 (s, 4H), 3.25 (s, 8H), 3.55 (s, 8H), 6.43 (d, 4H), 6.59 (d, 4H), 7.40 (dd, 4H), 9.13 (t, 4H), 10.96 (s, br, 4H). $^1$H NMR (100 MHz, CD$_3$OD): δ 22.1, 36.3, 49.8, 54.3, 109.7, 121.7, 139.1, 140.9, 160.3, 163.7. Anal for $C_{36}H_{44}N_{10}O_{12}$·2HCl·2.5$H_2O$ (926.76), Cacld. (Found): C, 46.66 (46.82); H, 5.54 (5.23); N, 15.11 (14.89). MS (ES$^-$, MeOH): 807.3 (M$^-$).

H(5O,2)-CBZ

Several approaches were tried to synthesize the N,N,N',N'-Tetrakis-(2-amino-ethyl)-3-oxapentane-1,5-diamine[H(5O,2)-amine]. It was found that the reaction of 5LIO-amine with CBZ-aziridine provides clean H(5O,2)-CBZ.

5LIO-amine (0.21 g, 2 mmol) and CbZ-aziridine (1.77 g, 10 mmol) were mixed in ten-butanol (30 mL) at room temperature under N$_2$. The mixture was stirred under a N$_2$ atmosphere at 80° C. for 16 hrs, when TLC showed the completeness of the reaction. The volatile were removed under vacuum and the residue was dissolved in dichloromethane. The appropriate fractions of a gradient flash silica gel column (1-7% methanol in dichloromethane) were collected and evaporated to dryness to give a pale beige thick oil, yield: 1.28 g, 79%.

$^1$H NMR (300 MHz, CDCl$_3$): δ 2.53 (s, br, 12H), 3.17 (s, br, 4H), 3.83 (s, br, 8H), 5.04 (s, 8H), 7.29 (s, br, 20H). $^{13}$C NMR (300 MHz, CDCl$_3$): δ 38.8, 53.0, 53.6, 69.3, 128.0, 128.1, 128.4, 136.6, 156.4. MS(FAB+, DTT/DTE): 813.5 (MH$^+$).

H(5O,2)-amine

H(5O,2)CBZ (0.83 g, 1 mmol) and 0.1 g of Pd/C catalyst (palladium, 10 wt. & on activated carbon (Aldrich)) were combined in methanol (25 mL). The mixture was hydrogenated (500 psi pressure, room temperature) overnight in a Parr bomb. After removing the catalyst by filtration, and the filtrate was evaporated to dryness to leave pale yellow oil as product, yield 0.23 g (84%).

$^1$H NMR (500 MHz, DMSO-$d_6$): δ: 0.84 (t, 4H), 0.90 (t, 8H), 1.10 (t, 8H), 1.66 (t, 4H). $^{13}$C NMR (500 MHz, CDCl$_3$) δ: 38.6, 53.4, 53.9, 70.1.

H(5O,2)-1,2-HOPOBn

The benzyl protected H(5O,2)-1,2-HOPOBn was prepared following the procedure for H(2,2)-1,2-HOPOBn, except H(5O,2) amine (140 mg, 0.5 mmol) was used instead of H(2,2)-amine Separation and purification were performed as described for H(2,2)-1,2-HOPOBn affording a pale yellow oil (0.42 g, 71% based on amine).

$^1$H NMR (300 MHz, CDCl$_3$): δ 2.14 (s, br, 4H), 2.32 (s, br, 8H), 2.83 (s, br, 4H), 3.06 (s, br, 8H), 5.15 (s, 8H), 6.05 (s, 4H), 6.34 (s, 4H), 7.04 (s, 4H), 7.20 (s, br, 12H), 7.32 (s, br, 8H). 7.63 (s, br, 4H). $^{13}$C NMR (300 MHz, CDCl$_3$): δ 37.3, 52.0, 52.7, 78.8, 104.8, 122.9, 128.1, 128.9, 129.7, 133.1, 138.0, 143.0, 158.1, 160.3. MS(FAB+, DTT/DTE): 1185.6 (MH$^+$).

H(5O,2)-1,2-HOPO

H(2,2)-1,2-HOPOBn was deprotected following the procedure for H(2,2)-1,2-HOPO. Separation and purification of the deprotected product was performed as described above yield a beige solid (81%).

¹H NMR (500 MHz, DMSO-d₆): δ 3.40 (s, br, 8H), 3.52 (s, br, 4H), 3.70 (s, br, 8H), 3.86 (s, br, 4H), 6.41 (d, 4H), 6.60 (d, 4H), 7.40 (dd, 4H), 9.11 (t, 2H, J=5.6 Hz), 10.48 (s, 4H). MS(FAB+, DTT/DTE): 824.3 (MH⁺). Anal for $C_{36}H_{44}N_{10}O_{13}$·2HCl·H₂O, Cacld. (Found): C, 47.22 (47.54); H, 5.28 (5.35); N, 15.30 (14.95).

H(8O2,2)-CBZ

H(8O2,2)-CBZ was prepared following the procedure for H(5O,2)CBZ, except 2-[2-(2-Amino-ethoxy)-ethoxy]-ethyl-amine (0.15 g, 1 mmol) was used instead of 5LIO-amine Separation and purification of the deprotected product was performed as described for H(5O,2)-amine yielding pale yellow oil, yield: 0.64 g, 74%.

¹H NMR (300 MHz, CDCl₃): δ 2.53 (s, br, 12H), 3.16 (s, br, 8H), 3.23 (s, br, 4H), 3.35 (s, br, 4H), 5.03 (s, 8H), 7.28 (s, br, 20H). ¹³C NMR (300 MHz, CDCl₃): δ 38.8, 52.6, 53.6, 66.3, 69.2, 69.9, 127.8, 128.0, 128.3, 136.6, 156.5. MS(FAB+, DTT/DTE): 857.5 (MH⁺).

H(8O2,2)-amine

H(8O,2)CBZ (0.86 g, 1 mmol) and 0.1 g of Pd/C catalyst (palladium, 10 wt. & on activated carbon (Aldrich)) were combined in methanol (25 mL). The mixture was hydrogenated (500 psi pressure, room temperature) overnight in a Parr bomb. After removing the catalyst by filtration, and the filtrate was evaporated to dryness to leave pale yellow oil as product, yield 0.27 g (85%).

¹H NMR (300 MHz, D₂O) δ 2.49 (t, 4H), 2.54 (t, 8H), 2.78 (t, 8H), 3.34 (t, 4H), 3.40 (t, 4H). ¹³C NMR (500 MHz, CDCl₃) δ 36.9, 51.3, 51.7, 68.1, 69.3. MS(FAB+): 321.3 (MH⁺).

H(8O2,2)-1,2-HOPOBn

The benzyl protected H(8O2,2)-1,2-HOPOBn was prepared following the procedure for H(2,2)-1,2-HOPOBn, except H(8O2,2) amine (0.16 g, 0.5 mmol) was used instead of H(2,2)-amine Separation and purification were performed as described for H(2,2)-1,2-HOPOBn affording a pale yellow oil (0.41 g, 68% based on amine).

¹H NMR (300 MHz, CDCl₃): δ 2.31 (s, br, 4H), 2.42 (s, br, 8H), 2.63 (s, br, 4H), 2.85 (s, br, 4H), 3.14 (s, br, 8H), 5.32 (s, 8H), 6.20 (d, 4H), 6.48 (d, 4H), 7.08 (s, 4H), 7.34 (s, br, 16H), 7.50 (s, br, 8H). ¹³C NMR (300 MHz, CDCl₃): δ 37.4, 52.2, 53.0, 68.8, 69.0, 79.0, 104.9, 123.0, 129.1, 130.1, 133.3, 138.2, 143.2, 158.2, 160.4. MS(FAB+, NBA): 1229.7 (MH⁺).

H(8O2,2)-1,2-HOPO

H(8O2,2)-1,2-HOPOBn was deprotected following the procedure for H(2,2)-1,2-HOPO. Separation and purification of the deprotected product was performed as described above yield a beige solid (81%).

¹H NMR (500 MHz, DMSO-d₆): δ 3.36 (s, br, 8H), 3.47 (s, br, 4H), 3.62 (s, br, 4H), 3.67 (q, br, 8H), 3.85 (s, br, 4H), 6.43 (dd, 4H), 6.60 (dd, 4H), 7.41 (dd, 4H), 9.11 (t, 2H, J=5.6 Hz), 10.56 (s, 4H). ¹³C NMR (125 MHz, CD₃OD): δ 36.4, 49.3, 55.0, 66.0, 71.5, 110.2, 121.0, 139.0, 141.1, 159.9, 163.2. MS(FAB+, NBA): 869 (MH⁺). Anal for $C_{38}H_{48}N_{10}O_{14}$·2HCl·2.5H₂O (986.81), Cacld. (Found): C, 46.25 (46.69); H, 5.62 (5.71); N, 14.19 (13.89).

BocLys-H(2,2)-1,2-HOPOBn

To a solution of lysH(2,2)-amine {[5-Amino-6-((2-amino-ethyl)-{2-[bis-(2-amino-ethyl)-amino]-ethyl}-amino)-hexyl]-carbamic acid tert-butyl ester} (200 mg, 0.5 mmol) in dichloromethane (20 mL) 2 mL of 40% potassium carbonate solution was added. The mixture was cooled with an ice bath and vigorously stirred. A solution of raw 1,2-HOPOBn acid chloride (form 0.75 g 1,2-HOPOBn acid, 3 mmol) in dichloromethane (20 mL) was added slowly via a teflon tube equipped with a glass capillary tip over a period of 1 hr. The reaction mixture was allowed to warm to room temperature and stirred overnight. The mixture was then washed with 1 M HCL (20 mL), and saline (20 mL) successively and loaded onto a flash silica column. Elution with 2-8% methanol in methylene chloride allows the separation of the benzyl-protected precursor LysH(2,2)-1,2-HOPOBn as beige foam, yield 70%.

¹H NMR (300 MHz, DMSO-d₆): δ 1.15 (s, br, 4H), 1.41 (s, 9H, BocH), 1.9-2.8 (m, 14H), 2.8-3.3 (m, 8H), 3.79 (s, br, 1H), 4.90-5.40 (m, 8H), 6.03 (s, 1H), 6.17 (d, 3H), 6.53 (d, 1H), 6.60 (d, 3H), 6.94 (d, 1H), 7.0-7.4 (m, 19H), 7.4-7.5 (m, 8H), 7.71 (s, 1H, NH). ¹³C NMR (125 MHz, CDCl₃): δ 22.8, 28.2, 29.3, 31.9, 37.4, 37.5, 39.8, 48.7, 51.5, 51.9, 52.8, 53.3, 53.7, 59.0, 78.6, 79.0, 104.6, 105.0, 123/1, 128.3, 129.1, 129.7, 129.9, 130.0, 133.2, 133.3, 137.9, 138.1, 142.9, 143.1, 155.9, 158.1, 158.2160.5, 160.7. MS(FAB+, NBA): 1312 (MH⁺).

Lys-H(2,2)-1,2-HOPO

BocLysH(2,2)-1,2-HOPOBn was deprotected following the procedure for H(2,2)-1,2-HOPO. Separation and purification of the deprotected product was performed as described above yield a beige solid (81%).

¹H NMR (300 MHz, DMSO-d₆): δ 1.2-1.7 (m, br, 6H), 2.74 (s, br, 3H), 3.05 (s, br, 3H), 3.15 (s, br, 5H), 3.55 (s, br, 3H), 3.61 (s, br, 6H), 4.15 (s, br, 1H), 6.30-6.45 (m, 4H), 6.60 (d, 4H), 7.39 (m, 5H), 7.88 (s, br, 3H), 8.85 (s, br, 1H), 9.00 (s, br, 1H), 9.06 (s, br, 2H). MS(FAB+, NBA): 851 (MH⁺). Anal for $C_{38}H_{49}N_{11}O_{12}$·2HCl·H₂O·2CH₃OH, Cacld. (Found): C, 47.72 (47.60); H, 6.11 (6.17); N, 15.30 (15.34)

LysEtGlutar-H(2,2)-1,2-HOPOBn

To a cooled solution of BocLysH(2,2)-1,2-HOPOBn (260 mg, 0.2 mmol) in 2 mL dichloromethane (with an ice bath) 2 mL of trifluoroacetic acid was added neatly. The mixture was stirred for 4 hrs then evaporated to dryness at room temperature. TLC confirms the BOC group was deprotected completely. The residue was dissolved in dry THF (20 mL), dry triethylamine (0.5 mL) was added while cooling with an ice bath. To this cold mixture, excess of ethyl glutarate N-hydroxysuccinimide ester (100 mg, 0.4 mmol) was added under nitrogen. The mixture was stirred for 4 hrs and the volatiles were removed under vacuum. The residue was dissolved in dichloromethane and loaded onto a flash silica column. Elution with 2-8% methanol in methylene chloride allows the separation of the benzyl-protected precursor LysEtGlutarH(2,2)-1,2-HOPOBn as beige foam, yield 70%.

¹H NMR (300 MHz, DMSO-d₆): δ 1.09 (s, br, 4H), 1.20 (t, 3H), 1.25 (t, 4H), 1.84 (t, 2H), 2.02 (m, 2H), 2.17 (t, 6H), 2.28 (t, 6H), 2.98-3.1 (m, 8H), 3.78 (s, br, 1H), 4.05 (q, 2H), 5.10-5.40 (m, 8H), 6.03 (s, 1H), 6.16 (d, 3H), 6.45 (s, 1H), 6.51 (d, 1H), 6.58 (d, 3H), 7.15 (dd, 1H), 7.18-7.40 (m, 18H), 7.40-7.51 (m, 8H), 8.00 (s, 1H, NH). ¹³C NMR (125 MHz, CDCl₃): δ 14.4, 21.2, 23.2, 25.5, 28.9, 31.9, 33.7, 35.5, 37.7, 38.2, 39.0, 46.0, 49.1, 50.4, 52.1, 53.2, 54.5, 59.9, 60.6, 79.4, 105.1, 105.6, 123.3, 123.5, 128.8, 129.6, 130.3, 130.4, 130.6, 133.7, 133.8, 138.7, 143.4, 143.7, 143.8, 158.7, 158.8, 161.0, 161.2, 161.5, 173.0, 173.5. MS(FAB+, NBA): 1354 (MH$^+$).

LysGlutar-H(2,2)-1,2-HOPO

The deprotection of LysEtGlutar-H(2,2)-1,2-HOPOBn was performed in two steps. The first step was the saponification. The hydrolyzed LysGlutar-H(2,2)-1,2-HOPOBn was then deprotected under strong acidic condition as mentioned for LysH(2,2)-1,2-HOPOBn.

To a cooled solution of LysEtGlutar-H(2,2)-1,2-HOPOBn (0.27 g, 0.2 mmol) in 5 mL methanol (with an ice bath) 2 mL of KOH solution (1 M) was added. The mixture was stirred for 4 hrs when TLC confirms the hydrolysis of ester was complete. The mixture was evaporated to dryness at room temperature and the residue was dissolved in water (10 mL). The hydrolyzed LysGlutar-H(2,2)-1,2-HOPOBn was precipitated upon acidification with HCl (1 M), it was collected, rinse with cold water and further deprotected under strong acidic condition as mentioned above yield a beige solid (71%). $^1$H NMR (300 MHz, DMSO-d$_6$): δ 1.37 (s, br, 4H), 1.67 (t, 7H), 1.84 (t, 2H), 2.03 (m, 2H), 2.17 (t, 6H), 2.28 (t, 6H), 2.98-3.1 (m, 8H), 3.78 (s, br, 1H), 4.05 (q, 2H), 6.41 (m, 4H), 6.60 (m, 4H), 7.39 (m, 4H), 7.78 (t, 1H), 8.83 (m, 1H), 8.80 (m, 1H), 9.05 (t, 2H). MS(FAB+, NBA): 966.4 (MH$^+$). Anal for $C_{43}H_{55}N_{11}O_{15} \cdot HCl \cdot 4H_2O$ (1074.48), Cacld. (Found): C, 48.07 (48.34); H, 6.00 (6.09); N, 14.34 (14.00)

3,4,3-LI-1,2-HOPOBn

To a solution of spermine (1.01 g, 5 mmol) in dichloromethane (50 mL) 10 mL of 40% potassium carbonate was added. The mixture was cooled with an ice bath and vigorously stirred. A solution of raw 1,2-HOPOBn acid chloride (form 5.4 g 1,2-HOPOBn acid, 25 mmol) in dichloromethane (50 mL) was added slowly via a Teflon tube equipped with a glass capillary tip over a period of 1 hr. The reaction mixture was allowed to warm to room temperature and stirred overnight. The mixture was then washed with 1 M NaOH (100 mL), 1 M HCL (100 mL), and saline (100 mL) successively. The organic phase was loaded onto a flash silica column. Elution with 2-6% methanol in methylene chloride allows the separation of the benzyl-protected precursor 3,4,3-LI-1,2-HOPOBn as white foam, yield 80%.

$^1$H NMR (400 MHz, DMSO-d$_6$): δ 0.4-1.8 (m, 16H), 2.8-3.6 (m, 24H), 4.8-5.1 (m, 2H), 4.88-5.05 (m, 2H), 5.15-5.30 (m, 4H), 5.30-5.45 (m, 2H), 6.00-6.46 (m, 4H), 6.55-6.70 (m, 4H), 7.25-7.55 (m, 24H), 8.72-8.95 (m, 2H, NH). MS(FAB+): 1111.5 (MH$^+$).

3,4,3-LI-1,2-HOPO

The precursor 3,4,3-LI-1,2-HOPOBn was deprotected with 1:1 HCl (37%)/glacial HOAc for 2 days. The deprotection time could be reduced to few hours if elevated temperature (up to 50° C.) was used. All the volatiles were removed in vacuo, the residue was dissolved in minimum amount of methanol and precipitated with ether. The product was filtered and dried under vacuum, yield 91%.

$^1$H NMR (400 MHz, DMSO-d$_6$): δ 0.4-1.7 (m, 16H), 2.8-3.6 (m, 24H), 6.1-6.25 (m, 6H), 6.25-6.35 (m, 2H), 6.45-6.55 (m, 8H), 7.31-7.42 (m, 4H), 8.822 (q, 1H). 8.912 (q, 1H). MS(FAB+): 751 (MH$^+$). Anal for $C_{34}H_{38}N_8O_{12} \cdot H_2O \cdot 2HCl$ (841.68), Calcd. (found): C, 48.52 (48.16); H, 5.03 (4.82); N, 13.31 (13.23).

Synthesis of 1,2-HOPO Functional Polystyrene resin 1,2-HOPO acid (700 mg) and CDI were stirred in DMF under nitrogen for 2 hr. The dien Merrifield resin (Suzuki, T. M.; Yokoyama, T. Polyhedron 1984, 3, 939-945) was added, and the suspension stirred for 4 days. The resin was collected by filtration and washed with methanol (3×50 mL) and acetone (3×50 mL), then dried in vacuo at 70° C., yield 60%. The resin was then treated with 10 mL concentrated sulfuric acid containing catalytic amount of silver sulfate (50 mg) for 4 hr. The sulfonated resin was collected by filtration, washed with anhydrous dioxane (3×50 mL), methanol (3×50 mL), and water (4×50 mL) successively. The product was then dried in vacuo at 70° C. for 4 hr. IR(KBr pellet) ν 1653 (s, C=O) cm$^{-1}$. Anal. Found: C, 80.15; H, 7.32, N, 5.39.

Synthesis of Functional Water Soluble Polymer Bearing 1,2-HOPO Units

To a solution of 1.7 g commercially available water soluble polyamine polymer, PEI (average molecular weight=30 K Dalton) in dry DMF (50 mL), was added 3.46 g of 1,2-HOPOBn-thiazolide. The solution was stirred at room temperature for 24 h. The solvent was removed and the residue was dissolved in 50 mL of water containing 1 mL of glacial acetic acid. The solution was extracted with methylene chloride 3 times to remove the byproducts and evaporated to dryness. The residue was dissolved in 20 mL of a 1:1 mixture of glacial acetic acid and hydrochloric acid (37%). The mixture was stirred at room temperature for 2 days, and evaporated to dryness, Yield: 85% to 90%. Initial testing indicated this water-soluble polymer shows strong affinity towards lanthanide and actinides ions.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:
1. A compound having the structure:

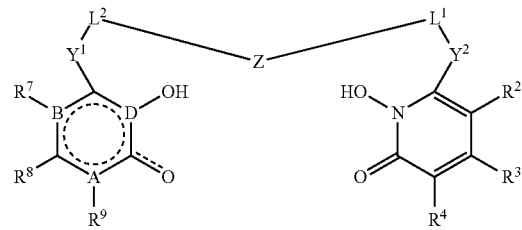

wherein
R$^2$, R$^3$, and R$^4$ are members independently selected from H, an aryl group substituent, a linker to a scaffold moiety, and a linker to a functional moiety;
R$^7$, R$^8$, and R$^9$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, halogen, CN, CF$_3$, —C(O)R$^{17}$, —SO$_2$NR$^{17}$R$^{18}$, —NR$^{17}$R$^{18}$, —OR$^{17}$, —S(O)$_2$R$^{17}$, —COOR$^{17}$, —S(O)$_2$OR$^{17}$, —OC(O)R$^{17}$, —C(O)NR$^{17}$R$^{18}$, —NR$^{17}$C(O)R$^{18}$, —NR$^{17}$SO$_2$R$^{18}$, —NO$_2$, a linker to a functional moiety, and a linker to a scaffold moiety, wherein
- at least two of R$^7$, R$^8$, and R$^9$ are optionally joined to form a ring system which is a member selected from substituted or unsubstituted cycloalkyl, substituted or unsubstituted heterocycloalkyl, substituted or unsubstituted aryl, and substituted or unsubstituted heteroaryl;
- R$^{17}$ and R$^{18}$ are each members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, a linker to a functional moiety, and a linker to a scaffold moiety; and R$^{17}$ and R$^{18}$, together with the atoms to which they are attached, are optionally joined to form a 5- to 7-membered ring;

A and B are members independently selected from carbon, nitrogen, sulfur, and oxygen;
D is a member selected from carbon and nitrogen;
wherein if A is oxygen or sulfur, R$^9$ is not present;
wherein if B is oxygen or sulfur, R$^7$ is not present;
Z is a member selected from substituted or unsubstituted alkyl, substituted or unsubstituted heteroalkyl, substituted or unsubstituted aryl, substituted or unsubstituted heteroaryl, substituted or unsubstituted heterocycloalkyl, N, NR$^{30}$, O, S, and CR$^{31}$R$^{32}$,
  wherein R$^{30}$, R$^{31}$, and R$^{32}$ are members independently selected from H, substituted or unsubstituted alkyl, substituted or unsubstituted heteroalkyl, substituted or unsubstituted aryl, substituted or unsubstituted heteroaryl, and substituted or unsubstituted heterocycloalkyl;
Y$^1$ and Y$^2$ are linker moieties, which are members independently selected from —C(O), —C(O)NR$^5$—, —C(O)O—, —C(O)S—, and —C(O)CR$^{20}$R$^{21}$,
  wherein R$^5$, R$^{20}$, and R$^{21}$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and a functional moiety; and
L$^1$ and L$^2$ are linker groups, which are members independently selected from a bond, substituted or unsubstituted alkyl, substituted or unsubstituted heteroalkyl, substituted or unsubstituted aryl, substituted or unsubstituted heteroaryl, and substituted or unsubstituted heterocycloalkyl;
wherein at least one of Z, L$^1$, and L$^2$ is substituted with a moiety having the structure:

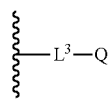

wherein
  L$^3$ is a linker group, which is a member selected from a bond, substituted or unsubstituted alkyl, substituted or unsubstituted heteroalkyl, substituted or unsubstituted aryl, substituted or unsubstituted heteroaryl, and substituted or unsubstituted heterocycloalkyl;

O has the structure:

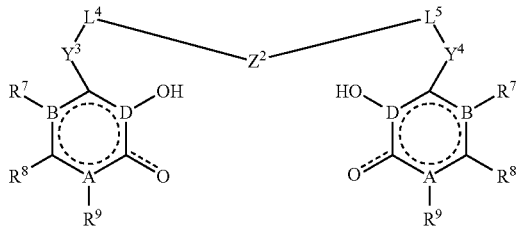

wherein
  Z$^2$ is a member selected from substituted or unsubstituted alkyl, substituted or unsubstituted heteroalkyl, substituted or unsubstituted aryl, substituted or unsubstituted heteroaryl, substituted or unsubstituted heterocycloalkyl, N, NR$^{30}$, O, S, and CR$^{31}$R$^{32}$,
  Y$^3$ and Y$^4$ are linker moieties, which are members independently selected from —C(O), —C(O)NR$^5$—, —C(O)O—, —C(O)S—, and —C(O)CR$^{20}$R$^{21}$,
  L$^4$ and L$^5$ are linker groups, which are members independently selected from a bond, substituted or unsubstituted alkyl, substituted or unsubstituted heteroalkyl, substituted or unsubstituted aryl, substituted or unsubstituted heteroaryl, and substituted or unsubstituted heterocycloalkyl; and
  one of Z$^2$, L$^4$, and L$^5$ is linked to L$^3$;
wherein said compound is substituted with at least one functional moiety having the structure:

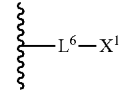

wherein
L$^6$ is a linker group, which is a member selected from substituted or unsubstituted alkyl, substituted or unsubstituted heteroalkyl, substituted or unsubstituted heterocycloalkyl, substituted or unsubstituted aryl, and substituted or unsubstituted heteroaryl; and
X$^1$ is a member selected from a reactive functional group and a targeting moiety.

2. The compound according to claim 1, wherein the scaffold moiety is a member selected from substituted or unsubstituted alkyl and substituted or unsubstituted heteroalkyl.

3. The compound according to claim 1, wherein at least one of Z, Y$^1$, Y$^2$, L$^1$, and L$^2$ is substituted with a functional moiety.

4. The compound according to claim 1, wherein Z is O, and L and L$^2$ are each ethyl.

5. The compound according to claim 1, wherein said targeting moiety comprises a member selected from a small-molecule ligand, a peptide, a protein, a fusion protein, an enzyme, an antibody, an antibody fragment, an antigen, a nucleic acid, a carbohydrate, a lipid, and a pharmacologically active molecule.

6. The compound according to claim 1, wherein said reactive functional group is a member selected from —OH, —SH, —NH$_2$, —C(O)NHNH$_2$ (hydrazide), maleimide, activated ester, aldehyde, ketone, hydroxylamine, imidoester, isocyanate, isothiocyanate, sulfonylchloride, acylhalide, and —COOY, wherein Y is a member selected from H, a negative charge and a salt counter-ion.

7. The compound according to claim 1, wherein the functional moiety is a member selected from:

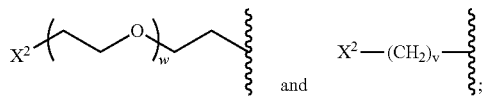
and

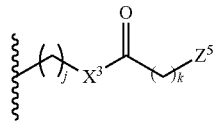

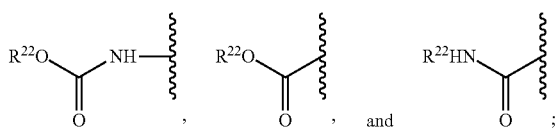

wherein X$^2$ is a member selected from OH, alkoxy, wherein R$^{22}$ is a member selected from H, substituted or unsubstituted alkyl, and substituted or unsubstituted aryl;
v is an integer from 1 to 20; and
w is an integer from 1 to 1,000.

8. The compound according to claim 1, wherein said functional moiety has the structure:

$$\text{\}(\ )_j X^3 \overset{O}{C} (\ )_k Z^5$$

wherein,
Z$^5$ is a member selected from H, OR$^{23}$, SR$^{23}$, NHR$^{23}$, OCOR$^{24}$, OC(O)NHR$^{24}$, NHC(O)OR$^{23}$, OS(O)$_2$OR$^{23}$, and C(O)R$^{24}$;
wherein
R$^{23}$ is a member selected from H, substituted or unsubstituted alkyl, and substituted or unsubstituted heteroalkyl;
R$^{24}$ is a member selected from H, OR$^{25}$, NR$^{25}$NH$_2$, SH, C(O)R$^{25}$, NR$^{25}$H, substituted or unsubstituted alkyl, and substituted or unsubstituted heteroalkyl;
wherein
R$^{25}$ is a member selected from H, substituted or unsubstituted alkyl, and substituted or unsubstituted alkyl;
X$^3$ is a member selected from O, S, and NR$^{26}$
wherein
R$^{26}$ is a member selected from H, substituted or unsubstituted alkyl, and substituted or unsubstituted heteroalkyl; and
j and k are members independently selected from the group consisting of integers from 1 to 20.

9. The compound according to claim 1, wherein said functional moiety comprises a polyether.

10. The compound according to claim 9, wherein said polyether is a member selected from polyethylene glycol (PEG) and derivatives thereof.

11. The compound according to claim 10, wherein said polyether has a molecular weight of about 50 to about 10,000 daltons.

12. The compound according to claim 1, having a structure selected from:

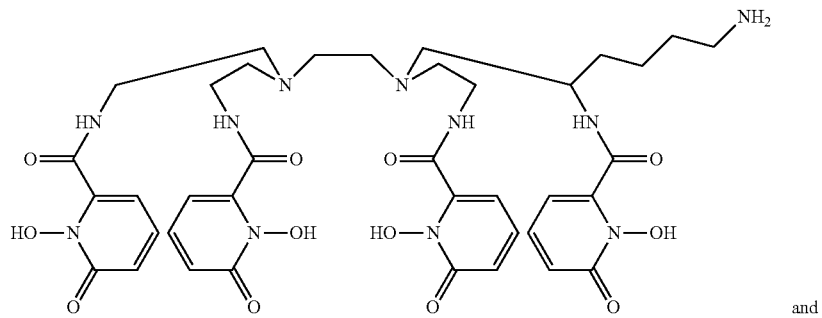

and

-continued

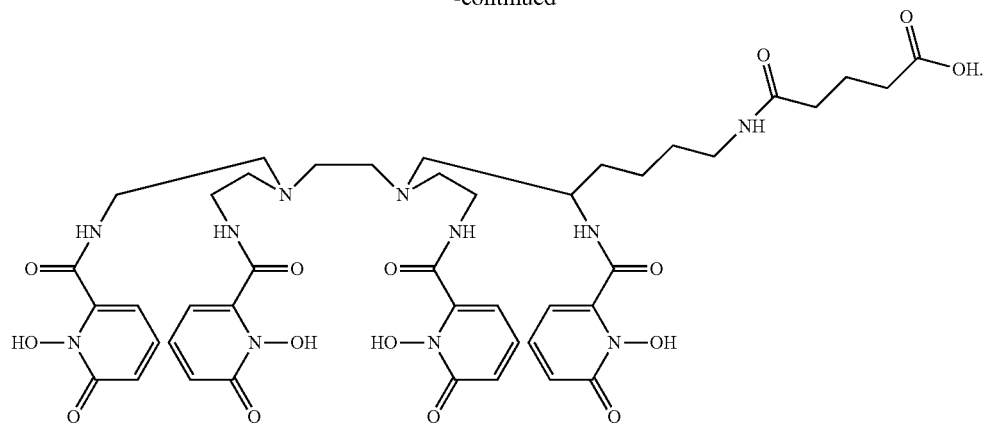

13. A complex comprising a compound according to claim 1 and a metal ion.

14. The complex according to claim 13, wherein said metal ion is selected from a lanthanide ion, an actinide ion, and a transition metal ion.

15. The complex according to claim 14, wherein said lanthanide ion is selected from $La^{3+}$, $Nd^{3+}$, $Sm^{3+}$, $Eu^{3+}$, $Gd^{3+}$, $Tb^{3+}$, $Dy^{3+}$, $Er^{3+}$, $Tm^{3+}$, $Yb^{3+}$, and $Lu^{3+}$.

16. The complex according to claim 14, wherein said actinide ion is selected from $U^{6+}$, $Np^{4+}$, $Np^{5+}$, $Pu^{4+}$, and $Am^{3+}$.

17. The complex according to claim 14, wherein said transition metal ion is $Fe^{3+}$.

18. The complex according to claim 13, wherein the metal is a radioactive isotope.

\* \* \* \* \*